US012568969B2

(12) United States Patent
Ahmad et al.

(10) Patent No.: US 12,568,969 B2
(45) Date of Patent: Mar. 10, 2026

(54) PYRIDINE COMPOUNDS FOR CONTROLLING INVERTEBRATE PESTS

(71) Applicant: FMC Corporation, Philadelphia, PA (US)

(72) Inventors: Omar Khaled Ahmad, Cambridge, MA (US); Twyla A. Briddell, Elkton, MD (US); Dominic Ming-Tak Chan, Wilmington, DE (US); Yuzhong Chen, Wilmington, DE (US); Jason Charles Hamm, Middletown, DE (US); Moumita Kar, Hyderabad (IN); Thomas Francis Pahutski, Jr., Elkton, MD (US); Thomas Martin Stevenson, Newark, DE (US); Ming Xu, Newark, DE (US); Rachel Slack, Bel Air, MD (US)

(73) Assignee: FMC Corporation, Phiadelphia, PA (US)

( * ) Notice: Subject to any disclaimer, the term of this patent is extended or adjusted under 35 U.S.C. 154(b) by 744 days.

(21) Appl. No.: 17/796,542

(22) PCT Filed: Jan. 29, 2021

(86) PCT No.: PCT/US2021/015643
§ 371 (c)(1),
(2) Date: Jul. 29, 2022

(87) PCT Pub. No.: WO2021/155106
PCT Pub. Date: Aug. 5, 2021

(65) Prior Publication Data

US 2023/0117403 A1 Apr. 20, 2023

Related U.S. Application Data

(60) Provisional application No. 62/967,838, filed on Jan. 30, 2020.

(51) Int. Cl.

| | |
|---|---|
| ***A01N 43/647*** | (2006.01) |
| ***A01N 25/04*** | (2006.01) |
| ***A01N 25/08*** | (2006.01) |
| ***A01N 25/12*** | (2006.01) |
| ***A01N 25/14*** | (2006.01) |
| ***A01N 25/34*** | (2006.01) |
| ***A01N 43/40*** | (2006.01) |
| ***A01N 43/50*** | (2006.01) |
| ***A01N 43/56*** | (2006.01) |
| ***A01N 43/653*** | (2006.01) |
| ***A01N 43/713*** | (2006.01) |
| ***A01N 43/76*** | (2006.01) |
| ***A01N 43/78*** | (2006.01) |

(Continued)

(52) U.S. Cl.
CPC ........... *A01N 43/647* (2013.01); *A01N 25/04* (2013.01); *A01N 25/08* (2013.01); *A01N 25/12* (2013.01); *A01N 25/14* (2013.01); *A01N 25/34* (2013.01); *A01N 43/40* (2013.01); *A01N 43/50* (2013.01); *A01N 43/56* (2013.01); *A01N 43/653* (2013.01); *A01N 43/713* (2013.01); *A01N 43/76* (2013.01); *A01N 43/78* (2013.01); *A01N 43/80* (2013.01); *A01N 43/82* (2013.01); *A01N 51/00* (2013.01); *A01P 7/04* (2021.08); *C07D 401/04* (2013.01); *C07D 401/14* (2013.01); *C07D 405/04* (2013.01); *C07D 405/14* (2013.01); *C07D 409/04* (2013.01); *C07D 413/04* (2013.01); *C07D 417/04* (2013.01)

(58) Field of Classification Search
CPC ...... A01N 43/50; A01N 43/56; A01N 43/647; A01N 43/653; A01N 43/713; A01N 43/76; A01N 43/78; A01N 43/80; A01N 43/82; C07D 401/04; C07D 401/14; C07D 405/04; C07D 405/14; C07D 409/04; C07D 413/04; C07D 417/04
See application file for complete search history.

(56) References Cited

FOREIGN PATENT DOCUMENTS

| | | |
|---|---|---|
| WO | 2012/087630 | 6/2012 |
| WO | 2013/158422 | 10/2013 |

OTHER PUBLICATIONS

"Opportunities for Chiral Agrochemicals," Williams, A., Pestic. Sci., 46, 3-9, 1995.*

(Continued)

*Primary Examiner* — Valerie Rodriguez-Garcia
(74) *Attorney, Agent, or Firm* — FMC Corporation

(57) ABSTRACT

Disclosed are compounds of Formula 1, including all geometric and stereoisomers, N-oxides, and salts thereof,

1

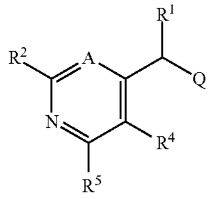

Wherein $R^1$, A, $R^2$, $R^4$, $R^5$ and Q are as defined in the disclosure. Also disclosed are compositions containing the compounds of Formula 1 and methods for controlling an invertebrate pest comprising contacting the invertebrate pest or its environment with a biologically effective amount of a compound or a composition of the disclosure.

12 Claims, No Drawings

(51) Int. Cl.

| | |
|---|---|
| *A01N 43/80* | (2006.01) |
| *A01N 43/82* | (2006.01) |
| *A01N 51/00* | (2006.01) |
| *A01P 7/04* | (2006.01) |
| *C07D 401/04* | (2006.01) |
| *C07D 401/14* | (2006.01) |
| *C07D 405/04* | (2006.01) |
| *C07D 405/14* | (2006.01) |
| *C07D 409/04* | (2006.01) |
| *C07D 413/04* | (2006.01) |
| *C07D 417/04* | (2006.01) |

(56) References Cited

OTHER PUBLICATIONS

Patrick, G. L. "An Introduction to Medicinal Chemistry," 6th Edition, Oxford, 2017, pp. 223-253, at 224-225, 230-231.*
Kubinyi (3D QSAR in Drug Design: Ligand-Protein Interactions and Molecular Similarity, vol. 2-3, Springer, 1998, see p. 243).*
International Search Report of corresponding PCT International Application No. PCT/US2021/015643.

* cited by examiner

PYRIDINE COMPOUNDS FOR CONTROLLING INVERTEBRATE PESTS

CROSS-REFERENCE TO RELATED APPLICATIONS

This application claims the benefit of U.S. Provisional Application No. 62/967,838 filed Jan. 30, 2020.

FIELD

This disclosure relates to certain pyridine compounds, their N-oxides, salts and compositions suitable for agronomic and nonagronomic uses, and methods of their use for controlling invertebrate pests such as arthropods in both agronomic and nonagronomic environments.

BACKGROUND

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public and animal health is also important. Many products are commercially available for these purposes, but the need continues for new compounds that are more effective, less costly, less toxic, environmentally safer or have different sites of action.

SUMMARY

This disclosure is directed to compounds of Formula 1 (including all geometric and stereoisomers), N-oxides, and salts thereof, and compositions containing them and their use for controlling invertebrate pests:

1

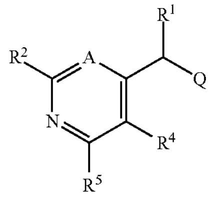

wherein $R^1$ is F, $OR^6$ or $S(O)R^6$;

A is N or $CR^3$;

$R^2$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^3$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^4$ is a 5- to 6-membered heterocyclic ring, each ring containing ring members selected from carbon atoms and 1 to 4 heteroatoms independently selected from up to 2 O, up to 2 S and up to 4 N atoms, wherein up to 2 ring members are independently selected from C(═O), C(═S), S(═O) and $S(═O)_2$, each ring optionally substituted with up to 5 substituents independently selected from $R^v$, and r is the number of the substituents.

each $R^v$ is independently H, cyano, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_2$-$C_6$ cyanoalkyl, $C_1$-$C_6$ hydroxyalkyl, $C_4$-$C_{10}$ alkylcycloalkyl, $C_4$-$C_{10}$ cycloalkylalkyl, $C_3$-$C_6$ cycloalkenyl, $C_3$-$C_6$ halocycloalkenyl, $C_2$-$C_6$ alkoxyalkyl, $C_4$-$C_{10}$ cycloalkoxyalkyl, $C_3$-$C_{10}$ alkoxyalkoxyalkyl, $C_2$-$C_6$ alkylthioalkyl, $C_2$-$C_6$ alkylsulfinylalkyl, $C_3$-$C_6$ cycloalkoxy, $C_3$-$C_6$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkoxyalkoxy, $C_2$-$C_6$ alkylcarbonyloxy, $C_1$-$C_6$ alkylthio, $C_1$-$C_6$ haloalkylthio, $C_3$-$C_6$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_6$ cycloalkylsulfonyl, $C_1$-$C_6$ alkylamino, $C_2$-$C_6$ dialkylamino, $C_1$-$C_6$ haloalkylamino, $C_2$-$C_6$ halodialkylamino or $C_3$-$C_6$ cycloalkylamino;

r is 1, 2, 3, 4 or 5;

$R^5$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^6$ is $C_1$-$C_4$ alkyl, $C_1$-$C_4$ haloalkyl, $C_3$-$C_4$ cycloalkyl or $C_3$-$C_4$ halocycloalkyl;

Q is a six membered aromatic ring containing ring members selected from carbon atoms and up to 2 nitrogen atoms, each ring optionally substituted on carbon atom ring members with up to 5 substituents independently selected from one or more $R^w$; and s is the number of the substituents;

$R^w$ is independently H, cyano, halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_2$-$C_6$ cyanoalkyl, $C_1$-$C_6$ hydroxyalkyl, $C_4$-$C_{10}$ alkylcycloalkyl, $C_4$-$C_{10}$ cycloalkylalkyl, $C_3$-$C_6$ cycloalkenyl, $C_3$-$C_6$ halocycloalkenyl, $C_2$-$C_6$ alkoxyalkyl, $C_4$-$C_{10}$ cycloalkoxyalkyl, $C_3$-$C_{10}$ alkoxyalkoxyalkyl, $C_2$-$C_6$ alkylthioalkyl, $C_2$-$C_6$ alkylsulfinylalkyl, $C_1$-$C_6$ alkoxy, $C_1$-$C_6$ haloalkoxy, $C_3$-$C_6$ cycloalkoxy, $C_3$-$C_6$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkoxyalkoxy, $C_2$-$C_6$ alkylcarbonyloxy, $C_1$-$C_6$ alkylthio, $C_1$-$C_6$ haloalkylthio, $C_3$-$C_6$ cycloalkylthio, $C_1$-$C_6$ alkylsulfinyl, $C_1$-$C_6$ haloalkylsulfinyl, $C_3$-$C_6$ cycloalkylsulfinyl, $C_1$-$C_6$ alkylsulfonyl, $C_1$-$C_6$ haloalkylsulfonyl, $C_3$-$C_6$ cycloalkylsulfonyl, $C_1$-$C_6$ alkylamino, $C_2$-$C_6$ dialkylamino, $C_1$-$C_6$ haloalkylamino, $C_2$-$C_6$ halodialkylamino or $C_3$-$C_6$ cycloalkylamino; or two $R^w$ on adjacent carbon atoms together can form a —OCF2O—, —OCH2O—, —OCF2S—, —OCH2CH2)-, OCF2CF2O— cyclic ether ring;

s is 1, 2, 3, 4 or 5;

n is 0, 1 or 2;

with the proviso that 1) when $R^1$ is F, $R^2$ is H, A is $CR^3$ wherein $R^3$ is F, $R^4$ is pyrazol-1-yl and $R^5$ is H, Q is other than 4-$OCF_3$-phenyl; and 2) $R^4$ is other than pyridinyl.

This disclosure also provides a composition comprising a compound of Formula 1, an N-oxide or a salt thereof, and at least one additional component selected from the group consisting of surfactants, solid diluents and liquid diluents. In one embodiment, this disclosure also provides a composition for controlling an invertebrate pest comprising a compound of Formula 1, an N-oxide or a salt thereof, and at least one additional component selected from the group consisting of surfactants, solid diluents and liquid diluents, said composition optionally further comprising at least one additional biologically active compound or agent.

This disclosure also provides a method for controlling an invertebrate pest comprising contacting the invertebrate pest or its environment with a biologically effective amount of a compound of Formula 1, an N-oxide or a salt thereof, (e.g., as a composition described herein). This disclosure also relates to such method wherein the invertebrate pest or its environment is contacted with a composition comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent.

This disclosure also provides a method for controlling an invertebrate pest comprising contacting the invertebrate pest or its environment with a biologically effective amount of any of the aforesaid compositions wherein the environment is a plant.

This disclosure also provides a method for controlling an invertebrate pest comprising contacting the invertebrate pest or its environment with a biologically effective amount of any of the aforesaid compositions wherein the environment is an animal.

This disclosure also provides a method for controlling an invertebrate pest comprising contacting the invertebrate pest or its environment with a biologically effective amount of any of the aforesaid compositions wherein the environment is a seed.

This disclosure also provides a method for protecting a seed from an invertebrate pest comprising contacting the seed with a biologically effective amount of a compound of Formula 1, an N-oxide or a salt thereof, (e.g., as a composition described herein). This disclosure also relates to the treated seed (i.e. seed contacted with a compound of Formula 1).

This disclosure also provides a method for increasing vigor of a crop plant comprising contacting the crop plant, the seed from which the crop plant is grown or the locus (e.g., growth medium) of the crop plant with a biologically effective amount of a compound of Formula 1 (e.g., as a composition described herein).

This disclosure further provides a method for protecting an animal from an invertebrate parasitic pest comprising administering to the animal a parasiticidally effective amount of a compound of Formula 1, an N-oxide or a salt thereof, (e.g., as a composition described herein). This disclosure also provides for the use of a compound of Formula 1, an N-oxide or a salt thereof, (e.g., as a composition described herein) in protecting an animal from an invertebrate pest.

DETAILED DESCRIPTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed disclosure. The term "consisting essentially of" occupies a middle ground between "comprising" and "consisting of".

Where applicants have defined an embodiment or a portion thereof with an open-ended term such as "comprising," it should be readily understood that (unless otherwise stated) the description should be interpreted to also describe such an embodiment using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the disclosure are intended to be nonrestrictive regarding the number of instances (i.e. occurrences) of the element or component. Therefore "a" or"an" should be read to include one or at least one, and the singular word form of the element or component also includes the plural unless the number is obviously meant to be singular.

As referred to in this disclosure, the term "invertebrate pest" includes arthropods, gastropods, nematodes and helminths of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes members of the phylum Nematoda, such as phytophagous nematodes and helminth nematodes parasitizing animals. The term "helminth" includes all of the parasitic worms, such as roundworms (phylum Nematoda), heartworms (phylum Nematoda, class Secernentea), flukes (phylum Platyhelminthes, class Tematoda), acanthocephalans (phylum Acanthocephala), and tapeworms (phylum Platyhelminthes, class Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field; crops such as for food and fiber and includes the growth of maize or corn, soybeans and other legumes, rice, cereal (e.g., wheat, oats, barley, rye and rice), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (e.g., berries and cherries) and other specialty crops (e.g., canola, sunflower and olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

The term "crop vigor" refers to rate of growth or biomass accumulation of a crop plant. An "increase in vigor" refers to an increase in growth or biomass accumulation in a crop plant relative to an untreated control crop plant. The term "crop yield" refers to the return on crop material, in terms of both quantity and quality, obtained after harvesting a crop plant. An "increase in crop yield" refers to an increase in crop yield relative to an untreated control crop plant.

The term "biologically effective amount" refers to the amount of a biologically active compound (e.g., a compound of Formula 1) sufficient to produce the desired biological effect when applied to (i.e. contacted with) an invertebrate pest to be controlled or its environment, or to a plant, the seed from which the plant is grown, or the locus of the plant (e.g., growth medium) to protect the plant from injury by the invertebrate pest or for other desired effect (e.g., increasing plant vigor).

Nonagronomic applications include protecting an animal from an invertebrate parasitic pest by administering a parasiticidally effective (i.e. biologically effective) amount of a compound of the disclosure, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction.

These effects on invertebrate parasite pests provide control (including prevention, reduction or elimination) of parasitic infestation or infection of the animal.

In the above recitations, the term "alkyl", used either alone or in compound words such as "alkylthio" or"haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH{=}CH$, $CH_2CH{=}CH$, $CH{=}C(CH_3)$ and the different butenylene isomers. "Alkynylene" denotes a straight-chain or branched alkynediyl containing one triple bond. Examples of "alkynylene" include $C{\equiv}C$, $CH_2C{\equiv}C$, $C{\equiv}CCH_2$ and the different butynylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C{=}CHCH_2O$, $(CH_3)_2C{=}CHCH_2O$, $(CH_3)CH{=}CHCH_2O$, $(CH_3)CH{=}C(CH_3)CH_2O$ and $CH_2{=}CHCH_2CH_2O$. "Alkynyloxy" includes straight-chain or branched alkynyloxy moieties. Examples of "alkynyloxy" include $HC{\equiv}CCH_2O$, $CH_3C{\equiv}CCH_2O$ and $CH_3C{\equiv}CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)-$, $CH_3CH_2S(O)-$, $CH_3CH_2CH_2S(O)-$, $(CH_3)_2CHS(O)-$ and the different butylsulfinyl, pentylsulfinyl and hexylsulfinyl isomers. Examples of "alkylsulfonyl" include $CH_3S(O)_2-$, $CH_3CH_2S(O)_2-$, $CH_3CH_2CH_2S(O)_2-$, $(CH_3)_2CHS(O)_2-$, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylthioalkoxy" denotes alkylthio substitution on alkoxy. "Alkyldithio" denotes branched or straight-chain alkyldithio moieties. Examples of "alkyldithio" include $CH_3SS-$, $CH_3CH_2SS-$, $CH_3CH_2CH_2SS-$, $(CH_3)_2CHSS-$ and the different butyldithio and pentyldithio isomers. "Cyanoalkyl" denotes an alkyl group substituted with one cyano group. Examples of "cyanoalkyl" include $NCCH_2$, $NCCH_2CH_2$ and $CH_3CH(CN)CH_2$. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. "Cyanocycloalkyl" denotes a cycloalkyl group substituted with one cyano group. Examples of "cyanocycloalkyl" include 4-cyanocyclohexyl and 3-cyanocyclopentyl. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C—$, $ClCH_2—$, $CF_3CH_2—$ and $CF_3CCl_2—$. The terms "halocycloalkyl", "haloalkoxy", "haloalkylthio", "haloalkenyl", "haloalkynyl", and the like, are defined analogously to the term "haloalkyl". Examples of "haloalkoxy" include $CF_3O—$, $CCl_3CH_2O—$, $HCF_2CH_2CH_2O—$ and $CF_3CH_2O—$. Examples of "haloalkylthio" include $CCl_3S—$, $CF_3S—$, $CCl_3CH_2S—$ and $ClCH_2CH_2CH_2S—$. Examples of "haloalkylsulfinyl" include $CF_3S(O)—$, $CCl_3S(O)—$, $CF_3CH_2S(O)—$ and $CF_3CF_2S(O)—$. Examples of "haloalkylsulfonyl" include $CF_3S(O)_2—$, $CCl_3S(O)_2—$, $CF_3CH_2S(O)_2—$ and $CF_3CF_2S(O)_2—$. Examples of "haloalkenyl" include $(Cl)_2C{=}CHCH_2—$ and $CF_3CH_2CH{=}CHCH_2—$. Examples of "haloalkynyl" include $HC{\equiv}CCHCl—$, $CF_3C{\equiv}C—$, $CCl_3C{\equiv}C—$ and $FCH_2C{\equiv}CCH_2—$. Examples of "haloalkoxyalkoxy" include $CF_3OCH_2O—$, $ClCH_2CH_2OCH_2CH_2O—$, $Cl_3CCH_2OCH_2O—$ as well as branched alkyl derivatives.

"Alkylcarbonyl" denotes a straight-chain or branched alkyl moieties bonded to a C(═O) moiety. Examples of "alkylcarbonyl" include $CH_3C({=}O)—$, $CH_3CH_2CH_2C({=}O)—$ and $(CH_3)_2CHC({=}O)—$. Examples of "alkoxycarbonyl" include $CH_3OC({=}O)—$, $CH_3CH_2OC({=}O)—$, $CH_3CH_2CH_2OC({=}O)—$, $(CH_3)_2CHOC({=}O)—$ and the different butoxy- or pentoxycarbonyl isomers.

The chemical abbreviations S(O) and S(═O) as used herein represent a sulfinyl moiety. The chemical abbreviations $SO_2$, $S(O)_2$ and $S({=}O)_2$ as used herein represent a sulfonyl moiety. The chemical abbreviations C(O) and C(═O) as used herein represent a carbonyl moiety. The chemical abbreviations $CO_2$, C(O)O and C(═O)O as used herein represent an oxycarbonyl moiety. "CHO" means formyl.

When $R^4$ is a 5- to 6-membered heterocyclic ring substituted with up to 5 substituents independently selected from $R^v$, the substituents $R^v$ may be attached to the remainder of the compound of Formula 1 through any available ring member of the heterocyclic ring.

When Q is a six membered aromatic ring substituted with up to 5 substituents independently selected from $R^w$, the substituents $R^w$ may be attached to the remainder of the compound of Formula 1 through any available ring member of the six membered aromatic ring.

The total number of carbon atoms in a substituent group is indicated by the "$C_i$-$C_j$" prefix where i and j are numbers from 1 to 10. For example, $C_1$-$C_4$ alkylsulfonyl designates methylsulfonyl through butylsulfonyl; $C_2$ alkoxyalkyl designates $CH_3OCH_2—$; $C_3$ alkoxyalkyl designates, for example, $CH_3CH(OCH_3)—$, $CH_3OCH_2CH_2—$ or $CH_3CH_2OCH_2—$; and $C_4$ alkoxyalkyl designates the various isomers of an alkyl group substituted with an alkoxy group containing a total of four carbon atoms, examples including $CH_3CH_2CH_2OCH_2—$ and $CH_3CH_2OCH_2CH_2—$.

When a compound is substituted with a substituent bearing a subscript that indicates the number of said substituents can exceed 1, said substituents (when they exceed 1) are independently selected from the group of defined substituents, e.g., $[(R^v)_r]$, r is 1, 2, 3, 4 or 5; and $[(R^w)_s]$, s is 1, 2, 3, 4 or 5. When a group contains a substituent which can be hydrogen, for example $R^v$ or $R^w$, then when this substituent is taken as hydrogen, it is recognized that this is equivalent to said group being unsubstituted. When one or more positions on a group are said to be "not substituted" or "unsubstituted", then hydrogen atoms are attached to take up any free valency.

Unless otherwise indicated, a "ring" as a component of Formula 1 (e.g., substituent $R^4$) is carbocyclic or heterocyclic. The term "ring member" refers to an atom or other moiety (e.g., C(═O), C(═S), S(O) or $S(O)_2$) forming the backbone of a ring.

The term "carbocyclic ring" or "carbocycle" denotes a ring wherein the atoms forming the ring backbone are selected only from carbon. The term "heterocyclic ring" or "heterocycle" denotes a ring in which at least one atom forming the ring backbone is not carbon, e.g., nitrogen, oxygen or sulfur. Typically, a heterocyclic ring contains no more than 4 nitrogens, no more than 2 oxygens and no more than 2 sulfurs. Unless otherwise indicated, a carbocyclic ring or heterocyclic ring can be a saturated or unsaturated ring. "Saturated" refers to a ring having a backbone consisting of atoms linked to one another by single bonds; unless otherwise specified, the remaining atom valences are occupied by hydrogen atoms.

Unless otherwise stated, an "unsaturated ring" may be partially unsaturated or fully unsaturated. The expression "fully unsaturated ring" means a ring of atoms in which the bonds between atoms in the ring are single or double bonds according to valence bond theory and furthermore the bonds between atoms in the ring include as many double bonds as possible without double bonds being cumulative (i.e. no C═C═C or C═C═N). The term "partially unsaturated ring" denotes a ring comprising at least one ring member bonded to an adjacent ring member through a double bond and which conceptually potentially accommodates a number of non-cumulated double bonds between adjacent ring members (i.e. in its fully unsaturated counterpart form) greater than the number of double bonds present (i.e. in its partially unsaturated form).

Unless otherwise indicated, heterocyclic rings can be attached through any available carbon or nitrogen by replacement of a hydrogen on said carbon or nitrogen.

"Aromatic" indicates that each of the ring atoms is essentially in the same plane and has a p-orbital perpendicular to the ring plane, and in which $(4n+2)$ $\pi$ electrons, where n is a positive integer, are associated with the ring to comply with Hückel's rule. When a fully unsaturated carbocyclic ring satisfies Hückel's rule, then said ring is also called an "aromatic ring" or "aromatic carbocyclic ring". When a fully unsaturated heterocyclic ring satisfies Hückel's rule, then said ring is also called a "heteroaromatic ring" or "aromatic heterocyclic ring".

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When $R^4$ is a 5- or 6-membered nitrogen-containing heterocyclic ring, it may be attached to the remainder of Formula 1 though any available carbon or nitrogen ring atom, unless otherwise described.

As noted above, $R^4$ can be a 5- or 6-membered heterocyclic ring, which may be saturated or unsaturated, optionally substituted with one or more substituents selected from a group of substituents as defined in the Summary. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary and r is an integer from 1 to 4, limited by the number of available positions on each U group. As U-29, U-30, U-36, U-37, U-38, U-39, U-40, U-41, U-42 and U-43 have only one available position, for these U groups r is limited to the integer 1, and when $R^v$ being H and r being 1 means that the U group is unsubstituted and a hydrogen is present at the position indicated by $(R^v)_r$.

Exhibit 1

U-2

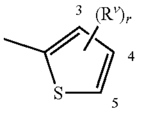

,

U-3

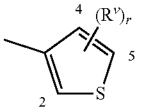

,

U-4

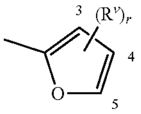

,

U-5

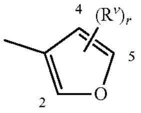

,

U-6

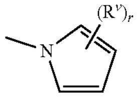

,

U-7

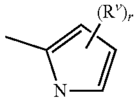

,

U-8

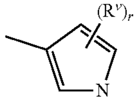

,

U-9

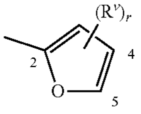

,

U-10

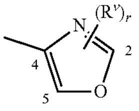

,

U-11

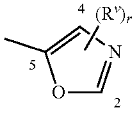

,

-continued

U-12

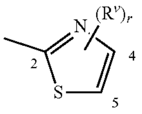

,

U-13

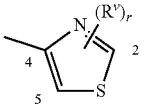

,

U-14

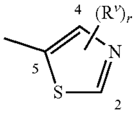

,

U-15

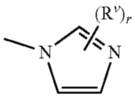

,

U-16

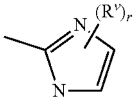

,

U-17

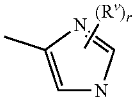

,

U-18

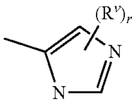

,

U-19

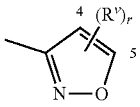

,

U-20

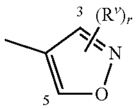

,

U-21

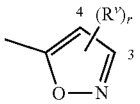

,

U-22

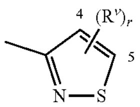

,

U-23

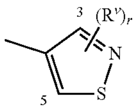

,

U-24

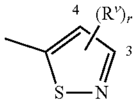

,

-continued
U-25
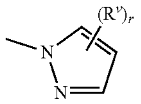
,
U-26
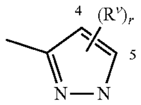
,
U-27
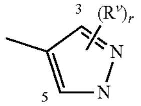
,
U-28
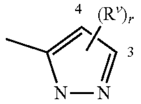
,
U-29
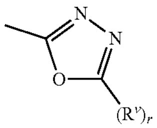
,
U-30
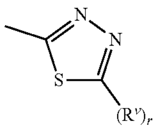
,
U-31
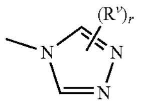
,
U-32
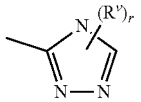
,
U-33
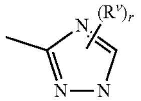
,
U-34
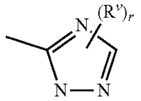
,
U-35
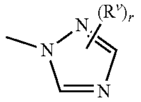
,
U-36
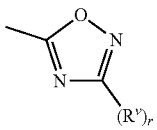
,
-continued
U-37
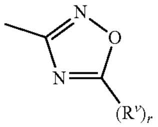
,
U-38
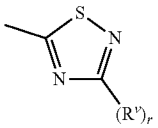
,
U-39
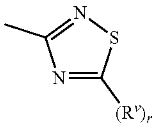
,
U-40
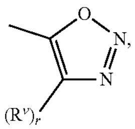
U-41
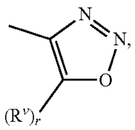
U-42
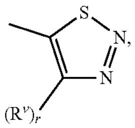
U-43
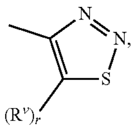
U-44
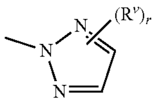
,
U-45
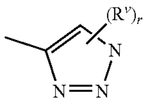
,
U-46
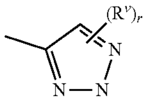
,
U-47
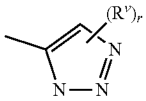
,
U-48
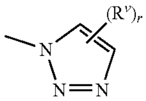
, -continued

U-49

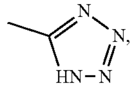

U-52

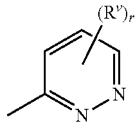

,

U-53

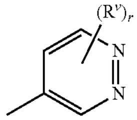

,

U-54

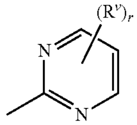

,

U-55

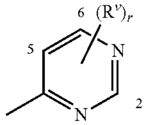

,

U-56

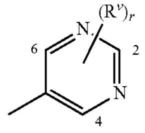

,

U-57

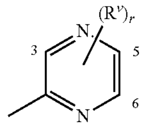

,

U-58

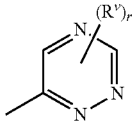

,

U-59

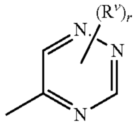

,

U-60

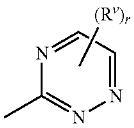

and

U-61

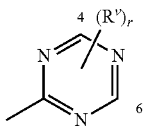

.

Note that when $R^4$ is a 5- or 6-membered saturated or unsaturated non-aromatic heterocyclic ring optionally substituted with one or more substituents selected from the group of substituents as defined in the Summary, one or two carbon ring members of the heterocycle can optionally be in the oxidized form of a carbonyl moiety.

Examples of a 5- or 6-membered saturated or non-aromatic unsaturated heterocyclic ring include the rings G-1 through G-35 as illustrated in Exhibit 2. Note that when the attachment point on the G group is illustrated as floating, the G group can be attached to the remainder of Formula 1 through any available carbon or nitrogen of the G group by replacement of a hydrogen atom. The optional substituents corresponding to $R^v$ can be attached to any available carbon or nitrogen by replacing a hydrogen atom. For these G rings, s is typically an integer from 1 to 5, limited by the number of available positions on each G group.

Note that when $R^4$ comprises a ring selected from G-28 through G-35, $G^2$ is selected from O, S or N. Note that when $G^2$ is N, the nitrogen atom can complete its valence by substitution with the substituents corresponding to $R^w$ as defined in the Summary.

Exhibit 2

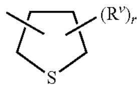

, G-1

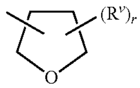

, G-2

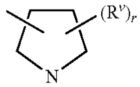

, G-3

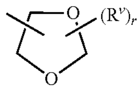

, G-4

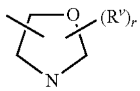

, G-5

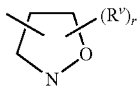

, G-6

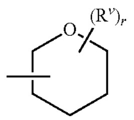

, G-7

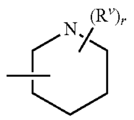

, G-8

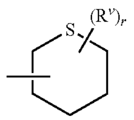

, G-9

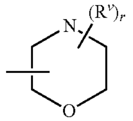

, G-10

-continued

G-11

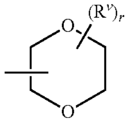
,

G-12

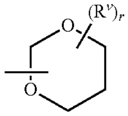
,

G-13

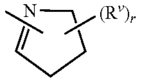
,

G-14

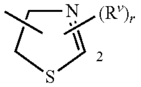
,

G-15

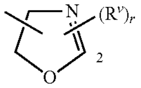
,

G-16

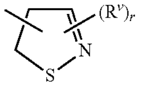
,

G-17

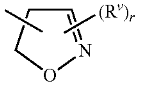
,

G-18

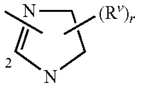
,

G-19

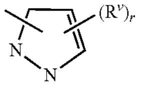
,

G-20

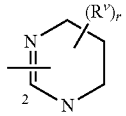
,

G-21

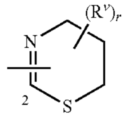
,

G-22

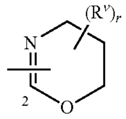
,

G-23

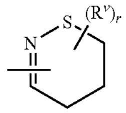
,

G-24

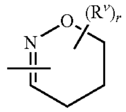
,

-continued

G-25

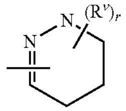
,

G-26

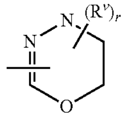
,

G-27

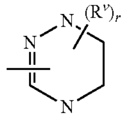
,

G-28

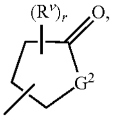

G-29

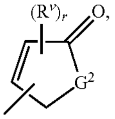

G-30

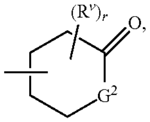

G-31

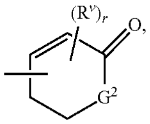

G-32

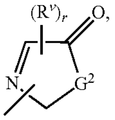

G-33

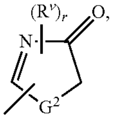

G-34

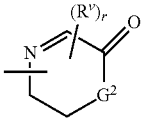
and

G-35

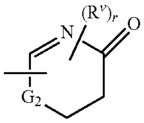
.

Although $R^v$ groups are shown in the structures U-2 through U-61, it is noted that they do not need to be present since they are optional substituents. Note that when $R^v$ is H attached to an atom, this is the same as if said atom is unsubstituted. The nitrogen atoms that require substitution to fill their valence are substituted with H or $R^v$. Note that when the attachment point between $(R^v)_r$ and the U ring is illustrated as floating, $(R^v)_r$ can be attached to any available carbon atom or nitrogen atom of the U ring. Note that when the attachment point on the U ring is illustrated as floating, the U group can be attached to the remainder of Formula 1 through any available carbon or nitrogen of the U group by replacement of a hydrogen atom. Note that some U rings can only be substituted with less than 4 $R^v$ groups (e.g., U-2 through U-5, U-7 through U-49, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this disclosure can exist as one or more stereoisomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. For a comprehensive discussion of all aspects of stereoisomerism, see Ernest L. Eliel and Samuel H. Wilen, *Stereochemistry of Organic Compounds*, John Wiley & Sons, 1994.

The compounds of the disclosure may be present as a mixture of stereoisomers or individual stereoisomers. For example, two possible enantiomers of Formula 1 are depicted as Formula 1aa and Formula 1aa' involving a chiral carbon center identified with an asterisk (*). Analogously, other chiral centers are possible at, for example, $R^4$.

1a

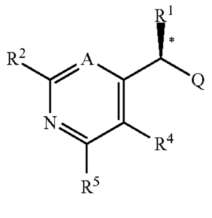

1a'

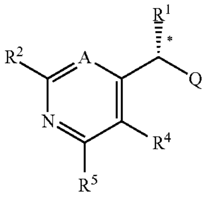

Molecular depictions drawn herein follow standard conventions for depicting stereochemistry. To indicate stereo configuration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the broad end of the wedge is attached to the atom further away from the viewer.

The compounds of the disclosure can exist as stereoisomers due to the possible chiral carbon atoms present in Formula 1. Thus, this disclosure comprises the individual stereoisomers of the compounds of Formula 1, as well as mixtures of stereoisomers of the compounds of Formula 1.

Compounds of Formula 1 can comprise additional chiral centers. For example, substituents and other molecular constituents such as $R^4$ may themselves contain chiral centers. This disclosure comprises racemic mixtures as well as enriched and essentially pure stereo configurations at these additional chiral centers.

Compounds of this disclosure can exist as one or more conformational isomers due to restricted rotation about any bonds in Formula 1. This disclosure comprises mixtures of conformational isomers. In addition, this disclosure includes compounds that are enriched in one conformer relative to others.

The more biologically active enantiomer is believed to be Formula 1a (the R-enantiomer of Formula 1.

This disclosure comprises racemic mixtures of equal amounts of the enantiomers of Formulae 1a (the R-enantiomer of Formula 1) and 1a' (the S-enantiomer of Formula 1). In addition, this disclosure includes mixtures that are enriched in the Formula 1a enantiomer compared to the racemic mixture of Formulae 1a and 1a'. This disclosure also comprises the essentially pure enantiomer of Formula 1a.

An embodiment of this disclosure comprises mixtures of stereoisomers of the compounds of Formula 1a and Formula 1a', wherein the ratio of 1a to 1a' is at least 75:25 (a 50% enantiomeric excess).

An embodiment of this disclosure comprises mixtures of stereoisomers of the compounds of Formula 1a and Formula 1a', wherein the ratio of 1a to 1a' is at least 90:10 (an 80% enantiomeric excess of 1a).

An embodiment of this disclosure comprises mixtures of stereoisomers of the compounds of Formula 1a and Formula 1a', wherein the ratio of 1a to 1a' is at least 95:5 (a 90% enantiomeric excess of 1a).

An embodiment of this disclosure comprises mixtures of stereoisomers of the compounds of Formula 1a and Formula 1a', wherein the ratio of 1a to 1a' is at least 98:2 (a 96% enantiomeric excess of 1a).

An embodiment of this disclosure comprises mixtures of stereoisomers of the compounds of Formula 1a and Formula 1a', wherein the ratio of 1a to 1a' is at least 99:1 (a 98% enantiomeric excess of 1a).

An embodiment of this disclosure comprises mixtures of stereoisomers of the compounds of Formula 1a and Formula 1a', wherein the ratio of 1a to 1a' is essentially 100:0.

An embodiment of this disclosure comprises the compounds of Formula 1a.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides.

Synthetic methods for the preparation of N-oxides of heterocycles and tertiary amines are very well known by one skilled in the art including the oxidation of heterocycles and tertiary amines with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of invertebrate pests. The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present disclosure comprises compounds selected from Formula 1, N-oxides and suitable salts thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures. Compounds of this disclosure may exist as one or more crystalline polymorphs. This disclosure comprises both individual polymorphs and mixtures of polymorphs, including mixtures enriched in one polymorph relative to others. For a comprehensive discussion of polymorphism see R. Hilfiker, Ed., *Polymorphism in the Pharmaceutical Industry*, Wiley-VCH, Weinheim, 2006.

Embodiments of the present disclosure as described in the Summary include those described below. In the following Embodiments, Formula 1 includes stereoisomers, N-oxides and salts thereof, and reference to "a compound of Formula 1" includes the definitions of substituents specified in the Summary unless further defined in the Embodiments.

Embodiment 1. A compound of Formula 1 wherein $R^1$ is F, $OR^6$ or $SR^6$.

Embodiment 1a. A compound of Formula 1 or Embodiment 1 wherein $R^1$ is F.

Embodiment 1b. A compound of Formula 1 or Embodiment 1 wherein $R^1$ is $OR^6$.

Embodiment 1c. A compound of Formula 1 or Embodiment 1 wherein $R^1$ is $SR^6$.

Embodiment 2. A compound of Formula 1 or any one of the preceding Embodiments wherein A is N or $CR^3$.

Embodiment 2a. A compound of Formula 1 or any one of the preceding Embodiments wherein A is N.

Embodiment 2b. A compound of Formula 1 or any one of the preceding Embodiments wherein A is $CR^3$.

Embodiment 3. A compound of Formula 1 or any one of the preceding Embodiments wherein $R^2$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy.

Embodiment 3a. A compound of Formula 1 or any one of the preceding Embodiments wherein $R^2$ is H, halogen or $C_1$-$C_4$ alkyl.

Embodiment 3b. A compound of Embodiment 3 wherein $R^2$ is H.

Embodiment 3c. A compound of Embodiment 3 wherein $R^2$ is halogen.

Embodiment 3d. A compound of Embodiment 3 wherein $R^2$ is $C_1$-$C_4$ alkyl.

Embodiment 4. A compound of Formula 1 or any one of the preceding Embodiments wherein $R^3$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy.

Embodiment 4a. A compound of Embodiment 4 wherein $R^3$ is H, halogen, $C_1$-$C_4$ alkyl, $C_1$-$C_4$ haloalkyl, $C_1$-$C_4$ alkoxy or $C_1$-$C_4$ haloalkoxy.

Embodiment 4b. A compound of Embodiment 4a wherein $R^3$ is H or halogen.

Embodiment 4c. A compound of Embodiment 4b wherein $R^3$ is H.

Embodiment 4d. A compound of Embodiment 4a wherein $R^3$ is halogen.

Embodiment 4f. A compound of Embodiment 4d wherein $R^3$ is F.

Embodiment 4g. A compound of Embodiment 4d wherein $R^3$ is Cl.

Embodiment 4h. A compound of Embodiment 4d wherein $R^3$ is Br.

Embodiment 4i. A compound of Embodiment 4a wherein $R^3$ is $C_1$-$C_4$ alkyl.

Embodiment 4j. A compound of Embodiment 4i wherein $R^3$ is Me.

Embodiment 4k. A compound of Embodiment 4a wherein $R^3$ is $C_1$-$C_4$ haloalkyl.

Embodiment 4l. A compound of Embodiment 4k wherein $R^3$ is $CF_3$.

Embodiment 5. A compound of Formula 1 or any one of the preceding Embodiments wherein $R^4$ is a 5- to 6-membered heterocyclic ring, each ring containing ring members selected from carbon atoms and 1 to 4 heteroatoms independently selected from up to 2 O, up to 2 S and up to 4 N atoms, wherein up to 2 ring members are independently selected from C(═O), C(═S), S(═O) and $S(═O)_2$, each ring or ring system optionally substituted with up to 5 substituents independently selected from $R^v$, and r is the number of the substituents.

Embodiment 5a. A compound of Embodiment 5 wherein $R^4$ is selected from U-2 to U-49 or U52 to U61 as shown in Exhibit 1.

Exhibit 1

U-2

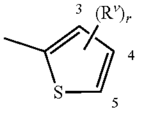,

U-3

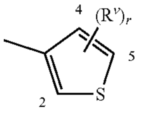,

U-4

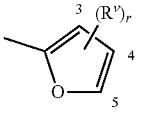,

U-5

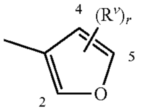,

U-6

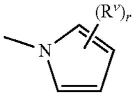,

U-7

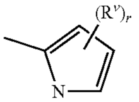,

U-8

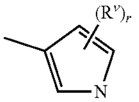,

U-9

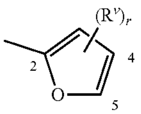,

U-10

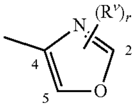,

-continued

U-11

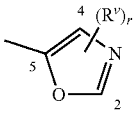,

U-12

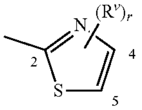,

U-13

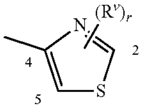,

U-14

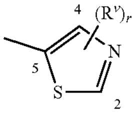,

U-15

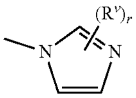,

U-16

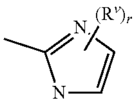,

U-17

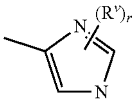,

U-18

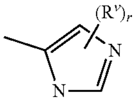,

U-19

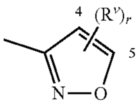,

U-20

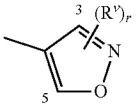,

U-21

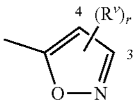,

U-22

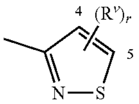,

-continued
U-23
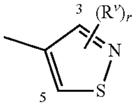,
U-24
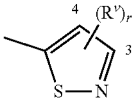,
U-25
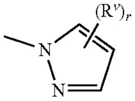,
U-26
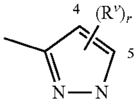,
U-27
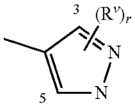,
U-28
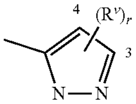,
U-29
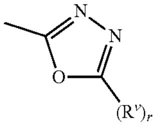,
U-30
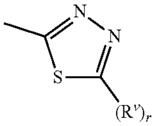,
U-31
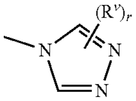,
U-32
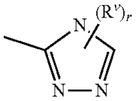,
U-33
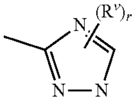,
U-34
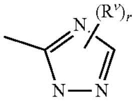,
U-35
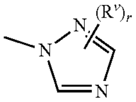,
-continued
U-36
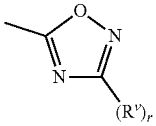,
U-37
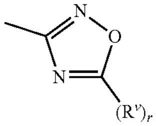,
U-38
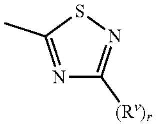,
U-39
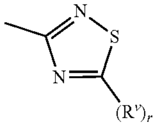,
U-40
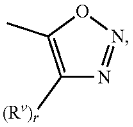
U-41
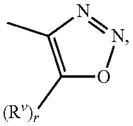
U-42
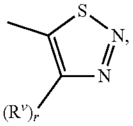
U-43
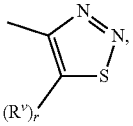
U-44
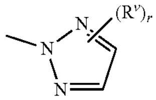,
U-45
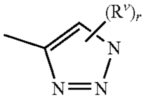,
U-46
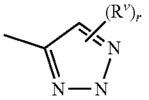,
U-47
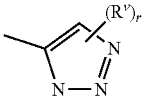, -continued

U-48

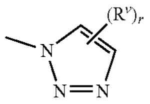
,

U-49

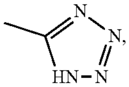

U-52

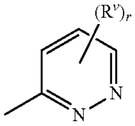
,

U-53

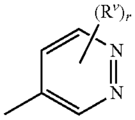
,

U-54

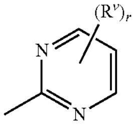
,

U-55

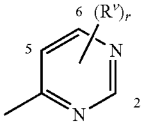
,

U-56

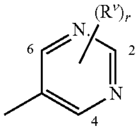
,

U-57

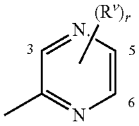
,

U-58

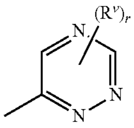
,

U-59

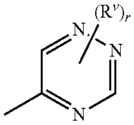
,

U-60

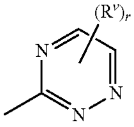
and

-continued

U-61

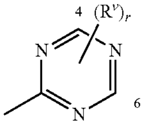
.

Embodiment 5b. A compound of Embodiment 5a wherein $R^4$ is selected from U-2 to U-49.

Embodiment 5c. A compound of Embodiment 5b wherein $R^4$ is selected from U-2, U-3, U-4, U-5, U-7, U-9, U-11, U-12, U-13, U-16, U-21, U-25, U-26, U-27, U-28, U-29, U-31, U-32, U-35, U-36, U-37, U-44, U-48 and U-49.

Embodiment 5d. A compound of Embodiment 5c wherein $R^4$ is selected from U-9, U-11, U-32, U-36 and U-44.

Embodiment 5e. A compound of Embodiment 5d wherein $R^4$ is selected from U-9 and U-44.

Embodiment 5f. A compound of Embodiment 5e wherein $R^4$ is U-9.

Embodiment 5g. A compound of Embodiment 5d wherein $R^4$ is U-11.

Embodiment 5h. A compound of Embodiment 5d wherein $R^4$ is U-32.

Embodiment 5i. A compound of Embodiment 5d wherein $R^4$ is U-36.

Embodiment 5j. A compound of Embodiment 5d wherein $R^4$ is U-44.

Embodiment 5k. A compound of Embodiment 5 wherein $R^4$ is selected from G-1 to G-37 as shown in Exhibit 2.

Exhibit 2

G-1

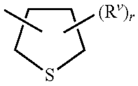
,

G-2

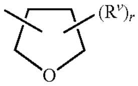
,

G-3

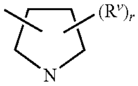
,

G-4

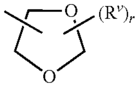
,

G-5

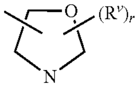
,

G-6

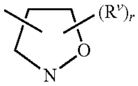
,

G-7

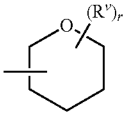
,

-continued
G-8
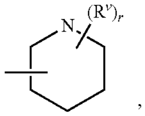
G-9
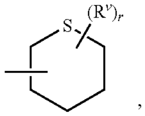
G-10
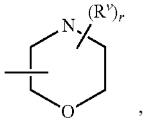
G-11
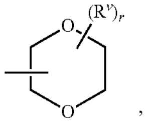
G-12
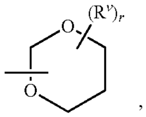
G-13
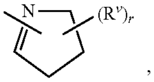
G-14
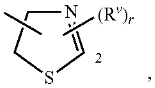
G-15
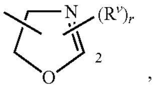
G-16
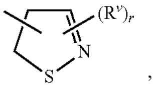
G-17
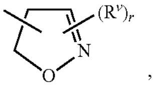
G-18
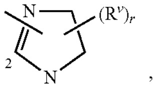
G-19
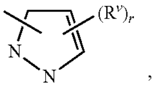
G-20
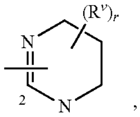
G-21
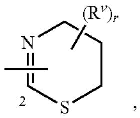
-continued
G-22
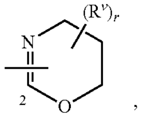
G-23
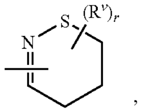
G-24
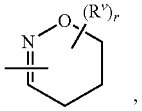
G-25
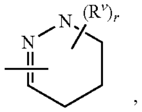
G-26
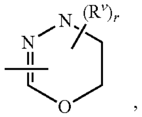
G-27
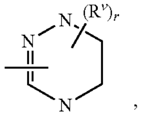
G-28
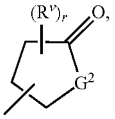
G-29
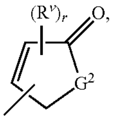
G-30
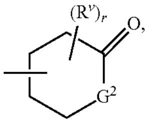
G-31
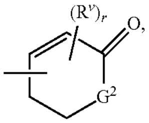
G-32
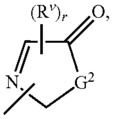
G-33
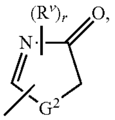

-continued

G-34

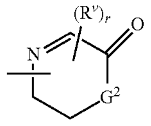

and

G-35

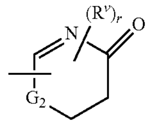

.

G-36

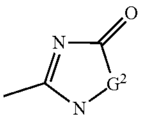

G-37

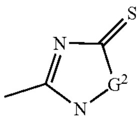

Embodiment 5l. A compound of Embodiment 5k wherein $G^2$ is O, S or N.

Embodiment 5m. A compound of Embodiment 5l wherein $G^2$ is O.

Embodiment 5n. A compound of Embodiment 5l wherein $G^2$ is S.

Embodiment 5o. A compound of Embodiment 5l wherein $G^2$ is N.

Embodiment 6. A compound of Formula 1 or any one of the preceding Embodiments wherein $R^v$ is independently H, halogen, $C_1$-$C_6$ alkyl, $C_1$-$C_6$ haloalkyl, $C_1$-$C_6$ alkoxy or $C_1$-$C_6$ haloalkoxy.

Embodiment 6a. A compound of Embodiment 6 wherein $R^v$ is H.

Embodiment 6b. A compound of Embodiment 6 wherein $R^v$ is halogen.

Embodiment 6c. A compound of Embodiment 6 wherein $R^v$ is $C_1$-$C_6$ alkyl.

Embodiment 6d. A compound of Embodiment 6c wherein $R^v$ is Me.

Embodiment 7. A compound of Formula 1 or any one of Embodiments 5 to 6d wherein r is 1, 2, 3, 4 or 5.

Embodiment 7a. A compound of Embodiment 7 wherein r is 1 or 2.

Embodiment 7b. A compound of Embodiment 7 wherein r is 1.

Embodiment 7c. A compound of Embodiment 7 wherein r is 2.

Embodiment 7d. A compound of Embodiment 7 wherein r is 3.

Embodiment 7e. A compound of Embodiment 7 wherein r is 4.

Embodiment 7f. A compound of Embodiment 7 wherein r is 5.

Embodiment 8. A compound of Formula 1 or any one of the preceding Embodiments wherein $R^5$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy.

Embodiment 8a. A compound of Embodiment 8 wherein $R^5$ is H, halogen, $C_1$-$C_4$ alkyl, $C_1$-$C_4$ haloalkyl, $C_1$-$C_4$ alkoxy or $C_1$-$C_4$ haloalkoxy.

Embodiment 8b. A compound of Embodiment 8a wherein $R^5$ is H or halogen.

Embodiment 8c. A compound of Embodiment 8b wherein $R^5$ is H.

Embodiment 8d. A compound of Embodiment 8b wherein $R^5$ is halogen.

Embodiment 8e. A compound of Embodiment 8d wherein $R^5$ is F.

Embodiment 8e. A compound of Embodiment 8d wherein $R^5$ is Cl.

Embodiment 8e. A compound of Embodiment 8d wherein $R^5$ is Br.

Embodiment 8e. A compound of Embodiment 8a wherein $R^5$ is $C_1$-$C_4$ alkyl.

Embodiment 9. A compound of Formula 1 or any one of the preceding Embodiments wherein $R^6$ is $C_1$-$C_4$ alkyl, $C_1$-$C_4$ haloalkyl, $C_3$-$C_4$ cycloalkyl or $C_3$-$C_4$ halocycloalkyl.

Embodiment 9a. A compound of Embodiment 9 wherein $R^6$ is $C_1$-$C_4$ alkyl or $C_1$-$C_4$ haloalkyl.

Embodiment 9b. A compound of Embodiment 9 wherein $R^6$ is $C_1$-$C_4$ alkyl.

Embodiment 9c. A compound of Embodiment 9b wherein $R^6$ is Me; Embodiment 9d. A compound of Embodiment 9 wherein $R^6$ is $C_1$-$C_4$ haloalkyl.

Embodiment 9e. A compound of Embodiment 9b wherein $R^6$ is $CF_3$.

Embodiment 10. A compound of Formula 1 or any one of the preceding Embodiments wherein Q is a six membered aromatic ring with 0 to 2 N on the ring, each ring optionally substituted on carbon atom ring members with up to 5 substituents independently selected from $R^w$.

Embodiment 10a. A compound of Embodiment 10 wherein Q is a phenyl, pyridinyl, pyrimidinyl or pyrazinyl ring, each ring optionally substituted on carbon atom ring members with up to 5 substituents independently selected from $R^w$.

Embodiment 10b. A compound of Embodiment 10a wherein Q is a phenyl ring optionally substituted on carbon atom ring members with up to 5 substituents independently selected from $R^w$.

Embodiment 10c. A compound of Embodiment 10a wherein Q is a pyridinyl ring optionally substituted on carbon atom ring members with up to 5 substituents independently selected from $R^w$.

Embodiment 10d. A compound of Embodiment 10a wherein Q is a pyrimidinyl ring optionally substituted on carbon atom ring members with up to 5 substituents independently selected from $R^w$.

Embodiment 10e. A compound of Embodiment 10a wherein Q is a pyrazinyl ring optionally substituted on carbon atom ring members with up to 5 substituents independently selected from $R^w$.

Embodiment 11. A compound of Formula 1 or any one of Embodiments 9 through 9e wherein $R^w$ is independently H, cyano, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_6$ alkoxyalkoxy, $C_1$-$C_6$ alkylthio, $C_1$-$C_6$ haloalkylthio, $C_3$-$C_6$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl or $C_3$-$C_6$ cycloalkylsulfonyl;

Embodiment 11a. A compound of Embodiment 11 wherein $R^w$ is cyano, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl.

Embodiment 11b. A compound of Embodiment 11a wherein $R^w$ is $C_1$-$C_6$ haloalkoxy, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl.

Embodiment 11c. A compound of Embodiment 11b wherein $R^w$ is $C_1$-$C_6$ haloalkoxy, $C_1$-$C_6$ haloalkyl, $C_2$-$C_6$ haloalkenyl, $C_2$-$C_6$ haloalkynyl, $C_1$-$C_6$ haloalkylthio, $C_1$-$C_6$ haloalkylsulfinyl, $C_1$-$C_6$ haloalkylsulfonyl.

Embodiment 11d. A compound of Embodiment 11c wherein $R^w$ is $OCF_3$, $SCF_3$, $CF_3$, $SOCF_3$ or $SO_2CF_3$.

Embodiment 11e. A compound of Embodiment 11d wherein $R^w$ is $OCF_3$.

Embodiment 11f. A compound of Embodiment 11d wherein $R^w$ is $SCF_3$.

Embodiment 11g. A compound of Embodiment 11d wherein $R^w$ is $CF_3$.

Embodiment 11h. A compound of Embodiment 11d wherein $R^w$ is $SOCF_3$ or $SO_2CF_3$.

Embodiment 12. A compound of Formula 1 or any one of the preceding Embodiments wherein s is 1, 2, 3, 4 or 5.

Embodiment 12a. A compound of Embodiment 12 wherein r is 1 or 2.

Embodiment 12b. A compound of Embodiment 12 wherein r is 1.

Embodiment 12c. A compound of Embodiment 12 wherein r is 2.

Embodiment 12d. A compound of Embodiment 12 wherein r is 3.

Embodiment 12e. A compound of Embodiment 12 wherein r is 4.

Embodiment 12f. A compound of Embodiment 12 wherein r is 5.

Embodiment 13. A compound of Formula 1 or any one of the preceding Embodiments wherein n is 0, 1 or 2.

Embodiment 13a. A compound of Embodiment 13 wherein n is 0.

Embodiment 13b. A compound of Embodiment 13 wherein n is 1.

Embodiment 13c. A compound of Embodiment 13 wherein n is 2.

Embodiment A1. A compound of any one of Embodiments 1-13c wherein the compound of Formula 1 is a compound of Formula 1a.

Embodiment A2. A compound of any one of Embodiments 1-13c wherein the compound of Formula 1 is a compound of Formula 1a'.

Embodiment A3. A composition comprising a compound of Formula 1a and a compound of Formula 1a'.

Embodiment A3a. A composition of Embodiment A3 wherein the ratio of the compound of Formula 1a to the compound of Formula 1a' is greater than 60:40.

Embodiment A3b. A composition of Embodiment A3a wherein the ratio of the compound of Formula 1a to the compound of Formula 1a' is greater than 80:20.

Embodiment A3c. A composition of Embodiment A3a wherein the ratio of the compound of Formula 1a to the compound of Formula 1a' is greater than 90:10.

Embodiment A3d. A composition of Embodiment A3a wherein the ratio of the compound of Formula 1a to the compound of Formula 1a' is greater than 99:1.

Embodiment A4. A composition comprising a compound of Formula 1a' and a compound of Formula 1a.

Embodiment A4a. A composition of Embodiment A4 wherein the ratio of the compound of Formula 1a' to the compound of Formula 1a is greater than 60:40.

Embodiment A4b. A composition of Embodiment A4 wherein the ratio of the compound of Formula 1a' to the compound of Formula 1a is greater than 80:20.

Embodiment A4c. A composition of Embodiment A4 wherein the ratio of the compound of Formula 1a' to the compound of Formula 1a is greater than 90:10.

Embodiment A4d. A composition of Embodiment A4 wherein the ratio of the compound of Formula 1a' to the compound of Formula 1a is greater than 99:1.

Embodiment X. A method for controlling an invertebrate pest comprising contacting the invertebrate pest or its environment with a biologically effective amount of a compound of Formula 1.

Embodiment X1. A method of Embodiment X wherein the invertebrate pest is a member of Hemiptera.

Embodiment X2. A method of Embodiment X1 wherein the member of Hemipteran is a member of the suborder Homoptera.

Embodiment X2a. A method of Embodiment X2 wherein the suborder Homoptera comprises planthoppers from the families Cicadellidae and Delphacidae.

Embodiment X2b. A method of Embodiment X2 wherein the suborder Homoptera comprises aphids from the family Aphididae.

Embodiment X2c. A method of Embodiment X2 wherein the suborder Homoptera comprises whiteflies from the family Aleyrodidae.

Embodiment X3. A method of Embodiment X2 wherein the suborder Homoptera comprises CPH, CMA, GPA and WF.

Embodiment X4. A method of Embodiment X2 wherein the suborder Homoptera comprises *Aphis fabae* Scopoli (black bean aphid), *Aphis gossypii* Glover (cotton aphid or melon aphid), *Bemisia tabaci* Gennadius (tobacco whitefly, sweetpotato whitefly), *Bemisia* argentifolii Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), Macrosteles *quadrilineatus* Forbes (aster leafhopper), *Nephotettix cincticeps* Uhler (green rice leafhopper), *Nephotettix nigropictus* Stil (rice leafhopper), *Nilaparvata lugens* Stil (brown planthopper), *Peregrinus maidis* Ashmead (corn planthopper), *Sogatella furcifera* Horvath (white-backed planthopper), *Tagosodes orizicolus* Muir (rice delphacid), *Typhlocyba pomaria* McAtee (white apple leafhopper) or *Erythroneura* spp. (grape leafhoppers).

Embodiment X5. A method of Embodiment X1 wherein the Hemipteran is a member of the suborder Heteroptera.

Embodiment X5a. A method of Embodiment X5 wherein the suborder Heteroptera comprises *Acrosternum hilare* Say (green stink bug), *Anasa tristis* De Geer (squash bug), *Blissus leucopterus leucopterus* Say (chinch bug), *Cimex lectularius* Llinnaeus (bed bug) *Corythucha gossypii* Fabricius (cotton lace bug), *Cyrtopeltis modesta* Distant (tomato bug), *Dichelops melacanthus* Dallas (green belly Stink bug), *Dysdercus suturellus* Herrich-Schaffer (cotton stainer), *Euschistus heros* Fabricius (Neotropical Brown Stink Bug), *Euschistus servus* Say (brown stink bug), *Euschistus variolarius* Palisot de Beauvois (one-spotted stink bug), Graptostethus spp. (complex of seed bugs), *Halyomorpha halys* Stil (brown marmorated stink bug), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper).

Embodiment X6. A method of Embodiment X5 wherein the suborder Heteroptera comprises stink bugs from the family Pentatomidae.

Embodiment X7. A method of Embodiment X6 wherein the suborder Heteroptera comprises *Acrosternum hilare* Say (green stink bug), *Dichelops melacanthus* Dallas (green belly Stink bug), *Euschistus heros* Fabricius (Neotropical Brown Stink Bug), *Euschistus servus* Say (brown stink bug), *Euschistus variolarius* Palisot de Beauvois (one-spotted stink bug), *Halymorpha halys* Stil (brown marmorated stink bug), *Nezara viridula* Linnaeus (southern green stink bug), *Oebalus pugnax* Fabricius (rice stink bug).

Embodiment X8. A method of Embodiment X5 wherein the suborder Heteroptera comprises *Anasa tristis* De Geer (squash bug), *Blissus leucopterus* Say (chinch bug), *Cimex lectularius* Linnaeus (bed bug), *Corythuca gossypii* Fabricius (cotton lace bug), *Cyrtopeltis modesta* Distant (tomato bug), *Dysdercus suturellus* Herrich-Schaffer (cotton stainer), *Graptosthetus* spp. (complex of seed bugs), *Leptoglossus corculus* Say (leaf-footed pine seed bug), *Lygus lineolaris* Palisot de Beauvois (tarnished plant bug), *Oncopeltus fasciatus* Dallas (large milkweed bug), or *Pseudatomoscelis seriatus* Reuter (cotton fleahopper).

Embodiments of this disclosure, including Embodiments 1-X8 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this disclosure, including Embodiments 1-X8 above as well as any other embodiments described herein, and any combination thereof, pertain to the compositions and methods of the present disclosure.

Combinations of Embodiments 1-X8 are illustrated by:

Embodiment A. A compound of Formula 1 wherein $R^1$ is F;

A is $CR^3$;

$R^2$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^3$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^4$ is a 5- to 6-membered heterocyclic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and $S(=O)_2$, each ring or ring system optionally substituted with up to 5 substituents independently selected from $R^v$, and r is the number of the substituents.

each $R^v$ is independently H, halogen, $C_1$-$C_6$ alkyl, $C_1$-$C_6$ haloalkyl, $C_1$-$C_6$ alkoxy or $C_1$-$C_6$ haloalkoxy;

r is 1, 2, 3, 4 or 5;

$R^5$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy; Q is a six membered aromatic ring with 0 to 2 N on the ring, each ring optionally substituted on carbon atom ring members with up to 5 substituents independently selected from $R^w$;

$R^w$ is independently cyano, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl;

s is 1, 2, 3, 4 or 5;

n is 0, 1 or 2.

Embodiment B. A compound of Embodiment A wherein $R^2$ is H, halogen or $C_1$-$C_4$ alkyl;

$R^3$ is H, halogen, $C_1$-$C_4$ alkyl, $C_1$-$C_4$ haloalkyl, $C_1$-$C_4$ alkoxy or $C_1$-$C_4$ haloalkoxy;

$R^4$ is selected from U-2 to U-49 or U52 to U61 as shown in Exhibit 1;

r is 1 or 2;

$R^5$ is H, halogen, $C_1$-$C_4$ alkyl, $C_1$-$C_4$ haloalkyl, $C_1$-$C_4$ alkoxy or $C_1$-$C_4$ haloalkoxy;

$R^w$ is $C_1$-$C_6$ haloalkoxy, $C_1$-$C_6$ haloalkyl, $C_2$-$C_6$ haloalkenyl, $C_2$-$C_6$ haloalkynyl, $C_1$-$C_6$ haloalkylthio, $C_1$-$C_6$ haloalkylsulfinyl, $C_1$-$C_6$ haloalkylsulfonyl.

s is 1 or 2.

Embodiment C. A compound of Embodiment B wherein $R^2$ is H;

$R^3$ is H or halogen;

$R^4$ is selected from U-2 to U-49;

$R^v$ is H;

$R^5$ is H or halogen;

Q is a phenyl, pyridinyl, pyrimidinyl or pyrazinyl ring, each ring optionally substituted on carbon atom ring members with up to 5 substituents independently selected from $R^w$;

$R^w$ is $OCF_3$, $SCF_3$, $CF_3$, $SOCF_3$ or $SO_2CF_3$.

Embodiment D. A compound of Embodiment B wherein $R^2$ is H;

$R^3$ is H or halogen;

$R^4$ is selected from U-2 to U-49;

$R^v$ is $C_1$-$C_6$ alkyl;

$R^5$ is H;

Q is a phenyl, pyridinyl, pyrimidinyl or pyrazinyl ring, each ring optionally substituted on carbon atom ring members with up to 5 substituents independently selected from $R^w$;

Embodiment E. A compound of Embodiment C wherein $R^3$ is halogen;

$R^4$ is selected from U-2, U-3, U-4, U-5, U-7, U-9, U-11, U-12, U-13, U-16, U-21, U-25, U-26, U-27, U-28, U-29, U-31, U-32, U-35, U-36, U-37, U-44, U-48 and U-49;

$R^5$ is H;

Q is a phenyl, pyridinyl, pyrimidinyl or pyrazinyl ring, each ring optionally substituted on carbon atom ring members with up to 5 substituents independently selected from $R^w$.

Embodiment F. A compound of Embodiment E wherein $R^3$ is F;

$R^4$ is selected from U-9, U-11, U-32, U-36 and U-44;

Q is a phenyl ring optionally substituted on carbon atom ring members with up to 5 substituents independently selected from $R^w$.

Embodiment G. A compound of Embodiment F wherein $R^4$ is selected from U-9 and U-44.

Embodiment H. A compound of Embodiment G wherein $R^4$ is selected from the group of U-9.

Embodiment I. A compound of Embodiment G wherein $R^4$ is selected from the group of U-44.

Embodiment J. A compound of Embodiment B wherein $R^2$ is $C_1$-$C_4$ alkyl;

$R^3$ is H or halogen;

$R^4$ is selected from U-2 to U-49;

$R^v$ is H;

r is 2;

$R^5$ is H;

Q is a phenyl, pyridinyl, pyrimidinyl or pyrazinyl ring, each ring optionally substituted on carbon atom ring members with up to 5 substituents independently selected from $R^w$;

$R^w$ is $OCF_3$, $SCF_3$, $CF_3$, $SOCF_3$ or $SO_2CF_3$.

Embodiment AA. A compound of Formula 1 wherein $R^1$ is $OR^6$;

A is $CR^3$;

$R^2$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^3$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^4$ is a 5- to 6-membered heterocyclic ring, each ring containing ring members selected from carbon atoms and 1 to 4 heteroatoms independently selected from up to 2 O, up to 2 S and up to 4 N atoms, wherein up to 2 ring members are independently selected from C(═O), C(═S), S(═O) and $S(═O)_2$, each ring or ring system optionally substituted with up to 5 substituents independently selected from $R^v$, and r is the number of the substituents.

each $R^v$ is independently H, halogen, $C_1$-$C_6$ alkyl, $C_1$-$C_6$ haloalkyl, $C_1$-$C_6$ alkoxy or $C_1$-$C_6$ haloalkoxy;

r is 1, 2, 3, 4 or 5;

$R^5$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^6$ is $C_1$-$C_4$ alkyl;

Q is a six membered aromatic ring with 0 to 2 N on the ring, each ring optionally substituted on carbon atom ring members with up to 5 substituents independently selected from $R^w$;

$R^w$ is independently cyano, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl;

s is 1, 2, 3, 4 or 5;

n is 0, 1 or 2.

Embodiment BB. A compound of Embodiment AA wherein $R^2$ is H, halogen or $C_1$-$C_4$ alkyl;

$R^3$ is H, halogen, $C_1$-$C_4$ alkyl, $C_1$-$C_4$ haloalkyl, $C_1$-$C_4$ alkoxy or $C_1$-$C_4$ haloalkoxy;

$R^4$ is selected from U-2 to U-49 or U52 to U61 as shown in Exhibit 1;

r is 1 or 2;

$R^5$ is H, halogen, $C_1$-$C_4$ alkyl, $C_1$-$C_4$ haloalkyl, $C_1$-$C_4$ alkoxy or $C_1$-$C_4$ haloalkoxy;

$R^6$ is Me;

$R^w$ is $C_1$-$C_6$ haloalkoxy, $C_1$-$C_6$ haloalkyl, $C_2$-$C_6$ haloalkenyl, $C_2$-$C_6$ haloalkynyl, $C_1$-$C_6$ haloalkylthio, $C_1$-$C_6$ haloalkylsulfinyl, $C_1$-$C_6$ haloalkylsulfonyl.

s is 1 or 2.

Embodiment CC. A compound of Embodiment BB wherein $R^2$ is H;

$R^3$ is H or halogen;

$R^4$ is selected from U-2 to U-49;

$R^v$ is H;

r is 2;

$R^5$ is H or halogen;

Q is a phenyl, pyridinyl, pyrimidinyl or pyrazinyl ring, each ring optionally substituted on carbon atom ring members with up to 5 substituents independently selected from $R^w$; $R^w$ is $OCF_3$, $SCF_3$, $CF_3$, $SOCF_3$ or $SO_2CF_3$.

Embodiment DD. A compound of Embodiment BB wherein $R^2$ is H;

$R^3$ is H or halogen;

$R^4$ is selected from U-2 to U-49;

$R^v$ is $C_1$-$C_6$ alkyl;

$R^5$ is H;

Q is a phenyl, pyridinyl, pyrimidinyl or pyrazinyl ring, each ring optionally substituted on carbon atom ring members with up to 5 substituents independently selected from $R^w$.

Embodiment EE. A compound of Embodiment CC wherein $R^3$ is halogen;

$R^4$ is selected from U-2, U-3, U-4, U-5, U-7, U-9, U-11, U-12, U-13, U-16, U-21, U-25, U-26, U-27, U-28, U-29, U-31, U-32, U-35, U-36, U-37, U-44, U-48 and U-49;

$R^5$ is H;

Q is a phenyl, pyridinyl, pyrimidinyl or pyrazinyl ring, each ring optionally substituted on carbon atom ring members with up to 5 substituents independently selected from $R^w$.

Embodiment FF. A compound of Embodiment EE wherein $R^3$ is F;

$R^4$ is selected from U-9 and U-44;

Q is a phenyl ring optionally substituted on carbon atom ring members with up to 5 substituents independently selected from $R^w$.

Embodiment GG. A compound of Embodiment FF wherein $R^4$ is selected from the group of U-9.

Embodiment HH. A compound of Embodiment FF wherein $R^4$ is selected from the group of U-44.

Embodiment AAA. A compound of Formula 1 wherein $R^1$ is $SR^6$;

A is $CR^3$;

$R^2$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^3$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^4$ is a 5- to 6-membered heterocyclic ring, each ring containing ring members selected from carbon atoms and 1 to 4 heteroatoms independently selected from up to 2 O, up to 2 S and up to 4 N atoms, wherein up to 2 ring members are independently selected from C(═O), C(═S), S(═O) and $S(═O)_2$, each ring or ring system optionally substituted with up to 5 substituents independently selected from $R^v$, and r is the number of the substituents.

each $R^v$ is independently H, halogen, $C_1$-$C_6$ alkyl, $C_1$-$C_6$ haloalkyl, $C_1$-$C_6$ alkoxy or $C_1$-$C_6$ haloalkoxy;

r is 1, 2, 3, 4 or 5;

$R^5$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^6$ is $C_1$-$C_4$ alkyl;

Q is a six membered aromatic ring with 0 to 2 N on the ring, each ring optionally substituted on carbon atom ring members with up to 5 substituents independently selected from $R^w$;

$R^w$ is independently cyano, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl;

s is 1, 2, 3, 4 or 5;

n is 0, 1 or 2.

Embodiment BBB. A compound of Embodiment AAA wherein $R^2$ is H, halogen or $C_1$-$C_4$ alkyl;

$R^3$ is H, halogen, $C_1$-$C_4$ alkyl, $C_1$-$C_4$ haloalkyl, $C_1$-$C_4$ alkoxy or $C_1$-$C_4$ haloalkoxy;

$R^4$ is selected from U-2 to U-49 or U52 to U61 as shown in Exhibit 1;

r is 1 or 2;

$R^5$ is H, halogen, $C_1$-$C_4$ alkyl, $C_1$-$C_4$ haloalkyl, $C_1$-$C_4$ alkoxy or $C_1$-$C_4$ haloalkoxy;

$R^6$ is Me;

$R^w$ is $C_1$-$C_6$ haloalkoxy, $C_1$-$C_6$ haloalkyl, $C_2$-$C_6$ haloalkenyl, $C_2$-$C_6$ haloalkynyl, $C_1$-$C_6$ haloalkylthio, $C_1$-$C_6$ haloalkylsulfinyl, $C_1$-$C_6$ haloalkylsulfonyl.

s is 1 or 2.

Embodiment CCC. A compound of Embodiment BBB wherein $R^2$ is H;

$R^3$ is H or halogen;

$R^4$ is selected from U-2 to U-49;

$R^v$ is H;

r is 2;

$R^5$ is H;

Q is a phenyl, pyridinyl, pyrimidinyl or pyrazinyl ring, each ring optionally substituted on carbon atom ring members with up to 5 substituents independently selected from $R^w$;

$R^w$ is $OCF_3$, $SCF_3$, $CF_3$, $SOCF_3$ or $SO_2CF_3$.

Embodiment DDD. A compound of Embodiment BBB wherein $R^2$ is H;

$R^3$ is H or halogen;

$R^4$ is selected from U-2 to U-49;

$R^v$ is $C_1$-$C_6$ alkyl;

$R^5$ is H;

Q is a phenyl, pyridinyl, pyrimidinyl or pyrazinyl ring, each ring optionally substituted on carbon atom ring members with up to 5 substituents independently selected from $R^w$;

Embodiment EEE. A compound of Embodiment CCC wherein $R^3$ is halogen;

$R^4$ is selected from U-2, U-3, U-4, U-5, U-7, U-9, U-11, U-12, U-13, U-16, U-21, U-25, U-26, U-27, U-28, U-29, U-31, U-32, U-35, U-36, U-37, U-44, U-48 and U-49;

$R^5$ is H;

Q is a phenyl, pyridinyl, pyrimidinyl or pyrazinyl ring, each ring optionally substituted on carbon atom ring members with up to 5 substituents independently selected from $R^w$.

Embodiment FFF. A compound of Embodiment EEE wherein $R^3$ is F;

$R^4$ is selected from U-9 and U-44;

Q is a phenyl ring optionally substituted on carbon atom ring members with up to 5 substituents independently selected from $R^w$.

Embodiment GGG. A compound of Embodiment FFF wherein $R^4$ is selected from the group of U-9.

Embodiment HHH. A compound of Embodiment FFF wherein $R^4$ is selected from the group of U-44.

Specific embodiments include compounds of Formula 1 selected from the group consisting of:

3-Fluoro-4-[fluoro[4-(trifluoromethoxy)phenyl]methyl]-5-(2H-1,2,3-triazol-2-yl)pyridine;

3-Chloro-4-[fluoro[4-(trifluoromethoxy)phenyl]methyl]-5-(2H-1,2,3-triazol-2-yl)pyridine;

3-Fluoro-4-[methoxy[4-(trifluoromethoxy)phenyl]methyl]-5-(2H-1,2,3-triazol-2-yl)pyridine;

3-Fluoro-4-[fluoro[4-[(trifluoromethyl)thio]phenyl]methyl]-5-(2-oxazolyl)pyridine;

3-Fluoro-4-[fluoro[4-[(trifluoromethyl)thio]phenyl]methyl]-5-(2H-1,2,3-triazol-2-yl)pyridine;

3-Chloro-4-[fluoro[4-[(trifluoromethyl)thio]phenyl]methyl]-5-(2H-1,2,3-triazol-2-yl)pyridine;

3-Fluoro-4-[fluoro[4-(trifluoromethyl)phenyl]methyl]-5-(2H-1,2,3-triazol-2-yl)pyridine;

3-Fluoro-4-[fluoro[4-(trifluoromethoxy)phenyl]methyl]-5-(2-oxazolyl)pyridine;

3-Fluoro-4-[fluoro[4-[(trifluoromethyl)sulfinyl]phenyl]methyl]-5-(2H-1,2,3-triazol-2-yl)pyridine;

3-Fluoro-4-[fluoro[4-(trifluoromethoxy)phenyl]methyl]-5-(5-oxazolyl)pyridine;

3-Fluoro-4-[fluoro[4-(trifluoromethoxy)phenyl]methyl]-5-(3-methyl-1,2,4-oxadiazol-5-yl)pyridine;

3-Fluoro-4-[methoxy[4-(trifluoromethoxy)phenyl]methyl]-5-(2H-1,2,3-triazol-2-yl)pyridine;

3-Chloro-4-[methoxy[4-(trifluoromethoxy)phenyl]methyl]-5-(2H-1,2,3-triazol-2-yl)pyridine;

3-Bromo-4-[fluoro[4-[(trifluoromethyl)thio]phenyl]methyl]-5-(2H-1,2,3-triazol-2-yl)pyridine; and 3-Fluoro-4-[methoxy[4-[(trifluoromethyl)thio]phenyl]methyl]-5-(1,2,4-oxadiazol-3-yl)pyridine.

More specific embodiments include compounds of Formula 1 selected from the group consisting of:

3-Fluoro-4-[fluoro[4-(trifluoromethoxy)phenyl]methyl]-5-(2H-1,2,3-triazol-2-yl)pyridine 3-Chloro-4-[fluoro[4-(trifluoromethoxy)phenyl]methyl]-5-(2H-1,2,3-triazol-2-yl)pyridine 3-Fluoro-4-[methoxy[4-(trifluoromethoxy)phenyl]methyl]-5-(2H-1,2,3-triazol-2-yl)pyridine 3-Fluoro-4-[fluoro[4-[(trifluoromethyl)thio]phenyl]methyl]-5-(2-oxazolyl)pyridine 3-Fluoro-4-[fluoro[4-[(trifluoromethyl)thio]phenyl]methyl]-5-(2H-1,2,3-triazol-2-yl)pyridine 3-Bromo-4-[fluoro[4-[(trifluoromethyl)thio]phenyl]methyl]-5-(2H-1,2,3-triazol-2-yl)pyridine More specific embodiments include compounds of Formula 1 selected from the group consisting of:

3-Fluoro-4-[fluoro[4-(trifluoromethoxy)phenyl]methyl]-5-(2H-1,2,3-triazol-2-yl)pyridine;

3-Chloro-4-[fluoro[4-(trifluoromethoxy)phenyl]methyl]-5-(2H-1,2,3-triazol-2-yl)pyridine;

3-Chloro-4-[fluoro[4-[(trifluoromethyl)thio]phenyl]methyl]-5-(2H-1,2,3-triazol-2-yl)pyridine;

3-Fluoro-4-[methoxy[4-(trifluoromethoxy)phenyl]methyl]-5-(2H-1,2,3-triazol-2-yl)pyridine;

3-Fluoro-4-[fluoro[4-[(trifluoromethyl)thio]phenyl]methyl]-5-(2-oxazolyl)pyridine;

3-Fluoro-4-[fluoro[4-[(trifluoromethyl)thio]phenyl]methyl]-5-(2H-1,2,3-triazol-2-yl)pyridine;

3-Bromo-4-[fluoro[4-[(trifluoromethyl)thio]phenyl]methyl]-5-(2H-1,2,3-triazol-2-yl)pyridine.

More specific embodiments include compounds of Formula 1 selected from the group consisting of:

3-Fluoro-4-[fluoro[4-(trifluoromethyl)phenyl]methyl]-5-(2H-1,2,3-triazol-2-yl)pyridine;

3-Fluoro-4-[fluoro[4-(trifluoromethoxy)phenyl]methyl]-5-(2-oxazolyl)pyridine;

3-Fluoro-4-[fluoro[4-[(trifluoromethyl)sulfinyl]phenyl]methyl]-5-(2H-1,2,3-triazol-2-yl)pyridine;

3-Fluoro-4-[fluoro[4-(trifluoromethoxy)phenyl]methyl]-5-(5-oxazolyl)pyridine;

3-Fluoro-4-[fluoro[4-(trifluoromethoxy)phenyl]methyl]-5-(3-methyl-1,2,4-oxadiazol-5-yl)pyridine;

3-Chloro-4-[methoxy[4-(trifluoromethoxy)phenyl]methyl]-5-(2H-1,2,3-triazol-2-yl)pyridine; and 3-Fluoro-4-[methoxy[4-[(trifluoromethyl)thio]phenyl]methyl]-5-(1,2,4-oxadiazol-3-yl)pyridine. 3-Fluoro-4-[methoxy[4-(trifluoromethoxy)phenyl]methyl]-5-(2H-1,2,3-triazol-2-yl)pyridine;

Embodiment Y1. A composition comprising a compound of Formula 1 or any one of the preceding embodiments and at least one additional component selected from the group consisting of surfactants, solid diluents and liquid diluents, said composition optionally further comprising at least one additional biologically active compound or agent.

Embodiment Y2. The composition of embodiment Y1 wherein the at least one additional biologically active compound or agent is selected from the group consisting of abamectin, acephate, acequinocyl, acetamiprid, acrinathrin, afidopyropen, amidoflumet, amitraz, avermectin, azadirachtin, azinphos-methyl, benfuracarb, bensultap, bifenthrin, bifenazate, bistrifluron, borate, bromantraniliprole, buprofezin, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyclaniliprole, cycloprothrin, cycloxaprid, cyflumetofen, cyfluthrin, beta-cyfluthrin, cyhalodiamide, cyhalothrin, gamma-cyhalothrin, lambda-cyhalothrin, cypermethrin, alpha-cypermethrin, zeta-cypermethrin, cyromazine, deltamethrin, diafenthiuron, diazinon, dichlorantraniliprole, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin, flonicamid, flubendiamide, flucythrinate, flufenerim, flufenoxuron, flufenoxystrobin, fluensulfone, fluopyram, flupyradifurone, fluvalinate, tau-fluvalinate, fonophos, formetanate, fosthiazate, halofenozide, heptafluthrin, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiocarb, methomyl, methoprene, methoxychlor, methoxyfenozide, metofluthrin, monocrotophos, monofluorothrin, nicotine, N-[1,1-dimethyl-2-(methylthio)ethyl]-7-fluoro-2-(3-pyridinyl)-2H-indazole-4-carboxamide, N-[1,1-dimethyl-2-(methylsulfinyl)ethyl]-7-fluoro-2-(3-pyridinyl)-2H-indazole-4-carboxamide, N-[1,1-dimethyl-2-(methylsulfonyl)ethyl]-7-fluoro-2-(3-pyridinyl)-2H-indazole-4-carboxamide, N-(1-methylcyclopropyl)-2-(3-pyridinyl-2H-indazole-1-carboxamide, N-[1-(difluoromethyl)cyclopropyl]-2-(3-pyridinyl)-2H-indazole-4-carboxamide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide, pymetrozine, pyrafluprole, pyrethrin, pyridaben, pyridalyl, pyrifluquinazon, pyriminostrobin, pyriprole, pyriproxyfen, rotenone, ryanodine, silafluofen, spinetoram, spinosad, spirodiclofen, spiromesifen, spirotetramat, sulprofos, sulfoxaflor, tebufenozide, tebufenpyrad, teflubenzuron, tefluthrin, tetrachlorantraniliprole, tetrachlorvinphos, tetramethrin, tetramethylfluthrin, thiacloprid, thiamethoxam, thiodicarb, thiosultap-sodium, tioxazafen, tolfenpyrad, tralomethrin, triazamate, trichlorfon, triflumezopyrim, triflumuron, *Bacillus thuringiensis* delta-endotoxins, entomopathogenic bacteria, entomopathogenic viruses and entomopathogenic fungi.

Embodiment Y3. The composition of embodiment Y2 wherein the at least one additional biologically active compound or agent is selected from the group consisting of abamectin, acetamiprid, acrinathrin, afidopyropen, amitraz, avermectin, azadirachtin, benfuracarb, bensultap, bifenthrin, buprofezin, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, fluensulfone, flupiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, metofluthrin, monofluorothrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumezopyrim, triflumuron, *Bacillus thuringiensis* delta-endotoxins, all strains of *Bacillus thuringiensis* and all strains of nuclear polyhedrosis viruses.

Embodiment Y4. The composition of any one of embodiments Y1-Y3 further comprising a liquid fertilizer.

Embodiment Y5. The composition of Embodiment Y4 wherein the liquid fertilizer is aqueous-based.

Embodiment Y6. A soil drench formulation comprising the composition of any one of embodiments Y1-Y3.

Embodiment Y7. A spray composition comprising the composition of any one of embodiments Y1-Y3 and a propellant.

Embodiment Y8. A bait composition, comprising the composition of any one of embodiments Y1-Y3, one or more food materials, optionally an attractant, and optionally a humectant.

Embodiment Y9. A trap device for controlling an invertebrate pest, comprising: the bait composition of Embodiment Y8 and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiment Y10. A composition comprising the composition of any of Embodiments Y1-Y3 wherein the composition is a solid composition selected from dusts, powders, granules, pellets, prills, pastilles, tablets, and filled films.

Embodiment Y11. The composition of Embodiment Y10 wherein the composition is water-dispersible or water-soluble.

Embodiment Y12. A liquid or dry formulation comprising the composition of any one of Embodiments Y1-Y3 for use in a drip irrigation system, furrow during planting, handheld sprayer, backpack sprayer, boom sprayer, ground sprayer, aerial application, unmanned aerial vehicle, or a seed treatment.

Embodiment Y13. The liquid or dry formulation of Embodiment Y12 wherein said formulation is sprayed at an ultra-low volume.

Of note is that compounds of this disclosure are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the disclosure. Compounds of this disclosure because of their favorable translocation properties or systemicity in plants also protect foliar or other plant parts which are not directly contacted with a compound of Formula 1 or a composition comprising the compound.

Also noteworthy as embodiments of the present disclosure are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present disclosure are compositions for controlling an invertebrate pest comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent. Embodiments of the disclosure further include methods for controlling an invertebrate pest comprising contacting the invertebrate pest or its environment with a biologically effective amount of a compound of any of the preceding Embodiments (e.g., as a composition described herein).

Embodiments of the disclosure also include a composition comprising a compound of any of the preceding Embodiments, in the form of a soil drench liquid formulation. Embodiments of the disclosure further include methods for controlling an invertebrate pest comprising contacting the soil with a liquid composition as a soil drench comprising a biologically effective amount of a compound of any of the preceding Embodiments.

Embodiments of the disclosure also include a spray composition for controlling an invertebrate pest comprising a biologically effective amount of a compound of any of the preceding Embodiments and a propellant. Embodiments of the disclosure further include a bait composition for controlling an invertebrate pest comprising a biologically effective amount of a compound of any of the preceding Embodiments, one or more food materials, optionally an attractant, and optionally a humectant. Embodiments of the disclosure also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the disclosure also include methods for protecting a seed from an invertebrate pest comprising contacting the seed with a biologically effective amount of a compound of any of the preceding Embodiments.

Embodiments of the disclosure also include methods for protecting an animal from an invertebrate parasitic pest comprising administering to the animal a parasiticidally effective amount of a compound of any of the preceding Embodiments.

Embodiments of the disclosure also include methods for controlling an invertebrate pest comprising contacting the invertebrate pest or its environment with a biologically effective amount of a compound of Formula 1, an N-oxide or a salt thereof, (e.g., as a composition described herein), provided that the methods are not methods of medical treatment of a human or animal body by therapy.

This disclosure also relates to such methods wherein the invertebrate pest or its environment is contacted with a composition comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

One or more of the following methods and variations as described in Schemes 1-11 can be used to prepare the compounds of Formula 1. The definitions of $R^1$, $R^2$, $R^3$, $R^4$, $R^5$, A and Q in the compounds of Formulae 1-18 below are as defined above in the Summary of the Disclosure unless otherwise noted. Compounds of Formulae 1a-1d are various subsets of the compounds of Formula 1, and all substituents for Formulae 1a-1d are as defined above for Formula 1 unless otherwise indicated. Ambient or room temperature is defined as about 20-25° C.

As shown in Scheme 1, compounds of Formula 1a (compounds of Formula 1 wherein $R^4$ is attached to the rest of the molecule through a carbon atom) can be prepared by contacting compounds of Formula 2a wherein X is Cl, Br or I with boronic acids or organotin compounds of Formula 3 in the presence of a palladium catalyst. A wide variety of palladium-containing compounds and complexes are useful as catalysts for the present method. Examples of palladium-containing compounds and complexes useful as catalysts in the method of Scheme 1 include $Pd(OAc)_2$ (palladium(II) acetate), $PdCl_2$ (palladium(II) chloride), $PdCl_2(PPh_3)_2$ bis (triphenylphosphine)palladium(II) dichloride, $Pd(PPh_3)_4$ (tetrakis(triphenylphosphine)palladium(0), $Pd(C_5H_7O_2)_2$ (palladium(II) acetylacetonate) and $Pd_2(dba)_3$ tris (dibenzylideneacetone)dipalladium(0). Also as shown in Scheme 1, compounds of Formula 1b (compounds of Formula 1 wherein $R^4$ is attached to the rest of the molecule through a nitrogen atom) can be prepared by contacting compounds of Formula 2a (wherein X is Cl, Br or I) with compounds of Formula 4 (a heterocyclic compound with an NH as a ring member wherein the H can be replaced by another functional group during a chemical reaction) in the presence of a copper catalyst or a palladium catalyst. For recent review articles and books about this type of functional group transformation; see, for example, F. Bellina et al., *Synthesis* 2004, 15, 2419-2440; P. Espinet and A. M. Echavarren, *Angewandte Chemie, International Edition* 2004, 43, 4704-4734; and J. J. Li, G. W. Gribble, editors, Palladium in Heterocyclic Chemistry: A Guide for the Synthetic Chemist.

2000. K. W. Anderson et al., *Angewandte Chemie, International Edition* 2006, 45, 6523-6527.

Scheme 1

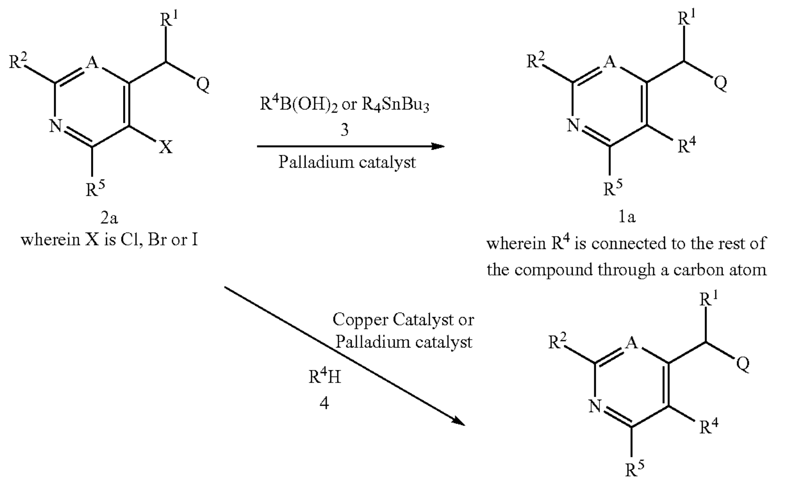

2a
wherein X is Cl, Br or I 1a
wherein $R^4$ is connected to the rest of the compound through a carbon atom 1b
wherein $R^4$ is connected to the rest of the compound through a nitrogen atom As shown in Scheme 2, compounds of Formula 1b can also be prepared by contacting compounds of Formula 2b (wherein X is F or Cl) with compounds of Formula 4 in the presence of a base, such as $K_2CO_3$ or $Cs_2CO_3$. A wide variety of known general procedures are reasonably believed to be readily adaptable by one skilled in the art to the method of Scheme 2, for example, see, J. D. Culshaw et al., *Synlett* 2012, 23, 1816-1820. The method of Scheme 2 is illustrated by Synthesis Example 1, Step C.

Scheme 2

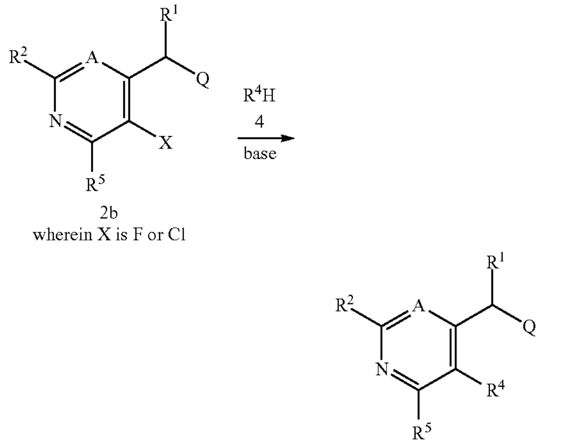

2b
wherein X is F or Cl 1b
wherein $R^4$ is connected to the rest of the compound through a nitrogen atom Alternatively, as shown in Scheme 3, compounds of Formula 1a can be prepared by constructing a heterocyclic ring via compounds of Formula 5 wherein $R^{10}$ is CN, $COCH_3$, or CHO. The methods to form a heterocyclic ring through these functional groups are known in the literature. A variety of known general procedures are reasonably believed to be readily adaptable by one skilled in the art to the method of Scheme 3, for example, see, World Patent Publication WO 2012/002577; World Patent Publication WO 2012/087938; M. H. Gezginci et al.; *J. Med. Chem.* 2001, 44, 1560-1563; K. Gobbis, *J. Heterocyclic Chem.* 2009, 46, 1271-1279. The method of Scheme 3 is illustrated by synthesis Example 2, Step D.

Scheme 3

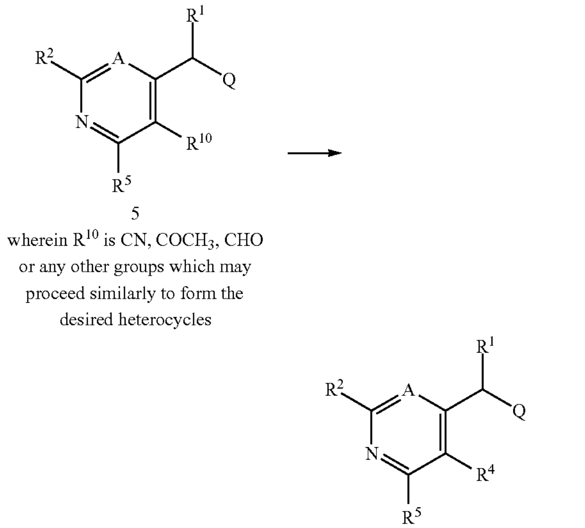

5
wherein $R^{10}$ is CN, $COCH_3$, CHO or any other groups which may proceed similarly to form the desired heterocycles 1a
wherein $R^4$ is connected to the rest of the compound through a carbon atom As shown in Scheme 4, a compound of Formula 5 can be prepared by converting the X group in a compound of Formula 6 to the $R^{10}$ group in a compound of Formula 5 via functional group transformation reactions. A variety of general procedures are well known in the literature, for example, see, M. Hatsuda, M. Seki, *Tetrahedron,* 2005, 61, 9908-9917; D. Xu et al., *Tetrahedron* Letters, 2008, 6104-6107; A. Brennfuehrer, et al., *Tetrahedron,* 2007, 63, 6252-6258. The method of Scheme 4 is illustrated by synthesis Example 2, Step C.

Scheme 4

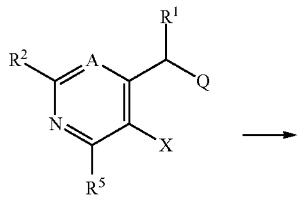

6
wherein X is Br or I

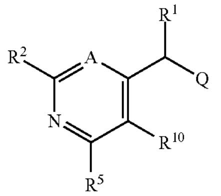

5
wherein $R^{10}$ is CN, $COCH_3$, CHO or any other groups which may proceed similarly to form the desired heterocycles As shown in Scheme 5, compounds of Formula 6 can be prepared by contacting the corresponding alcohols of Formula 7 with fluorination reagents such as (diethylamino) sulfur trifluoride (DAST) or bis(2-methoxyethyl)aminosulfur trifluoride (Deoxo-Fluor) in haloalkane solvents, such as dichloromethane or chloroform from −78° C. to room temperature. A general procedure is known in the art, for example, see, Lal, G. S. et al. *J. Org. Chem.* 1999, 64, 7048. The method of Scheme 5 is illustrated by synthesis Example 1, Step B.

Scheme 5

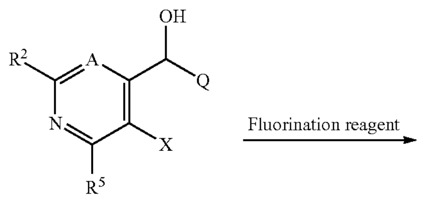

7

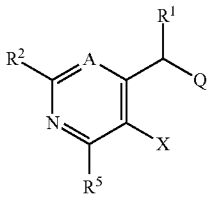

wherein $R^1$ is F
6

As shown in Scheme 6, compounds of Formula 1c (wherein $R^1$ is $OR^6$) can be prepared by reacting corresponding alcohols of Formula 7 with compounds of Formula 8 of $R^6Br$ or $R^6I$ in the presence of a base. Compounds of Formula 1d (wherein $R^1$ is $SR^6$) can be prepared by converting corresponding alcohols of Formula 7 to their corresponding chloride compounds using $SOCl_2$, followed by reacting the chloride compounds with thiol compounds of Formula 9 of $R^6SH$. This method is well known in the literature, for example, see, Qingzhong Hu et al. *J. Med. Chem.* 2010, 53, 5749; World Patent Publication WO 2009/034976. The method of Scheme 6 is illustrated by synthesis Example 2, Step B.

Scheme 6

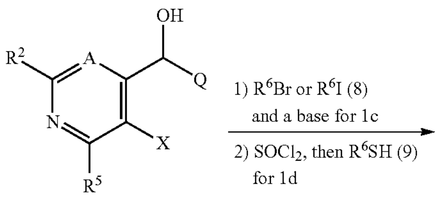

7

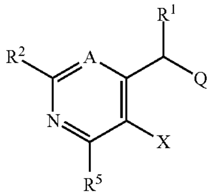

1c or 1d
1c wherein $R_1$ is $OR_6$
1d wherein $R_1$ is $SR_6$

As shown in Scheme 7, compounds of Formula 7 are readily available from nucleophilic addition of compounds of Formula 11 with the aldehydes of Formula 10. The nucleophiles of Formula 11 can be generated by various chemical approaches. For example, the metal-halogen exchange reaction of a haloaromatic compound QX' (wherein X' is preferred to be Br or I) with n-butyllithium or i-propylmagnesium bromide, typically at a temperature between about −100 and about −20° C., can generate the nucleophiles of Formula 11 in situ. A wide variety of general procedures for conducting metal halogen exchange followed by reaction with electrophiles are known in the art and can be readily adapted for the present method. For related general procedures see, for example, M. Schlosser, *Angew. Chem. Int. Ed.* 2004, 43, 2 and P. Knochel et al., *Synthesis,* 2002, 565. In addition, the nucleophiles of Formula 11 can be prepared via Grignard reaction of the corresponding bromide or iodide QBr or QI with magnesium. Some of the nucleophiles of Formula 11 are commercially available, for example, 4-tert-butylphenylmagnesium bromide or 4-(trifluoromethoxy)phenylmagnesium bromide. Most of the aldehydes of Formula 10 are commercially available or known compounds in the chemical literature.

Scheme 7

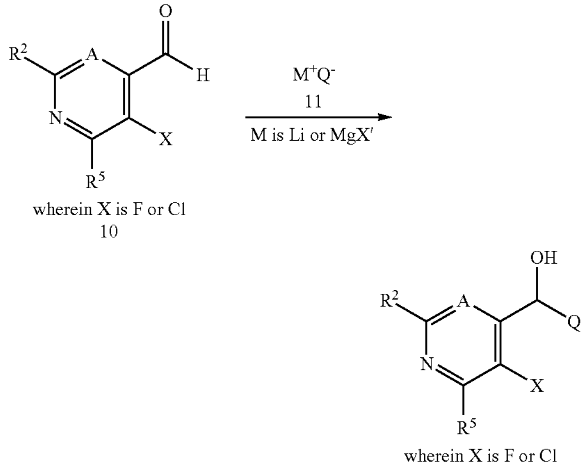

wherein X is F or Cl
10 wherein X is F or Cl
7

As shown in Scheme 8, treating compounds of Formula 12 (wherein X is F or Cl) with a base, such as lithium diisopropylamide, 2,2,6,6-tetramethylpiperidinyl magnesium chloride lithium chloride complex etc. in ether solvents, such as THF, diethyl ether or dioxanes at a temperature between −100° C. to −10° C. will generate the desired anions in situ. By quenching the above anions with aldehydes of Formula 13, compounds of Formula 7 can be prepared. This method is well known in literature, see for example, R. J. Mattson, et al. *J. Org. Chem.,* 1990, 55, 3410. The method of Scheme 8 is illustrated by synthesis Examples 1 and 2, Step A.

Scheme 8

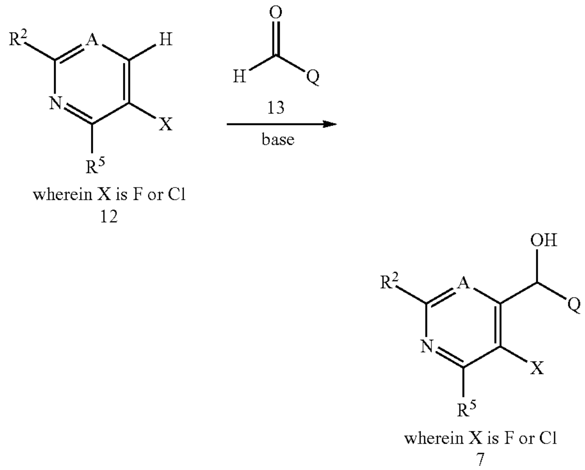

wherein X is F or Cl
12 wherein X is F or Cl
7

As shown in Scheme 9, compounds of Formula 7 can also be prepared by reduction of the corresponding carbonyl compounds of Formula 14. By treating compounds of Formula 14 in solvents, such as methanol, ethanol or ethers (such as tetrahydrofuran) with a variety of reducing agents, such as sodium borohydride, borane-dimethylsulfide, compounds of Formula 7 can be prepared. Alternatively, the reduction of the carbonyl compounds of Formula 14 can be accomplished by catalytic hydrogenation. Several general procedures of these transformations are known in the art; see, for example, D. Douglas, et al., *J. Med. Chem* 2009, 52, 4694; M. Moriyasu, et al., *Synlett* 1997, 3, 273.

Scheme 9

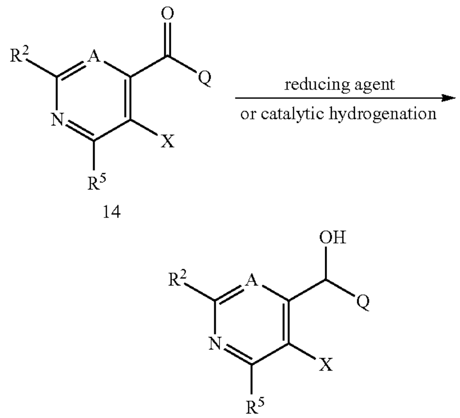

14

7

As shown in Scheme 10, compounds of Formula 14 can be prepared from CN substituted aromatic compounds of Formula 15a (wherein Y is CN) or Weinreb amides of Formula 15b (wherein Y is CONMeOMe). Reactions of compounds of Formula 16 with compounds of Formula 15a or 15b can provide carbonyl compounds of Formula 14. Compounds of Formula 16 can be prepared using a similar chemistry which generates the corresponding anions in situ as described in Scheme 8. For related references see, for example: U.S. Patent Application Publication US 2008/280891 and Bela. et al. European J. Org. Chem. 2004 17, 3623-3632. Many of the compounds of Formula 17 and 15 are commercially available or readily available from literature synthetic methods.

Scheme 10

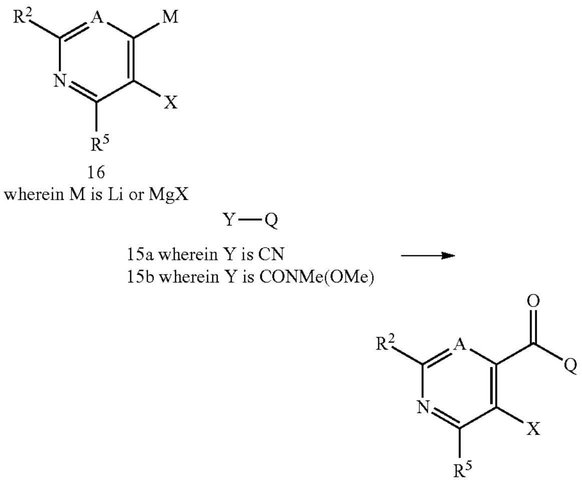

16
wherein M is Li or MgX

Y—Q 15a wherein Y is CN
15b wherein Y is CONMe(OMe)

14

Alternatively, as shown in Scheme 11, compounds of Formula 14 can also be prepared from 4-halopyridine or pyrimidine compounds of Formula 17 (wherein Z is Br or I and X is other than Br or I). The palladium-catalyzed cross-coupling reaction of the compounds of Formula 17, carbon monoxide and boronic acids of Formula 18 can provide an alternative way to prepare compounds of Formula 14. Treating a mixture of 4-halopyridine or pyrimidine compounds of Formula 17 and boronic acids of Formula 18 in the presence of palladium catalyst (such as bis(triphenylphosphine)palladium(II) dichloride, or tetrakis(triphenylphosphine)-palladium(0)) with a base (such as potassium carbonate, sodium carbonate or cesium carbonate) at a temperature of about 80 to 150° C. in ethereal solvents (such as tetrahydrofuran or dioxane) under pressurized carbon monoxide atmosphere from 1 to 50 bar will provide the desired carbonyl compounds of Formula 14. A detailed experimental procedure is given in Couve-Bonnair et. al., *Tetrahedron* Lett. 2001, 42, 3689-3691. Most of the compounds of Formula 17 and boronic acids of Formula 18 are commercially available or readily available from the chemical literature.

Scheme 11

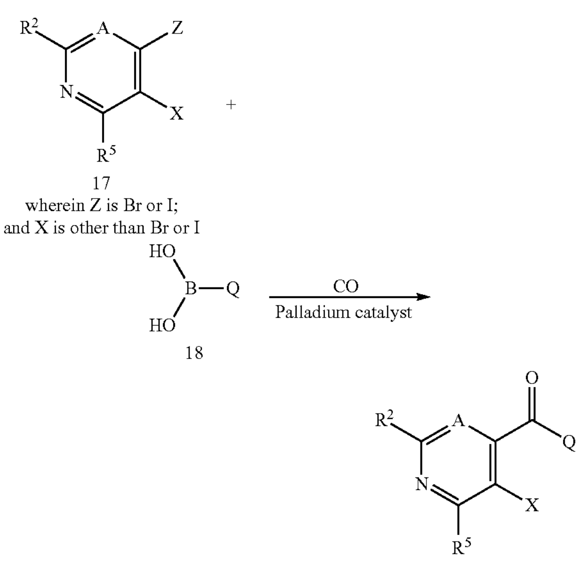

17
wherein Z is Br or I;
and X is other than Br or I

18

14

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present disclosure to its fullest extent. The following *Synthesis* Examples are, therefore, to be construed as merely illustrative, and not limiting of the disclosure in any way whatsoever. Steps in the following *Synthesis* Examples illustrate a procedure for each step in an overall synthetic transformation, and the starting material for each step may not have necessarily been prepared by a particular preparative run whose procedure is described in other Examples or Steps. Ambient or room temperature is defined as about 20-25° C. Percentages are by weight except for chromatographic solvent mixtures or where otherwise indicated. Parts and percentages for chromatographic solvent mixtures are by volume unless otherwise indicated. MPLC refers to medium pressure liquid chromatography on silica gel. $^1$H NMR spectra are reported in ppm downfield from tetramethylsilane; "s" means singlet, "d" means doublet, "dd" means doublet of doublets, "ddd" means doublet of doublet of doublets, "t" means triplet, "m" means multiplet, and "br s" means broad singlet. For mass spectral data, the numerical value reported is the molecular weight of the parent molecular ion (M) formed by addition of $H^+$ (molecular weight of 1) to the molecule to give a M+1 peak observed by mass spectrometry using atmospheric pressure chemical ionization ($AP^+$).

Schemes 1 through 11 illustrate methods to prepare compounds of Formula 1 having a variety of substituents. Compounds of Formula 1 having substituents other than those particularly noted for Schemes 1 through 11 can be prepared by general methods known in the art of synthetic organic chemistry, including methods analogous to those described for Schemes 1 to 11.

Synthesis Example 1

Preparation of 3-fluoro-4-[fluoro-[4-(trifluoromethylsulfinyl)phenyl]methyl]-5-(triazol-2-yl)pyridine (compound 67)

Step A: Preparation of (3,5-difluoro-4-pyridyl)-[4-(trifluoromethylsulfanyl)phenyl]methanol To a stirred solution of 3,5-difluoro-pyridine (1.20 g, 10.4 mmol) in THF (20 mL) was added a freshly prepared lithium diisopropylamide solution (11.4 mmol in 10 mL of THF and n-Hexanes) slowly at −20° C. After stirring for 1 hr at −20 to −10° C., the reaction mixture was added a solution of 4-(trifluoromethylsulfanyl)benzaldehyde (2.15 g, 10.4 mmol) in THF (10 mL) at −20° C. After stirring for another 1 hr at −20 to −10° C., the reaction mixture was quenched by saturated $NH_4Cl$ aqueous solution, then diluted with water and extracted with ethyl acetate. The combined organic phases were washed with water and saturated aqueous NaCl solution, dried with anhydrous sodium sulfate and concentrated. The residue was purified by column chromatography on silica gel using hexanes/ethyl acetate as eluent to afford the title product as a pale white solid (1.36 g, 4.2 mmol).

$^1H$ NMR ($CDCl_3$) δ 8.34 (s, 2H), 7.66 (d, 2H), 7.48 (d, 2H), 6.29 (s, 1H).

Step B: Preparation of 3,5-difluoro-4-[fluoro-[4-(trifluoromethylsulfanyl)phenyl]methyl]pyridine To a stirred solution of (3,5-difluoro-4-pyridyl)-[4-(trifluoromethylsulfanyl)phenyl]methanol (i.e. the product of Step A) (650 mg, 2.02 mmol) in dichloromethane (25 mL) was added bis(2-methoxyethyl)aminosulfur trifluoride (0.55 mL, 2.96 mmol) at −78° C. After stirring for 2 hrs, the reaction mixture was diluted with saturated aqueous $NaHCO_3$ solution slowly and extracted with dichloromethane. The combined organic phases were washed with water and saturated aqueous NaCl solution, dried with anhydrous sodium sulfate and concentrated. The residue was purified by column chromatography on silica gel using hexanes/ethyl acetate (80:20 to 40:60) as eluent to afford the title compound, a compound of the present disclosure, as a pale-yellow oil (490 mg, 1.52 mmol).

$^1H$ NMR ($CDCl_3$) δ 8.41 (d, 2H), 7.70 (d, 2H), 7.49 (d, 2H), 6.88 (d, 1H).

Step C: Preparation of 3-fluoro-4-[fluoro-[4-(trifluoromethylsulfanyl)phenyl]methyl]-5-(triazol-2-yl)pyridine A mixture of 3,5-difluoro-4-[fluoro-[4-(trifluoromethylsulfanyl)phenyl]methyl]pyridine (i.e. the product of Step B) (300 mg, 0.93 mmol), 1,2,3-triazole (64 mg, 0.93 mmol) and $K_2CO_3$ (205 mg, 1.49 mmol) in DMF (4 mL) was stirred at 100° C. for 2 hrs. Then the reaction mixture was cooled to room temperature, partitioned between water and ethyl acetate. The organic phase was washed with water and saturated aqueous NaCl solution, dried with anhydrous sodium sulfate and concentrated. The residue was purified by column chromatography on silica gel using hexanes/ethyl acetate as eluent to afford the title product as a white solid (80 mg, 0.22 mmol).

$^1H$ NMR ($CDCl_3$) δ 8.96 (s, 1H), 8.57 (s, 1H), 7.96 (s, 2H), 7.68 (d, 2H), 7.60 (d, 2H), 7.24 (d, 1H).

Step D: Preparation of 3-fluoro-4-[fluoro-[4-(trifluoromethylsulfinyl)phenyl]methyl]-5-(triazol-2-yl)pyridine To a stirred solution of 3-fluoro-4-[fluoro-[4-(trifluoromethylsulfanyl)phenyl]methyl]-5-(triazol-2-yl)pyridine (i.e. the product of Step C) (100 mg, 0.27 mmol) in dichloromethane (3 mL) was added 3-chloroperoxybenzoic acid (91 mg, less than 77% purity) at 0° C. The reaction mixture was slowly warmed to room temperature and stirred for 3 hrs. Then the reaction mixture was quenched with aqueous solution of $NaHSO_3$ and partitioned between water and dichloromethane. The organic phase was washed with water and saturated aqueous NaCl solution, dried with anhydrous sodium sulfate and concentrated. The residue was purified by column chromatography on silica gel using hexanes/ethyl acetate as eluent to afford the title product as a colorless sticky oil (30 mg, 0.08 mmol).

$^1H$ NMR ($CDCl_3$) δ 9.00 (s, 1H), 8.59 (s, 1H), 7.98 (s, 2H), 7.83 (s, 4H), 7.30 (d, 1H).

Synthesis Example 2

Preparation of 3-[5-fluoro-4-[methoxy-[4-(trifluoromethylsulfanyl)phenyl]methyl]-3-pyridyl]-1,2,4-oxadiazole (compound 83)

Step A: Preparation of (3-bromo-5-fluoro-4-pyridyl)-[4-(trifluoromethylsulfanyl)phenyl]methanol To a stirred solution of 3-bromo-5-fluoro-pyridine (4.40 g, 25 mmol) in THE (20 mL) was added a freshly prepared lithium diisopropylamide solution (26 mmol in 20 mL of THE and n-Hexanes) slowly at −20° C. After stirring for 1 hr at −20 to −10° C., the reaction mixture was added a solution of 4-(trifluoromethylsulfanyl)benzaldehyde (4.85 g, 23.5 mmol) in THE (10 mL) at −20° C. After stirring for another 1 hr at −20 to −10° C., the reaction mixture was quenched with saturated $NH_4Cl$ aqueous solution, then diluted with water and extracted with ethyl acetate. The combined organic phases were washed with water and saturated aqueous NaCl solution, dried with anhydrous sodium sulfate and concentrated. The residue was purified by column chromatography on silica gel using hexanes/ethyl acetate as eluent to afford the title product as a pale-yellow oil (6.95 g, 18.2 mmol).

$^1H$ NMR ($CDCl_3$) δ 8.56 (s, 1H), 8.36 (s, 1H), 7.65 (d, 2H), 7.47 (d, 2H), 6.39 (d, 1H), 3.66 (d, 1H).

Step B: Preparation of 3-bromo-5-fluoro-4-[methoxy-[4-(trifluoromethylsulfanyl)phenyl]methyl]pyridine To a stirred solution of (3-bromo-5-fluoro-4-pyridyl)-[4-(trifluoromethylsulfanyl) phenyl]methanol (i.e. the product of Step A) (1.26 g, 3.30 mmol) in dry THE (10 mL) was added sodium hydride (165 mg, 4.12 mmol, 60% in mineral oil) at 0° C. The resulting mixture was stirred at room temperature for 1 hr and then treated with methyl iodide (0.24 mL, 3.96 mmol). After stirring at room temperature for another 1.5 hrs, the reaction mixture was treated with water and extracted with ethyl acetate/hexanes (1:1). The combined organic phases were washed with water and saturated aqueous sodium chloride solution, dried with anhydrous sodium sulfate and concentrated. The residue was purified by column chromatography on silica gel using hexanes/ethyl acetate (90:10 to 60:40) as eluent to afford the title compound as a pale-yellow oil (1.10 g, 2.80 mmol).

$^1H$ NMR ($CDCl_3$) δ 8.60 (s, 1H), 8.37 (s, 1H), 7.63 (d, 2H), 7.52 (d, 2H), 5.95 (s, 1H), 3.47 (s, 3H).

Step C: Preparation of 5-fluoro-4-[methoxy-[4-(trifluoromethylsulfanyl)phenyl]methyl]pyridine-3-carbonitrile A mixture of 3-bromo-5-fluoro-4-[methoxy[4-(trifluoromethylsulfanyl)phenyl]-methyl]pyridine (i.e. the product of Step B) (1.0 g, 2.52 mmol), $Zn(CN)_2$ (325 mg, 2.76 mmol), $Pd(PPh_3)_4$ (291 mg, 0.25 mmol) in N,N-dimethylforamide (5 mL) in a vial under nitrogen atmosphere was subjected for a reaction under microwave at 150° C. for 10 min. Then the reaction mixture was partitioned between water and ethyl acetate. The organic layer was washed with water and saturated aqueous sodium chloride solution, dried with anhydrous sodium sulfate and concentrated. The residue was purified by column chromatography on silica gel using hexanes/ethyl acetate (90:10 to 60:40) as eluent to afford the title compound as a yellow oil (0.80 g, 2.42 mmol).

$^1$H NMR ($CDCl_3$) δ 8.72 (s, 1H), 8.63 (s, 1H), 7.67 (d, 2H), 7.59 (d, 2H), 5.79 (s, 1H), 3.50 (s, 3H).

Step D: Preparation of 3-[5-fluoro-4-[methoxy-[4-(trifluoromethylsulfanyl)phenyl]methyl]-3-pyridyl]-1,2,4-oxadiazole A mixture of 5-fluoro-4-[methoxy-[4-(trifluoromethylsulfanyl)phenyl]methyl]pyridine-3-carbonitrile (i.e. the product of Step C) (0.27 g, 0.82 mmol), hydroxylamine (0.25 mL, 3.78 mmol, 50% in $H_2O$) in EtOH (5 ml) was stirred at room temperature for 48 hrs. The reaction mixture was then concentrated under reduced pressure. The residue was added trimethylorthoformate (0.5 mL) and one drop of concentrated hydrochloride acid. Then the mixture was stirred at 80° C. for 1 hr. The reaction mixture was cooled to room temperature, then partitioned between water and ethyl acetate. The organic layer was washed with water and saturated aqueous sodium chloride solution, dried with anhydrous sodium sulfate and concentrated. The residue was purified by column chromatography on silica gel using hexanes/ethyl acetate (90:10 to 60:40) as eluent to afford the title compound as a pale yellow oil (0.17 g, 0.46 mmol).

$^1$H NMR (CDCl3) δ 8.96 (s, 1H), 8.91 (s, 1H), 8.57 (s, 1H), 7.62 (d, 2H), 7.57 (d, 2H), 6.29 (s, 1H), 3.39 (s, 3H).

Synthesis Example 3

Preparation of 3-fluoro-4-[(R)-methoxy-[4-(trifluoromethoxy)phenyl]methyl]-5-(triazol-2 yl)pyridine (compound 125)

Step A: Preparation of (3,5-difluoro-4-pyridyl)-[4-(trifluoromethoxy)phenyl]methanol To a solution of compound 3,5-difluoro-pyridine (40 g, 0.347 mol, 1.0 eq.) in THE (400 ml) was added LDA 2 M in THE (191.3 mL, 0.381 mol, 1.1 eq.) slowly at −78° C. under $N_2$ atmosphere. Then the reaction mixture was stirred for 30 min then added compound 4-(trifluoromethoxy)benzaldehyde (72.4 g, 0.381 mol, 1.1 eq.) at −78° C. and stirred for 2h at −78° C. Reaction monitored by TLC, the reaction mixture was quenched with Sat. Aq $NH_4Cl$ extracted with EtOAc (3×500 ml) then dried over anhydrous $Na_2SO_4$ and concentrated under reduced pressure. Obtained crude was purified by column chromatography using 100-200 silica gel, eluted with 40% ethyl acetate/pet ether to afford the title product as an off white semi solid (70 g, 66% yield).

$^1$H NMR (d6-DMSO) δ 8.49 (s, 2H), 7.51 (d, 2H), 7.35 (d, 2H), 6.59 (d, 1H), 6.16 (d, 1H).

Step B: Preparation of (3,5-difluoro-4-pyridyl)-[4-(trifluoromethoxy)phenyl]methanone A solution of compound (3,5-difluoro-4-pyridyl)-[4-(trifluoromethoxy)phenyl]methanol (i.e. the product of Step A) (70.0 g, 0.229 mol, 1.0 eq) in dichloromethane (700 ml) was added activated $MnO_2$ (199 g, 2.29 mol, 10 eq.) at rt under $N_2$ atmosphere then stirred for 16 h. Reaction monitored by TLC the reaction mixture was filtered through the celite bed, and washed with dichloromethane (200 mL). The solvent was concentrated under reduced pressure to get crude solid. Obtained crude was purified by column chromatography using 100-200 silica gel, eluted with 30% ethyl acetate/pet ether to afford the title compound as an off white solid (65 g, 93% yield).

$^1$H NMR (d6-DMSO) δ 8.80 (s, 2H), 8.07 (d, 2H), 7.60 (d, 2H).

Step C: Preparation of [3-fluoro-5-(triazol-2-yl)-4-pyridyl]-[4-(trifluoromethoxy)phenyl]methanone To a solution of compound (3,5-difluoro-4-pyridyl)-[4-(trifluoromethoxy)phenyl]methanone (i.e. the product of Step B) (65 g, 0.214 mol, 1.0 eq) in DMF (650 ml) was added $K_2CO_3$ (29.6 g, 0.214 mol, 1.0 eq) and 1,2,3-triazole (14.8 g, 0.214 mol, 1.0 eq.) at rt under $N_2$ atmosphere. Then the reaction mixture was stirred for 48 h. Reaction monitored by TLC. The reaction mixture was poured into ice cold water (1000 ml) and extracted with EtOAc (3×300 ml). Then the organic layer was washed with brine (2×200 ml) & ice water (200 ml) then dried over anhydrous $Na_2SO_4$ and concentrated under reduced pressure. Obtained crude was purified by column chromatography using 100-200 silica gel, eluted to provide the title product as an off white solid (19 g, 25% yield).

$^1$H NMR (d6-DMSO) δ 9.29 (s, 1H), 8.91 (s, 1H), 8.11 (s, 2H), 8.00 (d, 2H), 7.51 (d, 2H).

Step D: Preparation of (R)-[3-fluoro-5-(triazol-2-yl)-4-pyridyl]-[4-(trifluoromethoxy)phenyl]methanol To a solution of (S)-(−)-a,a-diphenyl-2-pyrrolidinemethanol (2.73 g, 0.011 mol, 0.2 eq) in THE (190 ml) was added $B(OMe)_3$ (12.4 g, 0.012 mmol, 0.22 eq.) at rt then stirred for 1 h at rt under $N_2$ atmosphere. Then added borane dimethyl sulfide (6.16 g, 0.081 mol, 1.5 eq.) slowly at 0° C., meanwhile floating and exothermic was observed. Then added compound [3-fluoro-5-(triazol-2-yl)-4-pyridyl]-[4-(trifluoromethoxy)phenyl]methanone (i.e. the product of Step C) (19 g, 0.054 mol, 1.0 eq) (dissolved in THE 30 ml) at 0-5° C. then allowed to rt and stirred for 3 h. Reaction monitored by TLC. After completion of the reaction, it was cooled to 0° C. then reaction mixture was quenched with 2N HCl (80 ml) slowly drop wise meanwhile vigorous gas evolution and exothermic was observed, then extracted with ethyl acetate (3×200 ml), the organic layer was dried over anhydrous $Na_2SO_4$ and concentrated to get crude. Obtained crude was purified by column chromatography using 100-200 silica gel, eluted with 30% ethyl acetate/pet ether to provide the title product as colourless liquid (8.2 g, 43% yield). Chiral HPLC analysis with Chiralpak IF (4.6*250 mm) 5u column indicated the product had 95% ee as the R configuration. The R absolute configuration is assigned according to the literature, see: Moriyasu Masui & Takayuki Shioiri, *Synlett,* 1997, 273-274.

Step E: Preparation of 3-fluoro-4-[(R)-methoxy-[4-(trifluoromethoxv)phenyl]methyl]-5-(triazol-2-yl) pyridine To a solution of (R)-[3-fluoro-5-(triazol-2-yl)-4-pyridyl]-[4-(trifluoromethoxy)phenyl]methanol compound (8.2 g, 0.023 mol, 1.0 eq) in THE was added NaH (1.0 g, 0.046 mol, 2.0 eq) portion wise at 0° C. mean while floating was observed then stirred for 5 min at 0° C. then added MeI (4.93 g, 0.034 mol, 1.5 eq) at 0° C. Then stirred for 2 h at rt. Reaction monitored by TLC. The reaction mixture was poured into ice water (50 ml) and extracted with ethyl acetate (2×100 ml). Then the organic layer was dried over anhydrous $Na_2SO_4$ and concentrated under reduced pressure. Obtained crude solid was purified by column chromatography using 100-200 silica gel, eluted with 20% ethyl acetate/pet ether to get the title product as colourless liquid (6.0 g 70.5% yield). Chiral HPLC analysis indicated the product had 93% ee, $[\alpha]^{25}=-175.6°$ (MeOH, 0.4%).

$^1$H NMR (d6-DMSO) δ 8.81 (s, 1H), 8.78 (s, 1H), 8.32 (s, 2H), 7.51 (d, 2H), 7.37 (d, 2H), 5.66 (s, 1H), 3.21 (s, 3H).

By the procedures described herein together with methods known in the art, the following compounds of Tables 1 to 42N can be prepared. The following abbreviations are used in the Tables which follow: t means tertiary, s means secondary, n means normal, i means iso, c means cyclo, Me means methyl, Et means ethyl, Pr means propyl, i-Pr means isopropyl, Bu means butyl, Ph means phenyl, OMe means methoxy, OEt means ethoxy, SMe means methylthio, SEt means ethylthio, —CN means cyano, Ph means phenyl, Py means pyridinyl, —$NO_2$ means nitro, TMS means trimethylsilyl, S(O)Me means methylsulfinyl, and $S(O)_2Me$ means methylsulfonyl.

Fragments Q-1 through Q-19 shown below are referred to in Tables 1A to 981. The structures of fragments Q-1 through Q-19 are illustrated in Exhibit 3. The wavy line denotes the attachment point of the fragment to the remainder of the molecule.

Exhibit 3

Q-1

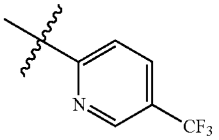

Q-2

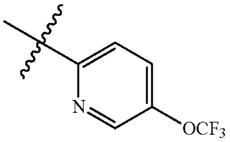

Q-3

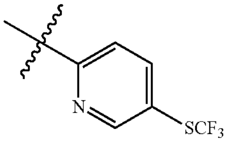

Q-4

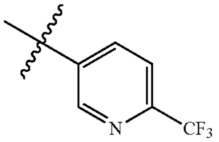

Q-5

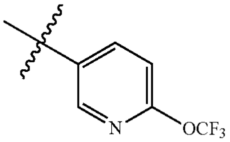

Q-6

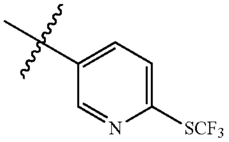

-continued

Q-7

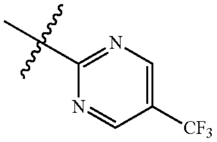

Q-8

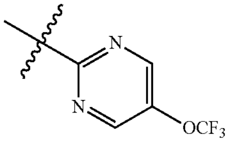

Q-10

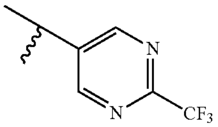

Q-11

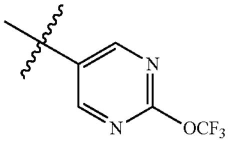

Q-9

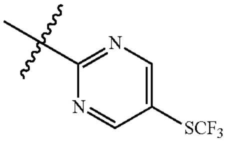

Q-10

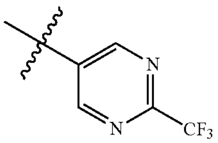

Q-11

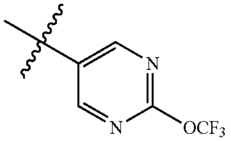

Q-12

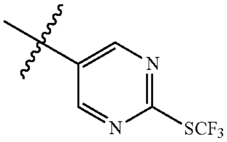

Q-13

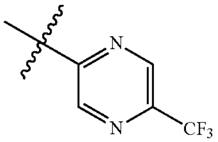

Q-14

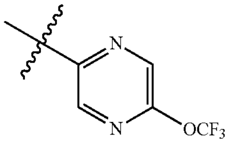

-continued

Q-15

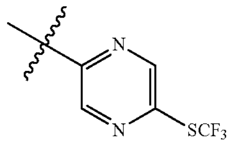

Q-16

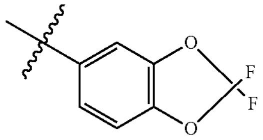

Q-17

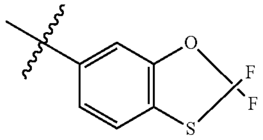

-continued

Q-18

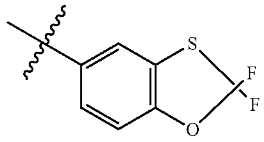

Q-19

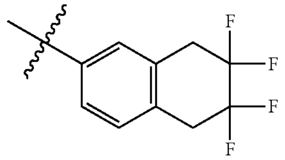

Tables 1A-42A pertain to the structure shown below.

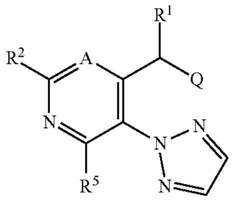

TABLE 1A $R^1$ is F, A is CH, $R^2$ is H and $R^5$ is H.

| Q | Q | Q |
|---|---|---|
| 4-chlorophenyl | 3-($CF_3$)phenyl | 3-Cl, 4-($CF_3$)phenyl |
| 4-bromophenyl | 3-($OCF_3$)phenyl | 3-Br, 4-($CF_3$)phenyl |
| 4-iodophenyl | 3-(s-Bu)phenyl | 3-Me, 4-($CF_3$)phenyl |
| 4-nitrophenyl | 3-(t-Bu)phenyl | 2,6-diF, 4-($CF_3$)phenyl |
| 4-cyanophenyl | 3-($CMe_2CH_2CH_3$)phenyl | 2,6-diCl, 4-($CF_3$)phenyl |
| 4-($CF_3$)phenyl | 3-(S-i-Pr)phenyl | 2-F, 4-($OCF_3$)phenyl |
| 4-($OCF_3$)phenyl | 3-($SCH_2CF_3$)phenyl | 2-Cl, 4-($OCF_3$)phenyl |
| 4-(s-Bu)phenyl | 3-($CF(CF_3)_2$)phenyl | 2-Me, 4-($OCF_3$)phenyl |
| 4-(t-Bu)phenyl | 2-F, 4-(t-Bu)phenyl | 3-F, 4-($OCF_3$)phenyl |
| 4-($CMe_2CH_2CH_3$)phenyl | 2-Cl, 4-(t-Bu)phenyl | 3-Cl, 4-($OCF_3$)phenyl |
| 4-(S-i-Pr)phenyl | 2-Me, 4-(t-Bu)phenyl | 3-Br, 4-($OCF_3$)phenyl |
| 4-($SCH_2CF_3$)phenyl | 3-F, 4-(t-Bu)phenyl | 3-Me, 4-($OCF_3$)phenyl |
| 4-($SCHF_2$)phenyl | 3-Cl, 4-(t-Bu)phenyl | 2,6-diF, 4-($OCF_3$)phenyl |
| 4-($S(O)CHF_2$)phenyl | 3-Br, 4-(t-Bu)phenyl | 2,6-diCl, 4-($OCF_3$)phenyl |
| 4-($SO_2CHF_2$)phenyl | 3-Me, 4-(t-Bu)phenyl | 2-F, 4-($CF_2CF_3$)phenyl |
| 4-($CF(CF_3)2$)phenyl | 2,6-diF, 4-(t-Bu)phenyl | 2-Cl, 4-($CF_2CF_3$)phenyl |
| 3-chlorophenyl | 2,6-diCl, 4-(t-Bu)phenyl | 2-Me, 4-($CF_2CF_3$)phenyl |
| 3-bromophenyl | 2-F, 4-($CF_3$)phenyl | 3-F, 4-($CF_2CF_3$)phenyl |
| 3-iodophenyl | 2-Cl, 4-($CF_3$)phenyl | 3-Cl, 4-($CF_2CF_3$)phenyl |
| 3-nitrophenyl | 2-Me, 4-($CF_3$)phenyl | 3-Br, 4-($CF_2CF_3$)phenyl |
| 3-cyanophenyl | 3-($SCF_3$)phenyl | 3-Me, 4-($CF_2CF_3$)phenyl |
| 4-($SCF_3$)phenyl | 3-($S(O)CF_3$)phenyl | Q-1 |
| 4-($S(O)CF_3$)phenyl | 3-($SO_2CF_3$)phenyl | Q-2 |
| 4-($SO_2CF_3$)phenyl | 3-($CF_2CF_3$)phenyl | Q-3 |
| 4-($CF_2CF_3$)phenyl | 3-($CF_2CF_2CF_3$)phenyl | Q-4 |
| 4-($CF_2CF_2CF_3$)phenyl | 3-($OCF_2CF_3$)phenyl | Q-5 |
| 4-($OCF_2CF_3$)phenyl | 2-F, 4-($OCF_2CF_3$)phenyl | Q-6 |
| 2-F, 4-($SCF_3$)phenyl | 2-Cl, 4-($OCF_2CF_3$)phenyl | Q-7 |
| 2-Cl, 4-($SCF_3$)phenyl | 2-Me, 4-($OCF_2CF_3$)phenyl | Q-8 |
| 2-Me, 4-($SCF_3$)phenyl | 3-F, 4-($OCF_2CF_3$)phenyl | Q-9 |
| 3-F, 4-($SCF_3$)phenyl | 3-Cl, 4-($OCF_2CF_3$)phenyl | Q-10 |
| 3-Cl, 4-($SCF_3$)phenyl | 3-Br, 4-($OCF_2CF_3$)phenyl | Q-11 |
| 3-Br, 4-($SCF_3$)phenyl | 3-Me, 4-($OCF_2CF_3$)phenyl | Q-12 |
| 3-Me, 4-($SCF_3$)phenyl | 2,6-diF, 4-($OCF_2CF_3$)phenyl | Q-13 |
| 2,6-diF, 4-($SCF_3$)phenyl | 2,6-diCl, 4-($OCF_2CF_3$)phenyl | Q-14 |
| 2,6-diCl, 4-($SCF_3$)phenyl | 3-F, 4-($CF_3$)phenyl | Q-15 |
| | | Q-16 |
| | | Q-17 |
| | | Q-18 |
| | | Q-19 |

The present disclosure also includes Tables 2A through 42A, each of which is constructed the same as Table 1A above except that the row heading in Table 1A (i.e. "A is CH, $R^4$ is H and $R^5$ is H.") below the Markush structure is replaced with the respective row heading shown below. For example, in Table 2A the row heading is "$R^1$ is F, A is CF, $R^4$ is H and $R^5$ is H, and Q is as defined in Table 1A above. Thus, the first entry in Table 2A specifically discloses 4-[(4-chlorophenyl)-fluoro-methyl]-3-fluoro-5-(triazol-2-yl) pyridine.

TABLE 1B

| Table | Table Headings |
|---|---|
| 2A | R1 is F, A is CF |
| 3A | R1 is F, A is CCl |
| 4A | R1 is F, A is CBr |
| 5A | R1 is F, A is CI |
| 6A | R1 is F, A is CMe |
| 7A | R1 is F, A is CEt |
| 8A | R1 is F, A is C-n-Pr |
| 9A | R1 is F, A is C-i-Pr |
| 10A | R1 is F, A is C-c-Pr |
| 11A | R1 is F, A is $CCF_3$ |
| 12A | R1 is F, A is COMe |
| 13A | R1 is F, A is C-OEt |
| 14A | R1 is F, A is N |
| 15A | R1 is OCH, A is CH |
| 16A | R1 is $OCH_3$, A is CF |
| 17A | R1 is OCH, A is CCl |
| 18A | R1 is OCH, A is CBr |
| 19A | R1 is OCH, A is CI |
| 20A | R1 is OCH, A is CMe |
| 21A | R1 is OCH, A is CEt |
| 22A | R1 is OCH, A is C-n-Pr |
| 23A | R1 is OCH, A is C-i-Pr |
| 24A | R1 is OCH, A is C-c-Pr |
| 25A | R1 is OCH, A is C-$CF_3$ |
| 26A | R1 is $OCH_3$, A is C-OMe |
| 27A | R1 is $OCH_3$, A is C-OEt |
| 28A | R1 is $OCH_3$, A is N |
| 29A | R1 is $SCH_3$, A is CH |
| 30A | R1 is $SCH_3$, A is CF |
| 31A | R1 is $SCH_3$, A is CCl |
| 32A | R1 is $SCH_3$, A is CBr |
| 33A | R1 is $SCH_3$, A is CI |
| 34A | R1 is $SCH_3$, A is CMe |
| 35A | R1 is $SCH_3$, A is CEt |
| 36A | R1 is $SCH_3$, A is C-n-Pr |
| 37A | R1 is $SCH_3$, A is C-i-Pr |
| 38A | R1 is $SCH_3$, A is C-c-Pr |
| 39A | R1 is $SCH_3$, A is C-$CF_3$ |
| 40A | R1 is $SCH_3$, A is C-OMe |
| 41A | R1 is $SCH_3$, A is C-OEt |
| 42A | R1 is $SCH_3$, A is N |

Table 1B is identical to Table 1A, except that the chemical structure in the Table 1B heading is replaced with the following structure:

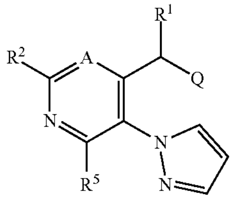

For example, the first compound in Table 1B is the structure shown immediately above wherein $R^1$ is F, A is CH, $R^2$ is H, $R^5$ is H, and Q is 4-chlorophenyl.

Tables 2B-42B

Tables 2B through 42B are constructed in a similar manner as Tables 2A through 42A.

Table 1C

Table 1C is identical to Table 1A, except that the chemical structure in the Table 1B heading is replaced with the following structure:

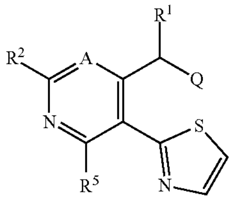

For example, the first compound in Table 1C is the structure shown immediately above wherein $R^1$ is F, A is CH, $R^2$ is H, $R^5$ is H, and Q is 4-chlorophenyl.

Tables 2C-42C

Tables 2C through 42C are constructed in a similar manner as Tables 2A through 42A.

Table 1D

Table 1D is identical to Table 1A, except that the chemical structure in the Table 1D heading is replaced with the following structure:

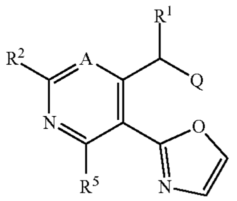

For example, the first compound in Table 1D is the structure shown immediately above wherein $R^1$ is F, A is CH, $R^2$ is H, $R^5$ is H, and Q is 4-chlorophenyl.

Tables 2D-42D

Tables 2D through 42D are constructed in a similar manner as Tables 2A through 42A.

Table 1E

Table 1E is identical to Table 1A, except that the chemical structure in the Table 1E heading is replaced with the following structure:

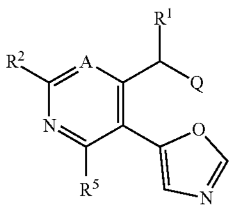

For example, the first compound in Table 1D is the structure shown immediately above wherein $R^1$ is F, A is CH, $R^2$ is H, $R^5$ is H, and Q is 4-chlorophenyl.

Tables 2E-42E

Tables 2E through 42E are constructed in a similar manner as Tables 2A through 42A.

Table 1F

Table 1F is identical to Table 1A, except that the chemical structure in the Table 1F heading is replaced with the following structure:

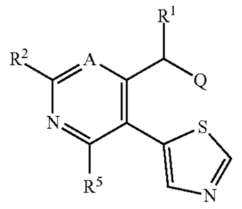

For example, the first compound in Table 1F is the structure shown immediately above wherein $R^1$ is F, A is CH, $R^2$ is H, $R^5$ is H, and Q is 4-chlorophenyl.

Tables 2F-42F

Tables 2F through 42F are constructed in a similar manner as Tables 2A through 42A.

Table 1G

Table 1G is identical to Table 1A, except that the chemical structure in the Table 1G heading is replaced with the following structure:

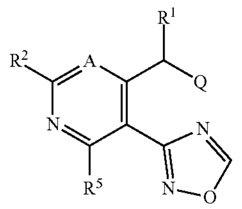

For example, the first compound in Table 1G is the structure shown immediately above wherein $R^1$ is F, A is CH, $R^2$ is H, $R^5$ is H, and Q is 4-chlorophenyl.

Tables 2G-42G

Tables 2G through 42G are constructed in a similar manner as Tables 2A through 42A.

Table 1H

Table 1H is identical to Table 1A, except that the chemical structure in the Table 1H heading is replaced with the following structure:

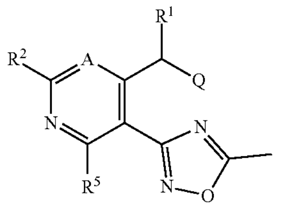

For example, the first compound in Table 1H is the structure shown immediately above wherein $R^1$ is F, A is CH, $R^2$ is H, $R^5$ is H, and Q is 4-chlorophenyl.

Tables 2H-42H

Tables 2H through 42H are constructed in a similar manner as Tables 2A through 42A.

Table 1I

Table 11 is identical to Table 1A, except that the chemical structure in the Table 1H heading is replaced with the following structure:

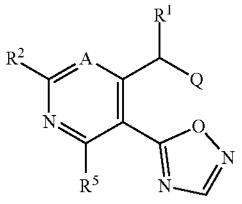

For example, the first compound in Table 11 is the structure shown immediately above wherein $R^1$ is F, A is CH, $R^2$ is H, $R^5$ is H, and Q is 4-chlorophenyl.

Tables 2I-42I

Tables 21 through 421 are constructed in a similar manner as Tables 2A through 42A.

Table 1J

Table 1J is identical to Table 1A, except that the chemical structure in the Table 1J heading is replaced with the following structure:

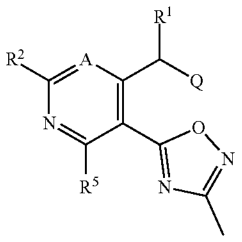

For example, the first compound in Table 1J is the structure shown immediately above wherein $R^1$ is F, A is CH, $R^2$ is H, $R^5$ is H, and Q is 4-chlorophenyl.

Tables 2J-42J

Tables 2J through 42J are constructed in a similar manner as Tables 2A through 42A.

Table 1K

Table 1K is identical to Table 1A, except that the chemical structure in the Table 1K heading is replaced with the following structure:

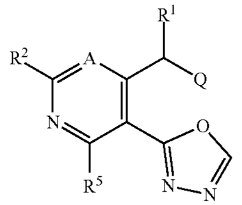

For example, the first compound in Table 1K is the structure shown immediately above wherein $R^1$ is F, A is CH, $R^2$ is H, $R^5$ is H, and Q is 4-chlorophenyl.

Tables 2K-42K

Tables 2K through 42K are constructed in a similar manner as Tables 2A through 42A.

Table 1L

Table 1L is identical to Table 1A, except that the chemical structure in the Table 1L heading is replaced with the following structure:

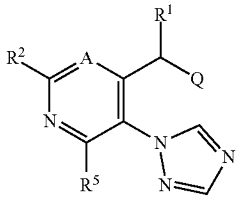

For example, the first compound in Table 1L is the structure shown immediately above wherein $R^1$ is F, A is CH, $R^2$ is H, $R^5$ is H, and Q is 4-chlorophenyl.

Tables 2L-42L

Tables 2L through 42L are constructed in a similar manner as Tables 2A through 42A.

Table 1M

Table 1M is identical to Table 1A, except that the chemical structure in the Table 1M heading is replaced with the following structure:

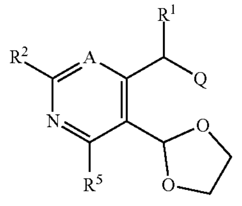

For example, the first compound in Table 1M is the structure shown immediately above wherein $R^1$ is F, A is CH, $R^2$ is H, $R^5$ is H, and Q is 4-chlorophenyl.

Tables 2M-42M

Tables 2M through 42M are constructed in a similar manner as Tables 2A through 42A.

Table 1N

Table 1N is identical to Table 1A, except that the chemical structure in the Table 1N heading is replaced with the following structure:

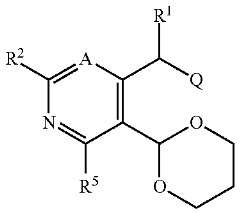

For example, the first compound in Table 1N is the structure shown immediately above wherein $R^1$ is F, A is CH, $R^2$ is H, $R^5$ is H, and Q is 4-chlorophenyl.

Tables 2N-42N

Tables 2N through 42N are constructed in a similar manner as Tables 2A through 42A.

A compound of this disclosure will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil in water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil in water emulsion, flowable concentrate and suspoemulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively, the entire formulation of active ingredient can be encapsulated (or"overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethylphosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters alkyl and aryl benzoates, γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, Solvents Guide, 2nd Ed., Interscience, New York, 1950.

The solid and liquid compositions of the present disclosure often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this disclosure may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 m can be wet milled using media mills to obtain particles with average diameters below 3 m. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 m range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology*, PJB Publications, Richmond, UK, 2000.

In the following Examples, all formulations are prepared in conventional ways. Compound numbers refer to compounds in Index Tables A-B. Without further elaboration, it is believed that one skilled in the art using the preceding description can utilize the present disclosure to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| compound 8 | 98.5% |
| silica aerogel | 0.5% |
| synthetic amorphous fine silica | 1.0% |

Example B

| Wettable Powder | |
|---|---|
| compound 14 | 65.0% |
| dodecylphenol polyethylene glycol ether | 2.0% |
| sodium ligninsulfonate | 4.0% |

-continued

| Wettable Powder | |
|---|---|
| sodium silicoaluminate | 6.0% |
| montmorillonite (calcined) | 23.0% |

Example C

| Granule | |
|---|---|
| compound 19 | 10.0% |
| attapulgite granules (low volatile matter, 0.71/0.30 mm; U.S.S. No. 25-50 sieves) | 90.0% |

Example D

| Extruded Pellet | |
|---|---|
| compound 78 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| compound 3 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| compound 86 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| compound 20 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Fertilizer Stick | |
|---|---|
| compound 32 | 2.5% |
| pyrrolidone-styrene copolymer | 4.8% |
| tristyrylphenyl 16-ethoxylate | 2.3% |
| talc | 0.8% |
| corn starch | 5.0% |
| slow-release fertilizer | 36.0% |
| kaolin | 38.0% |
| water | 10.6% |

Example I

| Suspension Concentrate | |
|---|---|
| compound 67 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
|---|---|
| compound 34 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| compound 39 | 25% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| compound 16 | 10.0% |
| imidacloprid | 5.0% |

-continued

| Suspoemulsion | |
|---|---|
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Compounds of this disclosure exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD©, KNOCKOUT®, STARLINK®, BOLLGARD®, NuCOTN® and NEWLEAF®, INVICTA RR2 PRO™, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may exhibit enhanced effects with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may exhibit enhanced effects with the phenotypic expression of proteins or other natural products toxic to invertebrate pests to provide greater-than-additive control of these pests.

Compositions of this disclosure can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present disclosure which further comprise at least one plant nutrient can be in the form of liquids or solids. Of note are solid formulations in the form of granules, small sticks or tablets. Solid formulations comprising a fertilizer composition can be prepared by mixing the compound or composition of the present disclosure with the fertilizer composition together with formulating ingredients and then preparing the formulation by methods such as granulation or extrusion. Alternatively solid formulations can be prepared by spraying a solution or suspension of a compound or composition of the present disclosure in a volatile solvent onto a previous prepared fertilizer composition in the form of dimensionally stable mixtures, e.g., granules, small sticks or tablets, and then evaporating the solvent.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

Nonagronomic uses of the present compounds and compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compounds and compositions of the present disclosure are suitable for systemic and/or non-systemic control of infestation or infection by parasites on animals. Compounds and compositions of the present disclosure are particularly suitable for combating external parasitic or disease transmitting pests. Compounds and compositions of the present disclosure are suitable for combating parasites that infest agricultural working animals, such as cattle, sheep, goats, horses, pigs, donkeys, camels, buffalos, rabbits, hens, turkeys, ducks, geese and bees; pet animals and domestic animals such as dogs, cats, pet birds and aquarium fish; as well as so-called experimental animals, such as hamsters, guinea pigs, rats and mice. By combating these parasites, fatalities and performance reduction (in terms of meat, milk, wool, skins, eggs, honey, etc.) are reduced, so that applying a composition comprising a compound of the present disclosure allows more economic and simple husbandry of animals.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera frugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocrocis medinalis* Guenée), grape leaffolder (*Desmia funeralis* Hübner), pickleworm (*Diaphania nitidalis* Stoll), cabbage center grub (*Hellula hydralis* Guenée), yellow stem borer (*Scirpophaga incertulas* Walker), white stem borer (*Scirpophaga innotata* Walker), top shoot borer (*Scirpophaga nivella* Fabricius), dark-headed rice borer (*Chilo polychrysus* Meyrick), striped riceborer (*Chilo suppressalis* Walker), cabbage cluster caterpillar (*Crocidolomia binotalis* Zeller)); leafrollers, budworms, seed worms, and fruit worms in the family Tortricidae (e.g., codling moth (*Cydia pomonella* Linnaeus), grape berry moth (*Paralobesia viteana* Clemens), oriental fruit moth (*Grapholita molesta* Busck), citrus false codling moth (*Cryptophlebia leucotreta* Meyrick), citrus borer (*Gymnandrosoma aurantianum* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree *tortrix* (*Pandemis cerasana* Hübner), apple brown *tortrix* (*Pandemis heparana* Denis & Schiffermuller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Phyllonorycter blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Serville), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus vestitus* Chittenden), Rocky Mountain billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera* LeConte)); chafers and other beetles from the family Scarabaeidae (e.g., Japanese beetle (*Popillia japonica* Newman), oriental beetle (*Anomala orientalis* Waterhouse, northern masked chafer (*Cyclocephala borealis* Arrow), southern masked chafer (*Cyclocephala immaculata* Olivier or *C. lurida* Bland), dung beetle and white grub (*Aphodius* spp.), black turfgrass *ataenius* (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae.

In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the order Hemiptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoridae and Delphacidae, treehoppers from the family Membracidae, psyllids from the families Liviidae, Psyllidae, and Triozidae, whiteflies from the family Aleyrodidae, aphids from the family Aphididae, *Phylloxera* from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae.

Agronomic and nonagronomic pests also include: eggs, larvae, nymphs and adults of the order Acari (mites) such as spider mites and red mites in the family Tetranychidae (e.g., European red mite (*Panonychus ulmi* Koch), twospotted spider mite (*Tetranychus urticae* Koch), McDaniel spider mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodecidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata* Duges), common fowl tick (*Argas radiatus* Raillet)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forsskil), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gasterophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion *thrips* (*Thrips tabaci* Lindeman), flower *thrips* (*Frankliniella* spp.), and other foliar feeding *thrips*; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* F. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Forster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the orders Mallophaga and Phthiraptera, and including the head louse (*Pediculus humanus* capitis De Geer), body louse (*Pediculus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Examples of invertebrate pests of stored grain include larger grain borer (Prostephanus *truncatus* Horn), lesser grain borer (*Rhyzopertha dominica* Fabricius), rice weevil (*Sitophilus oryzae* Linnaeus), maize weevil (*Sitophilus zeamais* Motschulsky), cowpea weevil (*Callosobruchus maculatus* Fabricius), red flour beetle (*Tribolium castaneum* Herbst), granary weevil (*Sitophilus granarius* Linnaeus), Indian meal moth (*Plodia interpunctella* Hübner), Mediterranean flour beetle (*Ephestia kuehniella* Zeller) and flat or rusty grain beetle (*Cryptolestes ferrugineus* Stephens).

Compounds of the present disclosure may have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the disclosure may have activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrocis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (Old World bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermuller (grape berry moth), *Pectinophora gossypiella* Saunders (pink bollworm), *Phyl-*

*locnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the disclosure have significant activity on members from the order Hemiptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Passerini (rosy apple aphid), *Eriosoma lanigerum* Hausmann (woolly apple aphid), *Hyalopterus pruni* Geoffroy (mealy plum aphid), *Lipaphis pseudobrassicae* Davis (turnip aphid), *Metopolophium dirrhodum* Walker (rose-grain aphid), *Macrosiphum euphorbiae* Thomas (potato aphid), *Myzus persicae* Sulzer (peach-potato aphid, green peach aphid), *Nasonovia ribisnigri* Mosley (lettuce aphid), Pemphigus spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricidus* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), Macrosteles *quadrilineatus* Forbes (aster leafhopper), *Nephotettix cincticeps* Uhler (green rice leafhopper), *Nephotettix nigropictus* Stil (rice leafhopper), *Nilaparvata lugens* Stil (brown planthopper), *Peregrinus maidis* Ashmead (corn planthopper), *Sogatella furcifera* Horváth (white-backed planthopper), *Tagosodes orizicolus* Muir (rice delphacid), *Typhlocyba pomaria* McAtee (white apple leafhopper), *Erythroneura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this disclosure also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythucha gossypii* Fabricius (cotton lace bug), *Cyrtopeltis modesta* Distant (tomato bug), *Dysdercus suturellus* Herrich-Schaffer (cotton stainer), *Euschistus servus* Say (brown stink bug), *Euschistus variolarius* Palisot de Beauvois (one-spotted stink bug), Graptostethus spp. (complex of seed bugs), *Halyomorpha halys* Stil (brown marmorated stink bug), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the disclosure include Thysanoptera (e.g., *Frankliniella occidentalis* Pergande (western flower *thrips*), *Scirtothrips citri* Moulton (citrus *thrips*), *Scirtothrips variabilis* Beach (soybean *thrips*), and *Thrips tabaci* Lindeman (onion *thrips*); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Of note is use of compounds of this disclosure for controlling western flower *thrips* (*Frankliniella occidentalis*). Of note is use of compounds of this disclosure for controlling potato leafhopper (*Empoasca fabae*). Of note is use of compounds of this disclosure for controlling cotton melon aphid (*Aphis gossypii*). Of note is use of compounds of this disclosure for controlling green peach aphid (*Myzus persicae*). Of note is use of compounds of this disclosure for controlling sweetpotato whitefly (*Bemisia tabaci*).

Compounds of the present disclosure may also be useful for increasing vigor of a crop plant. This method comprises contacting the crop plant (e.g., foliage, flowers, fruit or roots) or the seed from which the crop plant is grown with a compound of Formula 1 in amount sufficient to achieve the desired plant vigor effect (i.e. biologically effective amount). Typically the compound of Formula 1 is applied in a formulated composition. Although the compound of Formula 1 is often applied directly to the crop plant or its seed, it can also be applied to the locus of the crop plant, i.e. the environment of the crop plant, particularly the portion of the environment in close enough proximity to allow the compound of Formula 1 to migrate to the crop plant. The locus relevant to this method most commonly comprises the growth medium (i.e. medium providing nutrients to the plant), typically soil in which the plant is grown. Treatment of a crop plant to increase vigor of the crop plant thus comprises contacting the crop plant, the seed from which the crop plant is grown or the locus of the crop plant with a biologically effective amount of a compound of Formula 1.

Increased crop vigor can result in one or more of the following observed effects: (a) optimal crop establishment as demonstrated by excellent seed germination, crop emergence and crop stand; (b) enhanced crop growth as demonstrated by rapid and robust leaf growth (e.g., measured by leaf area index), plant height, number of tillers (e.g., for rice), root mass and overall dry weight of vegetative mass of the crop; (c) improved crop yields, as demonstrated by time to flowering, duration of flowering, number of flowers, total biomass accumulation (i.e. yield quantity) and/or fruit or grain grade marketability of produce (i.e. yield quality); (d) enhanced ability of the crop to withstand or prevent plant disease infections and arthropod, nematode or mollusk pest infestations; and (e) increased ability of the crop to withstand environmental stresses such as exposure to thermal extremes, suboptimal moisture or phytotoxic chemicals.

The compounds of the present disclosure may increase the vigor of treated plants compared to untreated plants by killing or otherwise preventing feeding of phytophagous invertebrate pests in the environment of the plants. In the absence of such control of phytophagous invertebrate pests, the pests reduce plant vigor by consuming plant tissues or sap, or transmiting plant pathogens such as viruses. Even in the absence of phytophagous invertebrate pests, the compounds of the disclosure may increase plant vigor by modifying metabolism of plants. Generally, the vigor of a crop plant will be most significantly increased by treating the plant with a compound of the disclosure if the plant is grown in a nonideal environment, i.e. an environment comprising one or more aspects adverse to the plant achieving the full genetic potential it would exhibit in an ideal environment.

Of note is a method for increasing vigor of a crop plant wherein the crop plant is grown in an environment comprising phytophagous invertebrate pests. Also of note is a method for increasing vigor of a crop plant wherein the crop plant is grown in an environment not comprising phytophagous invertebrate pests. Also of note is a method for increasing vigor of a crop plant wherein the crop plant is grown in an environment comprising an amount of moisture less than ideal for supporting growth of the crop plant. Of note is a method for increasing vigor of a crop plant wherein the crop is rice. Also of note is a method for increasing vigor of a crop plant wherein the crop is maize (corn). Also of note is a method for increasing vigor of a crop plant wherein the crop is soybean.

Compounds of this disclosure can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus, the present disclosure also pertains to a composition comprising a biologically effective amount of a compound of Formula 1, at least one additional component selected from the group consisting of surfactants, solid diluents and liquid diluents, and at least one additional biologically active compound or agent. For mixtures of the present disclosure, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this disclosure can be formulated are insecticides such as abamectin, acephate, acequinocyl, acetamiprid, acrinathrin, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H-naphtho[2,1-b]pyrano[3,4-e]pyran-4-yl]methyl cyclopropanecarboxylate), amidoflumet, amitraz, avermectin, azadirachtin, azinphos-methyl, benfuracarb, bensultap, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(1-cyclopropylethyl)amino]carbonyl]phenyl]-1-(3-chloro-2-pyridinyl)-1H-pyrazole-5-carboxamide), cycloprothrin, cycloxaprid ((5S,8R)-1-[(6-chloro-3-pyridinyl)methyl]-2,3,5,6,7,8-hexahydro-9-nitro-5,8-Epoxy-1H-imidazo[1,2-a]azepine) cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin (2-ethyl-3,7-dimethyl-6-[4-(trifluoromethoxy)phenoxy]-4-quinolinyl methyl carbonate), flonicamid, flubendiamide, flucythrinate, flufenerim, flufenoxuron, flufenoxystrobin (methyl (αE)-2-[[2-chloro-4-(trifluoromethyl)phenoxy]methyl]-α-(methoxymethylene)benzeneacetate), flufensulfone (5-chloro-2-[(3,4,4-trifluoro-3-buten-1-yl)sulfonyl]thiazole), fluhexafon, fluopyram, flupiprole (1-[2,6-dichloro-4-(trifluoromethyl)phenyl]-5-[(2-methyl-2-propen-1-yl)amino]-4-[(trifluoromethyl)sulfinyl]-1H-pyrazole-3-carbonitrile), flupyradifurone (4-[[(6-chloro-3-pyridinyl)methyl](2,2-difluoroethyl)amino]-2(5H)-furanone), fluvalinate, tau-fluvalinate, fonophos, formetanate, fosthiazate, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl]cyclopropanecarboxylate), hexaflumuron, hexythiazox, hydramethylnon, imidacloprid, indoxacarb, insecticidal soaps, isofenphos, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methiodicarb, methomyl, methoprene, methoxychlor, metofluthrin, methoxyfenozide, metofluthrin, monocrotophos, monofluorothrin ([2,3,5,6-tetrafluoro-4-(methoxymethyl)phenyl]methyl 3-(2-cyano-1-propen-1-yl)-2,2-dimethylcyclopropanecarboxylate), nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), pymetrozine, pyrafluprole, pyrethrin, pyridaben, pyridalyl, pyrifluquinazon, pyriminostrobin (methyl (αE)-2-[[[2-[(2,4-dichlorophenyl)amino]-6-(trifluoromethyl)-4-pyrimidinyl]oxy]methyl]-α-(methoxymethylene)benzeneacetate), pyriprole, pyriproxyfen, rotenone, ryanodine, silafluofen, spinetoram, spinosad, spirodiclofen, spiromesifen, spirotetramat, sulprofos, sulfoxaflor (N-[methyloxido[1-[6-(trifluoromethyl)-3-pyridinyl]ethyl]-$\lambda^4$-sulfanylidene]cyanamide), tebufenozide, tebufenpyrad, teflubenzuron, tefluthrin, terbufos, tetrachlorvinphos, tetramethrin, tetramethylfluthrin ([2,3,5,6-tetrafluoro-4-(methoxymethyl)phenyl]methyl 2,2,3,3-tetramethylcyclopropanecarboxylate), tetraniliprole, thiacloprid, thiamethoxam, thiodicarb, thiosultap-sodium, tioxazafen (3-phenyl-5-(2-thienyl)-1,2,4-oxadiazole), tolfenpyrad, tralomethrin, triazamate, trichlorfon, triflumezopyrim (2,4-dioxo-1-(5-pyrimidinylmethyl)-3-[3-(trifluoromethyl)phenyl]-2H-pyrido[1,2-a]pyrimidinium inner salt), triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, afidopyropen, amitraz, avermectin, azadirachtin, benfuracarb, bensultap, bifenthrin, buprofezin, cadusafos, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, flufensulfone, flupiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiodicarb, methomyl, methoprene, methoxyfenozide, metofluthrin, monofluorothrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumezopyrim, triflumuron, *Bacillus thuringiensis* delta-endotoxins, all strains of *Bacillus thuringiensis* and all strains of nucleo polyhedrosis viruses.

One embodiment of biological agents for mixing with compounds of this disclosure include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Indiana, USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

One embodiment of biological agents for mixing with compounds of this disclosure include one or a combination of (i) a bacterium of the genus *Actinomycetes, Agrobacterium, Arthrobacter, Alcaligenes, Aureobacterium, Azobacter, Bacillus, Beijerinckia, Bradyrhizobium, Brevibacillus, Burkholderia, Chromobacterium, Clostridium, Clavibacter, Comamonas, Corynebacterium, Curtobacterium, Enterobacter, Flavobacterium, Gluconobacter, Hydrogenophaga, Klebsiella, Methylobacterium, Paenibacillus, Pasteuria, Photorhabdus, Phyllobacterium, Pseudomonas, Rhizobium, Serratia, Sphingobacterium, Stenotrophomonas, Streptomyces, Variovorax*, or *Xenorhabdus*, for example a bacterium of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Bradyrhizobium japonicum, Chromobacterium subtsugae, Pasteuria nishizawae, Pasteuria penetrans, Pasteuria usage, Pseudomonas fluorescens*, and *Streptomyces lydicus*; (ii) a fungus such as green muscardine fungus; (iii) a virus including baculovirus, nucleopolyhedro virus such as *Helicoverpa zea* nucleopolyhedrovirus, *Anagrapha falcifera* nucleopolyhedrovirus; granulosis virus such as *Cydia pomonella* granulosis virus.

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present disclosure can further comprise a biologically effective amount of at least one additional invertebrate pest control active ingredient having a similar spectrum of control but belonging to a different chemical class or having a different site of action. These additional biologically active compounds or agents include, but are not limited to, acetylcholinesterase (AChE) inhibitors such as the carbamates methomyl, oxamyl, thiodicarb, triazamate, and the organophosphates chlorpyrifos; GABA-gated chloride channel antagonists such as the cyclodienes dieldrin and endosulfan, and the phenylpyrazoles ethiprole and fipronil; sodium channel modulators such as the pyrethroids bifenthrin, cyfluthrin, beta-cyfluthrin, cyhalothrin, lambda-cyhalothrin, cypermethrin, deltamethrin, dimefluthrin, esfenvalerate, metofluthrin and profluthrin; nicotinic acetylcholinereceptor (nAChR) agonists such as the neonicotinoids acetamiprid, clothianidin, dinotefuran, imidacloprid, nitenpyram, nithiazine, thiacloprid, and thiamethoxam, the sulfoximine sulfoxaflor, the butenolide flupyradifurone, and the mesoionic triflumezopyrim; nicotinic acetylcholine receptor (nAChR) allosteric activators such as the spinosyns spinetoram and spinosad; chloride channel activators such as the avermectins abamectin and emamectin; juvenile hormone mimics such as diofenolan, methoprene, fenoxycarb and pyriproxyfen; chordotonal organ modulators such as pymetrozine, pyrifluquinazon and flonicamid; mite growth inhibitors such as etoxazole; inhibitors of mitochondrial ATP synthase such as propargite; uncouplers of oxidative phosphorylation via disruption of the proton gradient such as chlorfenapyr; nicotinic acetylcholine receptor (nAChR) channel blockers such as the nereistoxin analogs cartap; inhibitors of chitin biosynthesis such as the benzoylureas flufenoxuron, hexaflumuron, lufenuron, novaluron, noviflumuron and triflumuron, and buprofezin; dipteran moulting disrupters such as cyromazine; ecdysone receptor agonists such as the diacylhydrazines methoxyfenozide and tebufenozide; octopamine receptor agonists such as amitraz; mitochondrial complex III electron transport inhibitors such as hydramethylnon and bifenazate; mitochondrial complex I electron transport inhibitors such as pyridaben; voltage-dependent sodium channel blockers such as indoxacarb; inhibitors of acetyl CoA carboxylase such as the tetronic and tetramic acids spirodiclofen, spiromesifen and spirotetramat; mitochondrial complex II electron transport inhibitors such as the ß-ketonitriles cyenopyrafen and cyflumetofen; ryanodine receptor modulators such as the anthranilic diamides chlorantraniliprole and cyantraniliprole, diamides such as flubendiamide, and ryanodine receptor ligands such as ryanodine; compounds wherein the target site responsible for biological activity is unknown or uncharacterized such as azadirachtinand pyridalyl; microbial disrupters of insect midgut membranes such as *Bacillus thuringiensis* and the delta-endotoxins they produce and *Bacillus sphaericus*; and biological agents including nuclear polyhedrosis (NPV) and other naturally occurring or genetically modified insecticidal viruses.

Further examples of biologically active compounds or agents with which compounds of this disclosure can be formulated are: fungicides such as acibenzolar-S-methyl, aldimorph, ametoctradin, aminopyrifen, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, copper hydroxide, copper oxychloride, copper sulfate, coumoxystrobin, cyazofamid, cyflufenamid, cymoxanil, cyproconazole, cyprodinil, dichlobentiazox, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dipymetitrone, dithianon, dithiolanes, dodemorph, dodine, econazole, etaconazole, edifenphos, enoxastrobin (also known as enestroburin), epoxiconazole, ethaboxam, ethirimol, etridiazole, famoxadone, fenamidone, fenaminstrobin, fenarimol, fenbuconazole, fenfuram, fenhexamide, fenoxanil, fenpiclonil, fenpicoxamid, fenpropidin, fenpropimorph, fenpyrazamine, fentin acetate, fentin hydroxide, ferbam, ferimzone, flometoquin, florylpicoxamid, fluopimomide, fluazinam, fludioxonil, flufenoxystrobin, fluindapyr, flumorph, fluopicolide, fluopyram, fluoxapiprolin, fluoxastrobin, fluquinconazole, flusilazole, flusulfamide, flutianil, flutolanil, flutriafol, fluxapyroxad, folpet, fthalide (also known as phthalide), fuberidazole, furalaxyl, furametpyr, hexaconazole, hymexazole, guazatine, imazalil, imibenconazole, iminoctadine albesilate, iminoctadine triacetate, inpyrfluxam, iodicarb, ipconazole, ipfentrifluconazole, ipflufenoquin, isofetamid, iprobenfos, iprodione, iprovalicarb, isoflucypram, isoprothiolane, isopyrazam, isotianil, kasugamycin, kresoxim-methyl, lancotrione, mancozeb, mandipropamid, mandestrobin, maneb, mapanipyrin, mefentrifluconazole, mepronil, meptyldinocap, metalaxyl (including metalaxyl-M/mefenoxam), metconazole, methasulfocarb, metiram, metominostrobin, metyltetraprole, metrafenone, myclobutanil, naftitine, neo-asozin (ferric methanearsonate), nuarimol, octhilinone, ofurace, orysastrobin, oxadixyl, oxathiapiprolin, oxolinic acid, oxpoconazole, oxycarboxin, oxytetracycline, penconazole, pencycuron, penflufen, penthiopyrad, perfurazoate, phosphorous acid (including salts thereof, e.g., fosetyl-aluminm), picoxystrobin, piperalin, polyoxin, probenazole, prochloraz, procymidone, propamocarb, propiconazole, propineb, proquinazid, prothiocarb, prothioconazole, pydiflumetofen (Adepidyn®), pyraclostrobin, pyrametostrobin, pyrapropoyne, pyraoxystrobin, pyraziflumid, pyrazophos, pyribencarb, pyributacarb, pyridachlometyl, pyrifenox, pyriofenone, perisoxazole, pyrimethanil, pyrifenox, pyrrolnitrin, pyroquilon, quinconazole, quinmethionate, quinofumelin, quinoxyfen, quintozene, silthiofam, sedaxane, simeconazole, spiroxamine, streptomycin, sulfur, tebuconazole, tebufloquin, teclofthalam, tecloftalam, tecnazene, terbinafine, tetraconazole, thiabendazole, thifluzamide, thiophanate, thiophanate-methyl, thiram, tiadinil, tolclofos-methyl, tolprocarb, tolyfluanid, triadimefon, triadimenol, triarimol, triazoxide, tribasic copper sulfate, triclopyricarb, tridemorph, trifloxystrobin, triflumizole, trimoprhamide tricyclazole, trifloxystrobin, triforine, triticonazole, uniconazole, validamycin, valifenalate (also known as valifenal), vinclozolin, zineb, ziram, zoxamide and 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone; nematocides such as fluopyram, spirotetramat, thiodicarb, fosthiazate, abamectin, iprodione, fluensulfone, dimethyl disulfide, tioxazafen, 1,3-dichloropropene (1,3-D), metam (sodium and potassium), dazomet, chloropicrin, fenamiphos, ethoprophos, cadusaphos, terbufos, imicyafos, oxamyl, carbofuran, tioxazafen, *Bacillus firmus* and *Pasteuria nishizawae*; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this disclosure with In certain instances, combinations of a compound of this disclosure with other biologically active (particularly invertebrate pest control) compounds or agents (i.e. active ingredients) can result in an enhanced effect. Reducing the quantity of active ingredients released in the environment while ensuring effective pest control is always desirable. When enhanced invertebrate pest control occurs at application rates giving agronomically satisfactory levels of invertebrate pest control, such combinations can be advantageous for reducing crop production cost and decreasing environmental load.

Compounds of this disclosure and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The exogenously applied invertebrate pest control compounds of this disclosure in combination with the expressed toxin proteins may provide an enhanced effect.

General references for these agricultural protectants (i.e. insecticides, fungicides, nematocides, acaricides, herbicides and biological agents) include *The Pesticide Manual,* 13th Edition, C. D. S. Tomlin, Ed., British Crop Protection Council, Farnham, Surrey, U.K., 2003 and *The BioPesticide Manual,* $2^{nd}$ Edition, L. G. Copping, Ed., British Crop Protection Council, Farnham, Surrey, U.K., 2001.

Compounds of this disclosure can be combined or formulated with polynucleotides including, but not limited to, DNA, RNA, and/or chemically modified nucleotides influencing the amount of a particular target through down regulation, interference, suppression or silencing of the genetically derived transcript that render an insecticidal effect.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula 1 alone.

Table A lists specific combinations of a compound of Formula 1 with other invertebrate pest control agents illustrative of the mixtures, compositions and methods of the present disclosure. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a compound of Formula 1 (e.g., "50:1 to 1:50" of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present disclosure and includes additional embodiments of weight ratio ranges for application rates.

TABLE A

| Invertebrate Pest Control Agent | Mode of Action or Chemical Class | Typical Weight Ratio |
|---|---|---|
| Abamectin | chloride channel activator | 50:1 to 1:50 |
| Acetamiprid | nicotinic acetylcholinereceptor (nAChR) agonist | 150:1 to 1:200 |
| Amitraz | octopamine receptor agonists | 200:1 to 1:100 |
| Avermectin | macrocyclic lactones | 50:1 to 1:50 |
| Azadirachtin | unknown site of action | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin biosynthesis inhibitors | 500:1 to 1:50 |
| Cartap | nicotinic acetylcholine receptor (nAChR) channel blocker | 100:1 to 1:200 |
| Chlorantraniliprole | ryanodine receptor modulator | 100:1 to 1:120 |
| Chlorfenapyr | uncouplers of oxidative phosphorylation | 300:1 to 1:200 |
| Chlorpyrifos | acetylcholinesterase inhibitor | 500:1 to 1:200 |
| Clothianidin | nicotinic acetylcholine receptor (nAChR) agonist | 100:1 to 1:400 |
| Cyantraniliprole | Ryanodine receptor modulator | 100:1 to 1:120 |
| Cyfluthrin | sodium channel modulator | 150:1 to 1:200 |
| Cyhalothrin | sodium channel modulator | 150:1 to 1:200 |
| Cypermethrin | sodium channel modulator | 150:1 to 1:200 |
| Cyromazine | dipteran moulting disrupter | 400:1 to 1:50 |
| Deltamethrin | sodium channel modulators | 50:1 to 1:400 |
| Dieldrin | GABA-gated chloride channel antagonist | 200:1 to 1:100 |
| Dinotefuran | nicotinic acetylcholine receptor (nAChR) agonist | 150:1 to 1:200 |
| Diofenolan | juvenile hormone mimic | 150:1 to 1:200 |
| Emamectin | chloride channel activator | 50:1 to 1:10 |
| Endosulfan | GABA-gated chloride channel antagonist | 200:1 to 1:100 |
| Esfenvalerate | sodium channel modulator | 100:1 to 1:400 |
| Ethiprole | GABA-regulated chloride channel antagonist | 200:1 to 1:100 |
| Fenothiocarb | | 150:1 to 1:200 |
| Fenoxycarb | juvenile hormone mimic | 500:1 to 1:100 |
| Fenvalerate | sodium channel modulator | 150:1 to 1:200 |
| Fipronil | GABA-regulated chloride channel antagonist | 150:1 to 1:100 |
| Flonicamid | selective hemipteran feeding blocker | 200:1 to 1:100 |
| Flubendiamide | ryanodine receptor modulator | 100:1 to 1:120 |
| Flufenoxuron | chitin biosynthesis inhibitor | 200:1 to 1:100 |
| Hexaflumuron | chitin biosynthesis inhibitor | 300:1 to 1:50 |
| Hydramethylnon | mitochondrial Complex III electron transport inhibitors | 150:1 to 1:250 |
| Imidacloprid | nicotinic acetylcholine receptor (nAChR) agonist | 1000:1 to 1:1000 |
| Indoxacarb | voltage-dependent sodium channel blocker | 200:1 to 1:50 |
| Lambda-cyhalothrin | sodium channel modulator | 50:1 to 1:250 |
| Lufenuron | chitin biosynthesis inhibitor | 500:1 to 1:250 |
| Metaflumizone | voltage-dependent sodium channel blocker | 200:1 to 1:200 |
| Methomyl | acetylcholinesterase inhibitor | 500:1 to 1:100 |
| Methoprene | juvenile hormone mimic | 500:1 to 1:100 |
| Methoxyfenozide | ecdysone receptor agonist | 50:1 to 1:50 |
| Nitenpyram | nicotinic acetylcholine receptor (nAChR) agonist | 150:1 to 1:200 |
| Nithiazine | nicotinic acetylcholine receptor (nAChR) agonist | 150:1 to 1:200 |
| Novaluron | chitin biosynthesis inhibitor | 500:1 to 1:150 |
| Oxamyl | acetylcholinesterase inhibitors | 200:1 to 1:200 |
| Pymetrozine | selective hemipteran feeding blocker | 200:1 to 1:100 |
| Pyrethrin | sodium channel modulator | 100:1 to 1:10 |
| Pyridaben | mitochondrial Complex 1 electron transport inhibitor | 200:1 to 1:100 |
| Pyridalyl | unknown site of action | 200:1 to 1:100 |
| Pyriproxyfen | juvenile hormone mimic | 500:1 to 1:100 |
| Ryanodine | ryanodine receptor ligand | 100:1 to 1:120 |
| Spinetoram | nicotinic acetylcholine receptor (nAChR) allosteric activator | 150:1 to 1:100 |
| Spinosad | nicotinic acetylcholine receptor (nAChR) allosteric activators | 500:1 to 1:10 |
| Spirodiclofen | acetyl CoA carboxylase inhibitor | 200:1 to 1:200 |
| Spiromesifen | acetyl CoA carboxylase inhibitor | 200:1 to 1:200 |
| Tebufenozide | ecdysone receptor agonist | 500:1 to 1:250 |

TABLE A-continued

| Invertebrate Pest Control Agent | Mode of Action or Chemical Class | Typical Weight Ratio |
|---|---|---|
| Thiacloprid | nicotinic acetylcholine receptor (nAChR) agonist | 100:1 to 1:200 |
| Thiamethoxam | nicotinic acetylcholine receptor (nAChR) agonist | 1250:1 to 1:1000 |
| Thiodi carb | acetylcholinesterase inhibitors | 500:1 to 1:400 |
| Thiosultap-sodium | Nicotinic acetylcholine receptor (nAChR) channel blocker | 150:1 to 1:100 |
| Tralomethrin | sodium channel modulator | 150:1 to 1:200 |
| Triazamate | acetyl cholinesterase inhibitors | 250:1 to 1:100 |
| Triflumezopyrim | | |
| Triflumuron | chitin synthesis inhibitor | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present disclosure wherein the at least one additional biologically active compound or agent is selected from the Invertebrate Pest Control Agents listed in Table A above.

The weight ratios of a compound, including a compound of Formula 1, an N-oxide or a salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Tables B1 to B6 are embodiments of specific compositions comprising a compound of Formula 1 (compound numbers (Cmpd. No.) refer to compounds in Index Table A) and an additional invertebrate pest control agent.

TABLE B1

| Mixture No. | Cmpd. No. | and | Invertebrate Pest Control Agent |
|---|---|---|---|
| B1-1 | 8 | and | Abamectin |
| B1-2 | 8 | and | Acetamiprid |
| B1-3 | 8 | and | Amitraz |
| B1-4 | 8 | and | Avermectin |
| B1-5 | 8 | and | Azadirachtin |
| B1-6 | 8 | and | Bensultap |
| B1-7 | 8 | and | Beta-cyfluthrin |
| B1-8 | 8 | and | Bifenthrin |
| B1-9 | 8 | and | Buprofezin |
| B1-10 | 8 | and | Cartap |
| B1-11 | 8 | and | Chlorantraniliprole |
| B1-12 | 8 | and | Chlorfenapyr |
| B1-13 | 8 | and | Chlorpyrifos |
| B1-14 | 8 | and | Clothianidin |
| B1-15 | 8 | and | Cyantraniliprole |
| B1-16 | 8 | and | Cyfluthrin |
| B1-17 | 8 | and | Cyhalothrin |
| B1-18 | 8 | and | Cypermethrin |
| B1-19 | 8 | and | Cyromazine |
| B1-20 | 8 | and | Deltamethrin |
| B1-21 | 8 | and | Dieldrin |
| B1-22 | 8 | and | Dinotefuran |
| B1-23 | 8 | and | Diofenolan |
| B1-24 | 8 | and | Emamectin |
| B1-25 | 8 | and | Endosulfan |
| B1-26 | 8 | and | Esfenvalerate |
| B1-27 | 8 | and | Ethiprole |
| B1-28 | 8 | and | Fenothiocarb |
| B1-29 | 8 | and | Fenoxycarb |
| B1-30 | 8 | and | Fenvalerate |
| B1-31 | 8 | and | Fipronil |
| B1-32 | 8 | and | Flonicamid |

TABLE B1-continued

| Mixture No. | Cmpd. No. | and | Invertebrate Pest Control Agent |
|---|---|---|---|
| B1-33 | 8 | and | Flubendiamide |
| B1-34 | 8 | and | Flufenoxuron |
| B1-35 | 8 | and | Hexaflumuron |
| B1-36 | 8 | and | Hydramethylnon |
| B1-37 | 8 | and | Imidacloprid |
| B1-38 | 8 | and | Indoxacarb |
| B1-39 | 8 | and | Lambda-cyhalothrin |
| B1-40 | 8 | and | Lufenuron |
| B1-41 | 8 | and | Metaflumizone |
| B1-42 | 8 | and | Methomyl |
| B1-43 | 8 | and | Methoprene |
| B1-44 | 8 | and | Methoxyfenozide |
| B1-45 | 8 | and | Nitenpyram |
| B1-46 | 8 | and | Nithiazine |
| B1-47 | 8 | and | Novaluron |
| B1-48 | 8 | and | Oxamyl |
| B1-49 | 8 | and | Phosmet |
| B1-50 | 8 | and | Pymetrozine |
| B1-51 | 8 | and | Pyrethrin |
| B1-52 | 8 | and | Pyridaben |
| B1-53 | 8 | and | Pyridalyl |
| B1-54 | 8 | and | Pyriproxyfen |
| B1-55 | 8 | and | Ryanodine |
| B1-56 | 8 | and | Spinetoram |
| B1-57 | 8 | and | Spinosad |
| B1-58 | 8 | and | Spirodiclofen |
| B1-59 | 8 | and | Spiromesifen |
| B1-60 | 8 | and | Spirotetramat |
| B1-61 | 8 | and | Sulfoxaflor |
| B1-62 | 8 | and | Tebufenozide |
| B1-63 | 8 | and | Tefluthrin |
| B1-64 | 8 | and | Thiacloprid |
| B1-65 | 8 | and | Thiamethoxam |
| B1-66 | 8 | and | Thiodicarb |
| B1-67 | 8 | and | Thiosultap-sodium |
| B1-68 | 8 | and | Tolfenpyrad |
| B1-69 | 8 | and | Tralomethrin |
| B1-70 | 8 | and | Triazamate |
| B1-71 | 8 | and | Triflumezopyrim |
| B1-72 | 8 | and | Triflumuron |
| B1-73 | 8 | and | *Bacillus thuringiensis* |
| B1-74 | 8 | and | *Bacillus thuringiensis* delta-endotoxin |
| B1-75 | 8 | and | NPV (e.g., Gemstar) |

Table B2

Table B2 is identical to Table B1, except that each reference to compound 8 in the column headed "Cmpd. No." is replaced by a reference to compound 14. For example, the first mixture in Table B2 is designated B2-1 and is a mixture of compound 14 and the additional invertebrate pest control agent abamectin.

Table B3

Table B3 is identical to Table B1, except that each reference to compound 8 in the column headed "Cmpd. No." is replaced by a reference to compound 19. For example, the first mixture in Table B3 is designated B3-1 and is a mixture of compound 19 and the additional invertebrate pest control agent abamectin.

Table B4

Table B4 is identical to Table B1, except that each reference to compound 8 in the column headed "Cmpd. No." is replaced by a reference to compound 78. For example, the first mixture in Table B4 is designated B4-1 and is a mixture of compound 78 and the additional invertebrate pest control agent abamectin.

Table B5

Table B5 is identical to Table B1, except that each reference to compound 8 in the column headed "Cmpd. No." is replaced by a reference to compound 3. For example, the first mixture in Table B5 is designated B5-1 and is a mixture of compound 3 and the additional invertebrate pest control agent abamectin.

Table B6

Table B6 is identical to Table B1, except that each reference to compound 8 in the column headed "Cmpd. No." is replaced by a reference to compound 86. For example, the first mixture in Table B6 is designated B6-1 and is a mixture of compound 86 and the additional invertebrate pest control agent abamectin.

The specific mixtures listed in Tables B1 to B6 typically combine a compound of Formula 1 with the other invertebrate pest agent in the ratios specified in Table A.

Listed below in Tables C1 to C6 are specific mixtures comprising a compound of Formula 1 (compound numbers (Cmpd. No.) refer to compounds in Index Table A) and an additional invertebrate pest control agent. Tables C1 to C19 further list specific weight ratios typical of the mixtures of Tables C1 to C19. For example, the first weight ratio entry of the first line of Table C1 specifically discloses the mixture of Compound 1 of Index Table A with abamectin applied in a weight ratio of 100 parts Compound 1 to 1 part abamectin.

TABLE C1

| Mixture No. | Cmpd. No. | and | Invertebrate Pest Control Agent | Typical Mixture Ratios (by weight) | | | | | | | | |
|---|---|---|---|---|---|---|---|---|---|---|---|---|
| C1-1 | 8 | and | Abamectin | 100:1 | 10:1 | 5:1 | 2:1 | 1:1 | 1:2 | 1:5 | 1:10 | 1:100 |
| C1-2 | 8 | and | Acetamiprid | 100:1 | 10:1 | 5:1 | 2:1 | 1:1 | 1:2 | 1:5 | 1:10 | 1:100 |
| C1-3 | 8 | and | Amitraz | 100:1 | 10:1 | 5:1 | 2:1 | 1:1 | 1:2 | 1:5 | 1:10 | 1:100 |
| C1-4 | 8 | and | Avermectin | 100:1 | 10:1 | 5:1 | 2:1 | 1:1 | 1:2 | 1:5 | 1:10 | 1:100 |
| C1-5 | 8 | and | Azadirachtin | 100:1 | 10:1 | 5:1 | 2:1 | 1:1 | 1:2 | 1:5 | 1:10 | 1:100 |
| C1-6 | 8 | and | Bensultap | 100:1 | 10:1 | 5:1 | 2:1 | 1:1 | 1:2 | 1:5 | 1:10 | 1:100 |
| C1-7 | 8 | and | Beta-cyfluthrin | 100:1 | 10:1 | 5:1 | 2:1 | 1:1 | 1:2 | 1:5 | 1:10 | 1:100 |
| C1-8 | 8 | and | Bifenthrin | 100:1 | 10:1 | 5:1 | 2:1 | 1:1 | 1:2 | 1:5 | 1:10 | 1:100 |
| C1-9 | 8 | and | Buprofezin | 100:1 | 10:1 | 5:1 | 2:1 | 1:1 | 1:2 | 1:5 | 1:10 | 1:100 |
| C1-10 | 8 | and | Cartap | 100:1 | 10:1 | 5:1 | 2:1 | 1:1 | 1:2 | 1:5 | 1:10 | 1:100 |
| C1-11 | 8 | and | Chlorantraniliprole | 100:1 | 10:1 | 5:1 | 2:1 | 1:1 | 1:2 | 1:5 | 1:10 | 1:100 |
| C1-12 | 8 | and | Chlorfenapyr | 100:1 | 10:1 | 5:1 | 2:1 | 1:1 | 1:2 | 1:5 | 1:10 | 1:100 |
| C1-13 | 8 | and | Chlorpyrifos | 100:1 | 10:1 | 5:1 | 2:1 | 1:1 | 1:2 | 1:5 | 1:10 | 1:100 |
| C1-14 | 8 | and | Clothianidin | 100:1 | 10:1 | 5:1 | 2:1 | 1:1 | 1:2 | 1:5 | 1:10 | 1:100 |

TABLE C1-continued

| Mixture No. | Cmpd. No. | and | Invertebrate Pest Control Agent | Typical Mixture Ratios (by weight) | | | | | | | | |
|---|---|---|---|---|---|---|---|---|---|---|---|---|
| C1-15 | 8 | and | Cyantraniliprole | 100:1 | 10:1 | 5:1 | 2:1 | 1:1 | 1:2 | 1:5 | 1:10 | 1:100 |
| C1-16 | 8 | and | Cyfluthrin | 100:1 | 10:1 | 5:1 | 2:1 | 1:1 | 1:2 | 1:5 | 1:10 | 1:100 |
| C1-17 | 8 | and | Cyhalothrin | 100:1 | 10:1 | 5:1 | 2:1 | 1:1 | 1:2 | 1:5 | 1:10 | 1:100 |
| C1-18 | 8 | and | Cypermethrin | 100:1 | 10:1 | 5:1 | 2:1 | 1:1 | 1:2 | 1:5 | 1:10 | 1:100 |
| C1-19 | 8 | and | Cyromazine | 100:1 | 10:1 | 5:1 | 2:1 | 1:1 | 1:2 | 1:5 | 1:10 | 1:100 |
| C1-20 | 8 | and | Deltamethrin | 100:1 | 10:1 | 5:1 | 2:1 | 1:1 | 1:2 | 1:5 | 1:10 | 1:100 |
| C1-21 | 8 | and | Dieldrin | 100:1 | 10:1 | 5:1 | 2:1 | 1:1 | 1:2 | 1:5 | 1:10 | 1:100 |
| C1-22 | 8 | and | Dinotefuran | 100:1 | 10:1 | 5:1 | 2:1 | 1:1 | 1:2 | 1:5 | 1:10 | 1:100 |
| C1-23 | 8 | and | Diofenolan | 100:1 | 10:1 | 5:1 | 2:1 | 1:1 | 1:2 | 1:5 | 1:10 | 1:100 |
| C1-24 | 8 | and | Emamectin | 100:1 | 10:1 | 5:1 | 2:1 | 1:1 | 1:2 | 1:5 | 1:10 | 1:100 |
| C1-25 | 8 | and | Endosulfan | 100:1 | 10:1 | 5:1 | 2:1 | 1:1 | 1:2 | 1:5 | 1:10 | 1:100 |
| C1-26 | 8 | and | Esfenvalerate | 100:1 | 10:1 | 5:1 | 2:1 | 1:1 | 1:2 | 1:5 | 1:10 | 1:100 |
| C1-27 | 8 | and | Ethiprole | 100:1 | 10:1 | 5:1 | 2:1 | 1:1 | 1:2 | 1:5 | 1:10 | 1:100 |
| C1-28 | 8 | and | Fenothiocarb | 100:1 | 10:1 | 5:1 | 2:1 | 1:1 | 1:2 | 1:5 | 1:10 | 1:100 |
| C1-29 | 8 | and | Fenoxycarb | 100:1 | 10:1 | 5:1 | 2:1 | 1:1 | 1:2 | 1:5 | 1:10 | 1:100 |
| C1-30 | 8 | and | Fenvalerate | 100:1 | 10:1 | 5:1 | 2:1 | 1:1 | 1:2 | 1:5 | 1:10 | 1:100 |
| C1-31 | 8 | and | Fipronil | 100:1 | 10:1 | 5:1 | 2:1 | 1:1 | 1:2 | 1:5 | 1:10 | 1:100 |
| C1-32 | 8 | and | Flonicamid | 100:1 | 10:1 | 5:1 | 2:1 | 1:1 | 1:2 | 1:5 | 1:10 | 1:100 |
| C1-33 | 8 | and | Flubendiamide | 100:1 | 10:1 | 5:1 | 2:1 | 1:1 | 1:2 | 1:5 | 1:10 | 1:100 |
| C1-34 | 8 | and | Flufenoxuron | 100:1 | 10:1 | 5:1 | 2:1 | 1:1 | 1:2 | 1:5 | 1:10 | 1:100 |
| C1-35 | 8 | and | Hexaflumuron | 100:1 | 10:1 | 5:1 | 2:1 | 1:1 | 1:2 | 1:5 | 1:10 | 1:100 |
| C1-36 | 8 | and | Hydramethylnon | 100:1 | 10:1 | 5:1 | 2:1 | 1:1 | 1:2 | 1:5 | 1:10 | 1:100 |
| C1-37 | 8 | and | Imidacloprid | 100:1 | 10:1 | 5:1 | 2:1 | 1:1 | 1:2 | 1:5 | 1:10 | 1:100 |
| C1-38 | 8 | and | Indoxacarb | 100:1 | 10:1 | 5:1 | 2:1 | 1:1 | 1:2 | 1:5 | 1:10 | 1:100 |
| C1-39 | 8 | and | Lambda-cyhalothrin | 100:1 | 10:1 | 5:1 | 2:1 | 1:1 | 1:2 | 1:5 | 1:10 | 1:100 |
| C1-40 | 8 | and | Lufenuron | 100:1 | 10:1 | 5:1 | 2:1 | 1:1 | 1:2 | 1:5 | 1:10 | 1:100 |
| C1-41 | 8 | and | Metaflumizone | 100:1 | 10:1 | 5:1 | 2:1 | 1:1 | 1:2 | 1:5 | 1:10 | 1:100 |
| C1-42 | 8 | and | Methomyl | 100:1 | 10:1 | 5:1 | 2:1 | 1:1 | 1:2 | 1:5 | 1:10 | 1:100 |
| C1-43 | 8 | and | Methoprene | 100:1 | 10:1 | 5:1 | 2:1 | 1:1 | 1:2 | 1:5 | 1:10 | 1:100 |
| C1-44 | 8 | and | Methoxyfenozide | 100:1 | 10:1 | 5:1 | 2:1 | 1:1 | 1:2 | 1:5 | 1:10 | 1:100 |
| C1-45 | 8 | and | Nitenpyram | 100:1 | 10:1 | 5:1 | 2:1 | 1:1 | 1:2 | 1:5 | 1:10 | 1:100 |
| C1-46 | 8 | and | Nithiazine | 100:1 | 10:1 | 5:1 | 2:1 | 1:1 | 1:2 | 1:5 | 1:10 | 1:100 |
| C1-47 | 8 | and | Novaluron | 100:1 | 10:1 | 5:1 | 2:1 | 1:1 | 1:2 | 1:5 | 1:10 | 1:100 |
| C1-48 | 8 | and | Oxamyl | 100:1 | 10:1 | 5:1 | 2:1 | 1:1 | 1:2 | 1:5 | 1:10 | 1:100 |
| C1-49 | 8 | and | Phosmet | 100:1 | 10:1 | 5:1 | 2:1 | 1:1 | 1:2 | 1:5 | 1:10 | 1:100 |
| C1-50 | 8 | and | Pymetrozine | 100:1 | 10:1 | 5:1 | 2:1 | 1:1 | 1:2 | 1:5 | 1:10 | 1:100 |
| C1-51 | 8 | and | Pyrethrin | 100:1 | 10:1 | 5:1 | 2:1 | 1:1 | 1:2 | 1:5 | 1:10 | 1:100 |
| C1-52 | 8 | and | Pyridaben | 100:1 | 10:1 | 5:1 | 2:1 | 1:1 | 1:2 | 1:5 | 1:10 | 1:100 |
| C1-53 | 8 | and | Pyridalyl | 100:1 | 10:1 | 5:1 | 2:1 | 1:1 | 1:2 | 1:5 | 1:10 | 1:100 |
| C1-54 | 8 | and | Pyriproxyfen | 100:1 | 10:1 | 5:1 | 2:1 | 1:1 | 1:2 | 1:5 | 1:10 | 1:100 |
| C1-55 | 8 | and | Ryanodine | 100:1 | 10:1 | 5:1 | 2:1 | 1:1 | 1:2 | 1:5 | 1:10 | 1:100 |
| C1-56 | 8 | and | Spinetoram | 100:1 | 10:1 | 5:1 | 2:1 | 1:1 | 1:2 | 1:5 | 1:10 | 1:100 |
| C1-57 | 8 | and | Spinosad | 100:1 | 10:1 | 5:1 | 2:1 | 1:1 | 1:2 | 1:5 | 1:10 | 1:100 |
| C1-58 | 8 | and | Spirodiclofen | 100:1 | 10:1 | 5:1 | 2:1 | 1:1 | 1:2 | 1:5 | 1:10 | 1:100 |
| C1-59 | 8 | and | Spiromesifen | 100:1 | 10:1 | 5:1 | 2:1 | 1:1 | 1:2 | 1:5 | 1:10 | 1:100 |
| C1-60 | 8 | and | Spirotetramat | 100:1 | 10:1 | 5:1 | 2:1 | 1:1 | 1:2 | 1:5 | 1:10 | 1:100 |
| C1-61 | 8 | and | Sulfoxaflor | 100:1 | 10:1 | 5:1 | 2:1 | 1:1 | 1:2 | 1:5 | 1:10 | 1:100 |
| C1-62 | 8 | and | Tebufenozide | 100:1 | 10:1 | 5:1 | 2:1 | 1:1 | 1:2 | 1:5 | 1:10 | 1:100 |
| C1-63 | 8 | and | Tefluthrin | 100:1 | 10:1 | 5:1 | 2:1 | 1:1 | 1:2 | 1:5 | 1:10 | 1:100 |
| C1-64 | 8 | and | Thiacloprid | 100:1 | 10:1 | 5:1 | 2:1 | 1:1 | 1:2 | 1:5 | 1:10 | 1:100 |
| C1-65 | 8 | and | Thiamethoxam | 100:1 | 10:1 | 5:1 | 2:1 | 1:1 | 1:2 | 1:5 | 1:10 | 1:100 |
| C1-66 | 8 | and | Thiodicarb | 100:1 | 10:1 | 5:1 | 2:1 | 1:1 | 1:2 | 1:5 | 1:10 | 1:100 |
| C1-67 | 8 | and | Thiosultap-sodium | 100:1 | 10:1 | 5:1 | 2:1 | 1:1 | 1:2 | 1:5 | 1:10 | 1:100 |
| C1-68 | 8 | and | Tolfenpyrad | 100:1 | 10:1 | 5:1 | 2:1 | 1:1 | 1:2 | 1:5 | 1:10 | 1:100 |
| C1-69 | 8 | and | Tralomethrin | 100:1 | 10:1 | 5:1 | 2:1 | 1:1 | 1:2 | 1:5 | 1:10 | 1:100 |
| C1-70 | 8 | and | Triazamate | 100:1 | 10:1 | 5:1 | 2:1 | 1:1 | 1:2 | 1:5 | 1:10 | 1:100 |
| C1-71 | 8 | and | Triflumezopyrim | 100:1 | 10:1 | 5:1 | 2:1 | 1:1 | 1:2 | 1:5 | 1:10 | 1:100 |
| C1-72 | 8 | and | Triflumuron | 100:1 | 10:1 | 5:1 | 2:1 | 1:1 | 1:2 | 1:5 | 1:10 | 1:100 |
| C1-73 | 8 | and | *Bacillus thuringiensis* | 100:1 | 10:1 | 5:1 | 2:1 | 1:1 | 1:2 | 1:5 | 1:10 | 1:100 |
| C1-74 | 8 | and | *Bacillus thuringiensis* delta-endotoxin | 100:1 | 10:1 | 5:1 | 2:1 | 1:1 | 1:2 | 1:5 | 1:10 | 1:100 |
| C1-75 | 8 | and | NPV (e.g., Gemstar) | 100:1 | 10:1 | 5:1 | 2:1 | 1:1 | 1:2 | 1:5 | 1:10 | 1:100 |

Table C2

Table C2 is identical to Table C1, except that each reference to compound 8 in the column headed "Cmpd. No." is replaced by a reference to compound 14. For example, the first weight ratio entry of the first line of Table C2 specifically discloses the mixture of Compound 14 with abamectin applied in a weight ratio of 100 parts Compound 1 to 1 part abamectin.

Table C3

Table C3 is identical to Table C1, except that each reference to compound 8 in the column headed "Cmpd. No." is replaced by a reference to compound 19. For example, the first weight ratio entry of the first line of Table C3 specifically discloses the mixture of Compound 19 with abamectin applied in a weight ratio of 100 parts Compound 1 to 1 part abamectin.

Table C4

Table C4 is identical to Table C1, except that each reference to compound 8 in the column headed "Cmpd. No." is replaced by a reference to compound 78. For example, the first weight ratio entry of the first line of Table C4 specifically discloses the mixture of Compound 78 with abamectin applied in a weight ratio of 100 parts Compound 1 to 1 part abamectin.

Table C5

Table C5 is identical to Table C1, except that each reference to compound 8 in the column headed "Cmpd. No." is replaced by a reference to compound 3. For example, the first weight ratio entry of the first line of Table C5 specifically discloses the mixture of Compound 3 with abamectin applied in a weight ratio of 100 parts Compound 1 to 1 part abamectin.

Table C6

Table C6 is identical to Table C1, except that each reference to compound 8 in the column headed "Cmpd. No." is replaced by a reference to compound 86. For example, the first weight ratio entry of the first line of Table C6 specifically discloses the mixture of Compound 86 with abamectin applied in a weight ratio of 100 parts Compound 1 to 1 part abamectin.

Listed below in Tables D1 to D6 are embodiments of specific compositions comprising a compound of Formula 1 (compound numbers (Cmpd. No.) refer to compounds in Index Table A) and an additional fungicide.

TABLE D1

| Mixture No. | Cmpd. No. | and | Fungicide |
|---|---|---|---|
| D1-1 | 8 | and | Probenazole |
| D1-2 | 8 | and | Tiadinil |
| D1-3 | 8 | and | Isotianil |
| D1-4 | 8 | and | Pyroquilon |
| D1-5 | 8 | and | Metominostrobin |
| D1-6 | 8 | and | Flutolanil |
| D1-7 | 8 | and | Validamycin |
| D1-8 | 8 | and | Furametpyr |
| D1-9 | 8 | and | Pencycuron |
| D1-10 | 8 | and | Simeconazole |

TABLE D1-continued

| Mixture No. | Cmpd. No. | and | Fungicide |
|---|---|---|---|
| D1-11 | 8 | and | Orysastrobin |
| D1-12 | 8 | and | Trifloxystrobin |
| D1-13 | 8 | and | Isoprothiolane |
| D1-14 | 8 | and | Azoxy strobin |
| D1-15 | 8 | and | Tricyclazole |
| D1-16 | 8 | and | Hexaconazole |
| D1-17 | 8 | and | Difenoconazole |
| D1-18 | 8 | and | Cyproconazole |
| D1-19 | 8 | and | Propiconazole |
| D1-20 | 8 | and | Fenoxanil |
| D1-21 | 8 | and | Ferimzone |
| D1-22 | 8 | and | Fthalide |
| D1-23 | 8 | and | Kasugamycin |
| D1-24 | 8 | and | Picoxy strobin |
| D1-25 | 8 | and | Penthiopyrad |
| D1-26 | 8 | and | Famoxadone |
| D1-27 | 8 | and | Cymoxanil |
| D1-28 | 8 | and | Proquinazid |
| D1-29 | 8 | and | Flusilazole |
| D1-30 | 8 | and | Mancozeb |
| D1-31 | 8 | and | Copper hydroxide |
| D1-32 | 8 | and | oxathiapiprolin |

Table D2

Table D2 is identical to Table D1, except that each reference to compound 8 in the column headed "Cmpd. No." is replaced by a reference to compound 14. For example, the first mixture in Table D2 is designated D2-1 and is a mixture of compound 14 and the additional fungicide probenazole.

Table D3

Table D3 is identical to Table D1, except that each reference to compound 8 in the column headed "Cmpd. No." is replaced by a reference to compound 19. For example, the first mixture in Table D3 is designated D3-1 and is a mixture of compound 19 and the additional fungicide probenazole.

Table D4

Table D4 is identical to Table D1, except that each reference to compound 8 in the column headed "Cmpd. No." is replaced by a reference to compound 78. For example, the first mixture in Table D4 is designated D4-1 and is a mixture of compound 78 and the additional fungicide probenazole.

Table D5

Table D5 is identical to Table D1, except that each reference to compound 8 in the column headed "Cmpd. No." is replaced by a reference to compound 3. For example, the first mixture in Table D5 is designated D5-1 and is a mixture of compound 3 and the additional fungicide probenazole.

Table D6

Table D6 is identical to Table D1, except that each reference to compound 8 in the column headed "Cmpd. No." is replaced by a reference to compound 86. For example, the first mixture in Table D6 is designated D6-1 and is a mixture of compound 86 and the additional fungicide probenazole.

Invertebrate pests are controlled in agronomic and nonagronomic applications by applying one or more compounds of this disclosure, typically in the form of a composition, in a biologically effective amount, to the environment of the pests, including the agronomic and/or nonagronomic locus of infestation, to the area to be protected, or directly on the pests to be controlled.

Thus the present disclosure comprises a method for controlling an invertebrate pest in agronomic and/or nonagronomic applications, comprising contacting the invertebrate pest or its environment with a biologically effective amount of one or more of the compounds of the disclosure, or with a composition comprising at least one such compound or a composition comprising at least one such compound and a biologically effective amount of at least one additional biologically active compound or agent. Examples of suitable compositions comprising a compound of the disclosure and a biologically effective amount of at least one additional biologically active compound or agent include granular compositions wherein the additional active compound is present on the same granule as the compound of the disclosure or on granules separate from those of the compound of the disclosure.

To achieve contact with a compound or composition of the disclosure to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the disclosure can be applied to the plant foliage or the soil. Compounds of this disclosure can also be effectively delivered through plant uptake by contacting the plant with a composition comprising a compound of this disclosure applied as a soil drench of a liquid formulation, a granular formulation to the soil, a nursery box treatment or a dip of transplants. Of note is a composition of the present disclosure in the form of a soil drench liquid formulation. Also of note is a method for controlling an invertebrate pest comprising contacting the invertebrate pest or its environment with a biologically effective amount of a compound of the present disclosure or with a composition comprising a biologically effective amount of a compound of the present disclosure. Of further note is this method wherein the environment is soil and the composition is applied to the soil as a soil drench formulation. Of further note is that compounds of this disclosure are also effective by localized application to the locus of infestation. Other methods of contact include application of a compound or a composition of the disclosure by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the disclosure. The compounds of this disclosure can also be impregnated into materials for fabricating invertebrate control devices (e.g., insect netting).

Compounds of the disclosure are useful in treating all plants, plant parts and seeds. Plant and seed varieties and cultivars can be obtained by conventional propagation and breeding methods or by genetic engineering methods. Genetically modified plants or seeds (transgenic plants or seeds) are those in which a heterologous gene (transgene) has been stably integrated into the plant's or seed's genome. A transgene that is defined by its particular location in the plant genome is called a transformation or transgenic event.

Genetically modified plant and seed cultivars which can be treated according to the disclosure include those that are resistant against one or more biotic stresses (pests such as nematodes, insects, mites, fungi, etc.) or abiotic stresses (drought, cold temperature, soil salinity, etc.), or that contain other desirable characteristics. Plants and seeds can be genetically modified to exhibit traits of, for example, herbicide tolerance, insect-resistance, modified oil profiles or drought tolerance. Useful genetically modified plants and seeds containing single gene transformation events or combinations of transformation events are listed in Table Z. Additional information for the genetic modifications listed in Table Z can be obtained from the following databases:

http://www2.oecd.org/biotech/byidentifier.aspx
http://www.aphis.usda.go
http://gmoinfo.jrc.ec.europa.eu The following abbreviations are used in Table Z which follows: tol. is tolerance, res. is resistance, SU is sulfonylurea, ALS is acetolactate synthase, HPPD is 4-Hydroxyphenylpyruvate Dioxygenase, NA is Not Available.

TABLE Z

| Crop | Event Name | Event Code | Trait(s) | Gene(s) |
|---|---|---|---|---|
| Alfalfa | J101 | MON-00101-8 | Glyphosate tol. | cp4 epsps (aroA:CP4) |
| Alfalfa | J163 | MON-ØØ163-7 | Glyphosate tol. | cp4 epsps (aroA:CP4) |
| Canola* | 23-18-17 (Event 18) | CGN-89465-2 | High lauric acid oil | te |
| Canola* | 23-198 (Event 23) | CGN-89465-2 | High lauric acid oil | te |
| Canola* | 61061 | DP-Ø61Ø61-7 | Glyphosate tol. | gat4621 |
| Canola* | 73496 | DP-Ø73496-4 | Glyphosate tol. | gat4621 |
| Canola* | GT200 (RT200) | MON-89249-2 | Glyphosate tol. | cp4 epsps (aroA:CP4); goxv247 |
| Canola* | GT73 (RT73) | MON-ØØØ73-7 | Glyphosate tol. | cp4 epsps (aroA:CP4); goxv247 |
| Canola* | HCN10 (Topas 19/2) | NA | Glufosinate tol. | bar |
| Canola* | HCN28 (T45) | ACS-BNØØ8-2 | Glufosinate tol. | pat (syn) |
| Canola* | HCN92 (Topas 19/2) | ACS-BNØØ7-1 | Glufosinate tol. | bar |
| Canola* | MON88302 | MON-883Ø2-9 | Glyphosate tol. | cp4 epsps (aroA:CP4) |
| Canola* | MPS961 | NA | Phytate breakdown | phyA |
| Canola* | MPS962 | NA | Phytate breakdown | phyA |
| Canola* | MPS963 | NA | Phytate breakdown | phyA |
| Canola* | MPS964 | NA | Phytate breakdown | phyA |
| Canola* | MPS965 | NA | Phytate breakdown | phyA |
| Canola* | MS1 (B91-4) | ACS-BNØØ4-7 | Glufosinate tol. | bar |
| Canola* | MS8 | ACS-BNØØ5-8 | Glufosinate tol. | bar |

TABLE Z-continued

| Crop | Event Name | Event Code | Trait(s) | Gene(s) |
|---|---|---|---|---|
| Canola* | OXY-235 | ACS-BNØ11-5 | Oxynil tol. | bxn |
| Canola* | PHY14 | NA | Glufosinate tol. | bar |
| Canola* | PHY23 | NA | Glufosinate tol. | bar |
| Canola* | PHY35 | NA | Glufosinate tol. | bar |
| Canola* | PHY36 | NA | Glufosinate tol. | bar |
| Canola* | RF1 (B93-101) | ACS-BNØØ1-4 | Glufosinate tol. | bar |
| Canola* | RF2 (B94-2) | ACS-BNØØ2-5 | Glufosinate tol. | bar |
| Canola* | RF3 | ACS-BNØØ3-6 | Glufosinate tol. | bar |
| Bean | EMBRAPA 5.1 | EMB-PV051-1 | Disease res. | acl (sense and antisense) |
| Brinjal (Eggplant) | EE-1 | | Insect res. | cry1Ac |
| Carnation | 11 (7442) | FLO-07442-4 | SU tol..; modified flower color | surB; dfr; hfl (f3'5'h) |
| Carnation | 11363 (1363A) | FLO-11363-1 | SU tol.; modified flower color | surB; dfr; bp40 (f3'5'h) |
| Carnation | 1226A (11226) | FLO-11226-8 | SU tol.; modified flower color | surB; dfr; bp40 (f3'5'h) |
| Carnation | 123.2.2 (40619) | FLO-4Ø619-7 | SU tol.; modified flower color | surB; dfr; hfl (f3'5'h) |
| Carnation | 123.2.38 (40644) | FLO-4Ø644-4 | SU tol.; modified flower color | surB; dfr; hfl (f3'5'h) |
| Carnation | 123.8.12 | FLO-4Ø689-6 | SU tol.; modified flower color | surB; dfr; bp40 (f3'5'h) |
| Carnation | 123.8.8 (40685) | FLO-4Ø685-1 | SU tol.; modified flower color | surB; dfr; bp40 (f3'5'h) |
| Carnation | 1351A (11351) | FLO-11351-7 | SU tol.; modified flower color | surB; dfr; bp40 (f3'5'h) |
| Carnation | 1400A (11400) | FLO-114ØØ-2 | SU tol.; modified flower color | surB; dfr; bp40 (f3'5'h) |
| Carnation | 15 | FLO-ØØØ15-2 | SU tol.; modified flower color | surB; dfr; hfl (f3'5'h) |
| Carnation | 16 | FLO-ØØØ16-3 | SU tol.; modified flower color | surB; dfr; hfl (f3'5'h) |
| Carnation | 4 | FLO-ØØØØ4-9 | SU tol.; modified flower color | surB; dfr; hfl (f3'5'h) |
| Carnation | 66 | FLO-ØØØ66-8 | SU tol.; delayed senescence | surB; acc |
| Carnation | 959A (11959) | FLO-11959-3 | SU tol.; modified flower color | surB; dfr; bp40 (f3'5'h) |
| Carnation | 988A (11988) | FLO-11988-7 | SU tol.; modified flower color | surB; dfr; bp40 (f3'5'h) |
| Carnation | 26407 | IFD-26497-2 | SU tol.; modified flower color | surB; dfr; bp40 (f3'5'h) |
| Carnation | 25958 | IFD-25958-3 | SU tol.; modified flower color | surB; dfr; bp40 (f3'5'h) |
| Chicory | RM3-3 | NA | Glufosinate tol. | bar |
| Chicory | RM3-4 | NA | Glufosinate tol. | bar |
| Chicory | RM3-6 | NA | Glufosinate tol. | bar |
| Cotton | 19-51a | DD-Ø1951A-7 | ALS herbicide tol. | S4-HrA |
| Cotton | 281-24-236 | DAS-24236-5 | Glufosinate tol.; insect res. | pat (syn); cry1F |
| Cotton | 3006-210-23 | DAS-21Ø23-5 | Glufosinate tol.; insect res. | pat (syn); cry1Ac |
| Cotton | 31707 | NA | Oxynil tol.; insect res. | bxn; cry1Ac |
| Cotton | 31803 | NA | Oxynil tol.; insect res. | bxn; cry1Ac |
| Cotton | 31807 | NA | Oxynil tol.; insect res. | bxn; cry1Ac |
| Cotton | 31808 | NA | Oxynil tol.; insect res. | bxn; cry1Ac |
| Cotton | 42317 | NA | Oxynil tol.; insect res. | bxn; cry1Ac |
| Cotton | BNLA-601 | NA | Insect res. | cry1Ac |
| Cotton | BXN10211 | BXN10211-9 | Oxynil tol. | bxn; cry1Ac |
| Cotton | BXN10215 | BXN10215-4 | Oxynil tol. | bxn; cry1Ac |
| Cotton | BXN10222 | BXN10222-2 | Oxynil tol. | bxn; cry1Ac |
| Cotton | BXN10224 | BXN10224-4 | Oxynil tol. | bxn; cry1Ac |
| Cotton | COT102 | SYN-IR102-7 | Insect res. | vip3A(a) |
| Cotton | COT67B | SYN-IR67B-1 | Insect res. | cry1Ab |
| Cotton | COT202 | | Insect res. | vip3A |
| Cotton | Event 1 | NA | Insect res. | cry1Ac |
| Cotton | GMF Cry1A | GTL-GMF311-7 | Insect res. | cry1Ab-Ac |
| Cotton | GHB119 | BCS-GH005-S | Insect res. | cry2Ae |
| Cotton | GHB614 | BCS-GH002-5 | Glyphosate tol. | 2mepsps |
| Cotton | GK12 | NA | Insect res. | cry1Ab-Ac |
| Cotton | LLCotton25 | ACS-GH001-3 | Glufosinate tol. | bar |
| Cotton | MLS 9124 | NA | Insect res. | cry1C |
| Cotton | MON1076 | MON-89924-2 | Insect res. | cry1Ac |
| Cotton | MON1445 | MON-01445-2 | Glyphosate tol. | cp4 epsps (aroA:CP4) |
| Cotton | MON15985 | MON-15985-7 | Insect res. | cry1Ac; cry2Ab2 |
| Cotton | MON1698 | MON-89383-1 | Glyphosate tol. | cp4 epsps (aroA:CP4) |
| Cotton | MON531 | MON-00531-6 | Insect res. | cry1Ac |
| Cotton | MON757 | MON-00757-7 | Insect res. | cry1Ac |

TABLE Z-continued

| Crop | Event Name | Event Code | Trait(s) | Gene(s) |
|---|---|---|---|---|
| Cotton | MON88913 | MON-88913-8 | Glyphosate tol. | cp4 epsps (aroA:CP4) |
| Cotton | Nqwe Chi 6 Bt | NA | Insect res. | NA? |
| Cotton | SKG321 | NA | Insect res. | cry1A; CpTI |
| Cotton | T303-3 | BCS-GH003-6 | Insect res.; glufosinate tol. | cry1Ab; bar |
| Cotton | T304-40 | BCS-GH004-7 | Insect res.; glufosinate tol. | cry1Ab; bar |
| Cotton | CE43-67B | | Insect res. | cry1Ab |
| Cotton | CE46-02A | | Insect res. | cry1Ab |
| Cotton | CE44-69D | | Insect res. | cry1Ab |
| Cotton | 1143-14A | | Insect res. | cry1Ab |
| Cotton | 1143-51B | | Insect res. | cry1Ab |
| Cotton | T342-142 | | Insect res. | cry1Ab |
| Cotton | PV-GHGT07 (1445) | | Glyphosate tol. | cp4 epsps (aroA:CP4) |
| Cotton | EE-GH3 | | Glyphosate tol. | mepsps |
| Cotton | EE-GH5 | | Insect res. | cry1Ab |
| Cotton | MON88701 | MON-88701-3 | Dicamba & glufosinate tol. | Modified dmo; bar |
| Cotton | OsCr11 | | Anti-allergy | Modified Cry j |
| Creeping Bentgrass | ASR368 | SMG-368ØØ-2 | Glyphosate tol. | cp4 epsps (aroA:CP4) |
| Eucalyptus | 20-C | | Salt tol. | codA |
| Eucalyptus | 12-5C | | Salt tol. | codA |
| Eucalyptus | 12-5B | | Salt tol. | codA |
| Eucalyptus | 107-1 | | Salt tol. | codA |
| Eucalyptus | 1/9/2001 | | Salt tol. | codA |
| Eucalyptus | 2/1/2001 | | Salt tol. | codA |
| Eucalyptus | | | Cold tol. | des9 |
| Flax | FP967 | CDC-FL001-2 | ALS herbicide tol. | als |
| Lentil | RH44 | | Imidazolinone tol. | als |
| Maize | 3272 | SYN-E3272-5 | Modified alpha-amylase | amy797E |
| Maize | 5307 | SYN-05307-1 | Insect res. | ecry3.1Ab |
| Maize | 59122 | DAS-59122-7 | Insect res.; glufosinate tol. | cry34Ab1; cry35Ab1; pat |
| Maize | 676 | PH-000676-7 | Glufosinate tol.; pollination control | pat; dam |
| Maize | 678 | PH-000678-9 | Glufosinate tol.; pollination control | pat; dam |
| Maize | 680 | PH-000680-2 | Glufosinate tol.; pollination control | pat; dam |
| Maize | 98140 | DP-098140-6 | Glyphosate toll; ALS herbicide tol. | gat4621; zm-hra |
| Maize | Bt10 | NA | Insect res.; glufosinate tol. | cry1Ab; pat |
| Maize | BH76 (176) | SYN-EV176-9 | Insect res.; glufosinate tol. | cry1Ab; bar |
| Maize | BVLA430101 | NA | Phytate breakdown | phyA2 |
| Maize | CBH-351 | ACS-ZM004-3 | Insect res.; glufosinate tol. | cry9C; bar |
| Maize | DAS40278-9 | DAS40278-9 | 2,4-D tol. | aad-1 |
| Maize | DBT418 | DKB-89614-9 | Insect res.; glufosinate tol. | cry1Ac; pinII; bar |
| Maize | DLL25 (B16) | DKB-89790-5 | Glufosinate tol. | bar |
| Maize | GA21 | MON-00021-9 | Glyphosate tol. | mepsps |
| Maize | GG25 | | Glyphosate tol. | mepsps |
| Maize | GJ11 | | Glyphosate tol. | mepsps |
| Maize | Fl117 | | Glyphosate tol. | mepsps |
| Maize | GAT-ZM1 | | Glufosinate tol. | pat |
| Maize | LY038 | REN-0003 8-3 | Increased lysine | cordapA |
| Maize | MIR162 | SYN-IR162-4 | Insect res. | vip3Aa20 |
| Maize | MIR604 | SYN-IR604-5 | Insect res. | mcry3A |
| Maize | MON801 (MON80100) | MON801 | Insect res.; glyphosate tol. | cry1Ab; cp4 epsps (aroA:CP4); goxv247 |
| Maize | MON802 | MON-80200-7 | Insect res.; glyphosate tol. | cry1Ab; cp4 epsps (aroA:CP4); goxv247 |
| Maize | MON809 | PH-MON-809-2 | Insect res.; glyphosate tol. | cry1Ab; cp4 epsps (aroA:CP4); goxv247 |
| Maize | MON810 | MON-00810-6 | Insect res.; glyphosate tol. | cry1Ab; cp4 epsps (aroA:CP4); goxv247 |
| Maize | MON832 | NA | Glyphosate tol. | cp4 epsps (aroA:CP4); goxv247 |
| Maize | MON863 | MON-00863-5 | Insect res. | cry3Bb1 |
| Maize | MON87427 | MON-87427-7 | Glyphosate tol. | cp4 epsps (aroA:CP4) |
| Maize | MON87460 | MON-87460-4 | Drought tol. | cspB |
| Maize | MON88017 | MON-88017-3 | Insect res.; glyphosate tol. | cry3Bb1; cp4 epsps (aroA:CP4) |
| Maize | MON89034 | MON-89034-3 | Insect res. | cry2Ab2; cry1A.105 |
| Maize | MS3 | AC S-ZM001-9 | Glufosinate tol.; pollination control | bar; barnase |
| Maize | MS6 | ACS-ZM005-4 | Glufosinate tol.; pollination control | bar; barnase |
| Maize | NK603 | MON-00603-6 | Glyphosate tol. | cp4 epsps (aroA:CP4) |
| Maize | T14 | ACS-ZM002-1 | Glufosinate tol. | pat (syn) |
| Maize | T25 | ACS-ZM003-2 | Glufosinate tol. | pat (syn) |

TABLE Z-continued

| Crop | Event Name | Event Code | Trait(s) | Gene(s) |
|---|---|---|---|---|
| Maize | TC1507 | DAS-01507-1 | Insect res.; glufosinate tol. | cry1Fa2; pat |
| Maize | TC6275 | DAS-06275-8 | Insect res.; glufosinate tol. | mocry1F; bar |
| Maize | VIP1034 | | Insect res.; glufosinate tol. | vip3A; pat |
| Maize | 43A47 | DP-043A47-3 | Insect res.; glufosinate tol. | cry1F; cry34Ab1; cry35Ab1; pat |
| Maize | 40416 | DP-040416-8 | Insect res.; glufosinate tol. | cry1F; cry34Ab1; cry35Ab1; pat |
| Maize | 32316 | DP-032316-8 | Insect res.; glufosinate tol. | cry1F; cry34Ab1; cry35Ab1; pat |
| Maize | 4114 | DP-004114-3 | Insect res.; glufosinate tol. | cry1F; cry34Ab1; cry35Ab1; pat |
| Melon | Melon A | NA | Delayed ripening/senescence | sam-k |
| Melon | Melon B | NA | Delayed ripening/senescence | sam-k |
| Papaya | 55-1 | CUH-CP551-8 | Disease res. | prsv cp |
| Papaya | 63-1 | CUH-CP631-7 | Disease res. | prsv cp |
| Papaya | Huanong No. 1 | NA | Disease res. | prsv rep |
| Papaya | X17-2 | UFL-X17CP-6 | Disease res. | prsv cp |
| Petunia | Petunia-CHS | NA | Modified product quality | CHS suppres.sion |
| Plum | C-5 | ARS-PLMC5-6 | Disease res. | ppv cp |
| Canola** | ZSR500 | NA | Glyphosate tol. | cp4 epsps (aroA:CP4); goxv247 |
| Canola** | ZSR502 | NA | Glyphosate tol. | cp4 epsps (aroA:CP4); goxv247 |
| Canola** | ZSR503 | NA | Glyphosate tol. | cp4 epsps (aroA:CP4); goxv247 |
| Poplar | Bt poplar | NA | Insect res. | cry1Ac; API |
| Poplar | Hybrid poplar clone 741 | NA | Insect res. | cry1Ac; API |
| Poplar | trg300-1 | | High cellulose | AaXEG2 |
| Poplar | trg300-2 | | High cellulose | AaXEG2 |
| Potato | 1210 amk | NA | Insect res. | cry3A |
| Potato | 2904/1 kgs | NA | Insect res. | cry3A |
| Canola** | ZSR500 | NA | Glyphosate tol. | cp4 epsps (aroA:CP4); goxv247 |
| Canola** | ZSR502 | NA | Glyphosate tol. | cp4 epsps (aroA:CP4); goxv247 |
| Potato | ATBT04-27 | NMK-89367-8 | Insect res. | cry3A |
| Potato | ATBT04-30 | NMK-89613-2 | Insect res. | cry3A |
| Potato | ATBT04-31 | NMK-89170-9 | Insect res. | cry3A |
| Potato | ATBT04-36 | NMK-89279-1 | Insect res. | cry3A |
| Potato | ATBT04-6 | NMK-89761-6 | Insect res. | cry3A |
| Potato | BT06 | NMK-89812-3 | Insect res. | cry3A |
| Potato | BT10 | NMK-89175-5 | Insect res. | cry3A |
| Potato | BT12 | NMK-89601-8 | Insect res. | cry3A |
| Potato | BT16 | NMK-89167-6 | Insect res. | cry3A |
| Potato | BT17 | NMK-89593-9 | Insect res. | cry3A |
| Potato | BT18 | NMK-89906-7 | Insect res. | cry3A |
| Potato | BT23 | NMK-89675-1 | Insect res. | cry3A |
| Potato | EH92-527-1 | BPS-25271-9 | Modified starch/carbohydrate | gbss (antisense) |
| Potato | HLMT15-15 | NA | Insect & disease res. | cry3A; pvy cp |
| Potato | HLMT15-3 | NA | Insect & disease res. | cry3A; pvy cp |
| Potato | HLMT15-46 | NA | Insect & disease res. | cry3A; pvy cp |
| Potato | RBMT15-101 | NMK-89653-6 | Insect & disease res. | cry3A; pvy cp |
| Potato | RBMT21-129 | NMK-89684-1 | Insect & disease res. | cry3A; plrv orf1; plrv orf2 |
| Potato | RBMT21-152 | NA | Insect & disease res. | cry3A; plrv orf1; plrv orf2 |
| Potato | RBMT21-350 | NMK-89185-6 | Insect & disease res. | cry3A; plrv orf1; plrv orf2 |
| Potato | RBMT22-082 | NMK-89896-6 | Insect & disease res.; Glyphosate tol. | cry3A; plrv orf1; plrv orf2; cp4 epsps (aroA:CP4) |
| Potato | RBMT22-186 | NA | Insect & disease res.; Glyphosate tol. | cry3A; plrv orf1; plrv orf2; cp4 epsps (aroA:CP4) |
| Potato | RBMT22-238 | NA | Insect & disease res.; Glyphosate tol. | cry3A; plrv orf1; plrv orf2; cp4 epsps (aroA:CP4) |
| Potato | RBMT22-262 | NA | Insect & disease res.; Glyphosate tol. | cry3A; plrv orf1; plrv orf2; cp4 epsps (aroA:CP4) |
| Potato | SEMT15-02 | NMK-89935-9 | Insect & disease res. | cry3A; pvy cp |
| Potato | SEMT15-07 | NA | Insect & disease res. | cry3A; pvy cp |
| Potato | SEMT15-15 | NMK-89930-4 | Insect & disease res. | cry3A; pvy cp |
| Potato | SPBT02-5 | NMK-89576-1 | Insect res. | cry3A |
| Potato | SPBT02-7 | NMK-89724-5 | Insect res. | cry3A |
| Rice | 7Crp#242-95-7 | | Anti-allergy | 7crp |

TABLE Z-continued

| Crop | Event Name | Event Code | Trait(s) | Gene(s) |
|---|---|---|---|---|
| Rice | 7Crp#10 | NA | Anti-allergy | 7crp |
| Rice | GM Shanyou 63 | NA | Insect res. | cry1Ab; cry1Ac |
| Rice | Huahui-1/TT51-1 | NA | Insect res. | cry1Ab; cry1Ac |
| Rice | LLRICE06 | ACS-OS001-4 | Glufosinate tol. | bar |
| Rice | LLRICE601 | BCS-OS003-7 | Glufosinate tol. | bar |
| Rice | LLRICE62 | ACS-OS002-5 | Glufosinate tol. | bar |
| Rice | Tarom molaii + cry1Ab | NA | Insect res. | cry1Ab (truncated) |
| Rice | GAT-OS2 | | Glufosinate tol. | bar |
| Rice | GAT-OS3 | | Glufosinate tol. | bar |
| Rice | PE-7 | | Insect res. | Cry1Ac |
| Rice | 7Crp#10 | NA | Anti-allergy | 7crp |
| Rice | KPD627-8 | | High tryptophan | OASA1D |
| Rice | KPD722-4 | | High tryptophan | OASA1D |
| Rice | KA317 | | High tryptophan | OASA1D |
| Rice | HW5 | | High tryptophan | OASA1D |
| Rice | HW1 | | High tryptophan | OASA1D |
| Rice | B-4-1-18 | | Erect leaves semidwarf | Δ OsBRI1 |
| Rice | G-3-3-22 | | Semidwarf | OSGA2ox1 |
| Rice | AD77 | | Disease res. | DEF |
| Rice | AD51 | | Disease res. | DEF |
| Rice | AD48 | | Disease res. | DEF |
| Rice | AD41 | | Disease res. | DEF |
| Rice | 13pNasNaatAprt1 | | Low iron tol. | HvNAS1; HvNAAT-A; APRT |
| Rice | 13pAprt1 | | Low iron tol. | APRT |
| Rice | gHvNAS1-gHvNAAT-1 | | Low iron tol. | HvNAS1; HvNAAT-A; HvNAAT-B |
| Rice | gHvIDS3-1 | | Low iron tol. | HvIDS3 |
| Rice | gHvNAAT1 | | Low iron tol. | HvNAAT-A; HvNAAT-B |
| Rice | gHvNAS1-1 | | Low iron tol. | HvNAS1 |
| Rice | NIA-OS006-4 | | Disease res. | WRKY45 |
| Rice | NIA-OS005-3 | | Disease res. | WRKY45 |
| Rice | NIA-OS004-2 | | Disease res. | WRKY45 |
| Rice | NIA-OS003-1 | | Disease res. | WRKY45 |
| Rice | NIA-OS002-9 | | Disease res. | WRKY45 |
| Rice | NIA-OS001-8 | | Disease res. | WRKY45 |
| Rice | OsCr11 | | Anti-allergy | Modified Cry j |
| Rice | 17053 | | Glyphosate tol. | cp4 epsps (aroA:CP4) |
| Rice | 17314 | | Glyphosate tol. | cp4 epsps (aroA:CP4) |
| Rose | WKS82/130-4-1 | IFD-52401-4 | Modified flower color | 5AT; bp40 (f3'5'h) |
| Rose | WKS92/130-9-1 | IFD-52901-9 | Modified flower color | 5AT; bp40 (f3'5'h) |
| Soybean | 260-05 (G94-1, G94-19, G168) | NA | Modified oil/fatty acid | gm-fad2-1 (silencing locus) |
| Soybean | A2704-12 | ACS-GM005-3 | Glufosinate tol. | pat |
| Soybean | A2704-21 | ACS-GM004-2 | Glufosinate tol. | pat |
| Soybean | A5547-127 | ACS-GM006-4 | Glufosinate tol. | pat |
| Soybean | A5547-35 | ACS-GM008-6 | Glufosinate tol. | pat |
| Soybean | CV127 | BPS-CV127-9 | Imidazolinone tol. | csr1-2 |
| Soybean | DAS68416-4 | DAS68416-4 | Glufosinate tol. | pat |
| Soybean | DP305423 | DP-305423-1 | Modified oil/fatty acid; ALS herbicide tol. | gm-fad2-l (silencing locus); gm-hra |
| Soybean | DP356043 | DP-356043-5 | Modified oil/fatty acid; glyphosate tol. | gm-fad2-l (silencing locus); gat4601 |
| Soybean | FG72 | MST-FG072-3 | Glyphosate & HPPD tol. | 2mepsps; hppdPF W336 |
| Soybean | GTS 40-3-2 (40-3-2) | MON-04032-6 | Glyphosate tol. | cp4 epsps (aroA:CP4) |
| Soybean | GU262 | ACS-GM003-1 | Glufosinate tol. | pat |
| Soybean | MON87701 | MON-87701-2 | Insect res. | cry1Ac |
| Soybean | MON87705 | MON-87705-6 | Modified oil/fatty acid; glyphosate tol. | fatbl-A (sense & antisense); fad2-1A (sense & antisense); cp4 epsps (aroA:CP4) |
| Soybean | MON87708 | MON-87708-9 | Dicamba & glyphosate tol. | dmo; cp4 epsps (aroA:CP4) |
| Soybean | MON87769 | MON-87769-7 | Modified oil/fatty acid; glyphosate tol. | Pj.D6D; Nc.Fad3; cp4 epsps (aroA:CP4) |
| Soybean | MON89788 | MON-89788-1 | Glyphosate tol. | cp4 epsps (aroA:CP4) |
| Soybean | W62 | ACS-GM002-9 | Glufosinate tol. | bar |
| Soybean | W98 | ACS-GM001-8 | Glufosinate tol. | bar |
| Soybean | MON87754 | MON-87754-1 | High oil | dgat2A |
| Soybean | DAS21606 | DAS-21606 | Aryloxyalkanoate & glufosinate tol. | Modified aad-12; pat |
| Soybean | DAS44406 | DAS-44406-6 | Aryloxy alkanoate, glyphosate & glufosinate tol. | Modified aad-12; 2mepsps; pat |
| Soybean | SYHT04R | SYN-0004R-8 | Mesotrione tol. | Modified avhppd |

TABLE Z-continued

| Crop | Event Name | Event Code | Trait(s) | Gene(s) |
|---|---|---|---|---|
| Soybean | 9582.814.19.1 | | Insect res. & glufosinate tol. | cry1Ac, cry1F, PAT |
| Squash | CZW3 | SEM-ØCZW3-2 | Disease res. | cmv cp, zymv cp, wmv cp |
| Squash | ZW20 | SEM-0ZW20-7 | Disease res. | zymv cp, wmv cp |
| Sugar Beet | GTSB77 (T9100152) | SY-GTSB77-8 | Glyphosate tol. | cp4 epsps (aroA:CP4); goxv247 |
| Sugar Beet | H7-1 | KM-000H71-4 | Glyphosate tol. | cp4 epsps (aroA:CP4) |
| Sugar Beet | T120-7 | ACS-BV001-3 | Glufosinate tol. | pat |
| Sugar Beet | T227-1 | | Glyphosate tol. | cp4 epsps (aroA:CP4) |
| Sugarcane | NXI-1T | | Drought tol. | EcbetA |
| Sunflower | X81359 | | Imidazolinone tol. | als |
| Sweet Pepper | PK-SP01 | NA | Disease res. | cmv cp |
| Tobacco | C/F/93/08-02 | NA | Oxynil tol. | bxn |
| Tobacco | Vector 21-41 | NA | Reduced nicotine | NtQPT1 (antisense) |
| Tomato | 1345-4 | NA | Delayed ripening/senescense | acc (truncated) |
| Tomato | 35-1-N | NA | Delayed ripening/senescense | sam-k |
| Tomato | 5345 | NA | Insect res. | cry 1 Ac |
| Tomato | 8338 | CGN-89322-3 | Delayed ripening/senescense | accd |
| Tomato | B | SYN-0000B-6 | Delayed ripening/senescense | pg (sense or antisense) |
| Tomato | Da | SYN-0000DA-9 | Delayed ripening/senescense | pg (sense or antisense) |
| Sunflower | X81359 | | Imidazolinone tol. | als |
| Tomato | Da Dong No 9 | NA | Modified product | NA |
| Tomato | F (1401F, h38F, 11013F, 7913F) | SYN-0000F-1 | Delayed ripening/senescense | pg (sense or antisense) |
| Tomato | FLAVR SAVR ™ | CGN-89564-2 | Delayed ripening/senescense | pg (sense or antisense) |
| Tomato | Huafan No 1 | NA | Delayed ripening/senescense | anti-efe |
| Tomato | PK-TM8805R (8805R) | NA | Disease res. | cmv cp |
| Wheat | MON71800 | MON-718ØØ-3 | Glyphosate tol. | cp4 epsps (aroA:CP4) |

*Argentine,
**Polish,
#Eggplant

Treatment of genetically modified plants and seeds with compounds of the disclosure may result in enhanced effects. For example, reduction in application rates, broadening of the activity spectrum, increased tolerance to biotic/abiotic stresses or enhanced storage stability may be greater than expected from just simple additive effects of the application of compounds of the disclosure on genetically modified plants and seeds.

Compounds of this disclosure are also useful in seed treatments for protecting seeds from invertebrate pests. In the context of the present disclosure and claims, treating a seed means contacting the seed with a biologically effective amount of a compound of this disclosure, which is typically formulated as a composition of the disclosure. This seed treatment protects the seed from invertebrate soil pests and generally can also protect roots and other plant parts in contact with the soil of the seedling developing from the germinating seed. The seed treatment may also provide protection of foliage by translocation of the compound of this disclosure or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate. Seed treatments with compounds of this disclosure can also increase vigor of plants growing from the treated seed.

One method of seed treatment is by spraying or dusting the seed with a compound of the disclosure (i.e. as a formulated composition) before sowing the seeds. Compositions formulated for seed treatment generally comprise a film former or adhesive agent. Therefore typically a seed coating composition of the present disclosure comprises a biologically effective amount of a compound of Formula 1, an N-oxide or salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Mongraph No. 57, and references listed therein.

Compounds of Formula 1 and their compositions, both alone and in combination with other insecticides and fungicides, are particularly useful in seed treatment for crops including, but not limited to, maize or corn, soybeans, cotton, cereal (e.g., wheat, oats, barley, rye and rice), potatoes, vegetables and oilseed rape.

Other insecticides with which compounds of Formula 1 can be formulated to provide mixtures useful in seed treatment include abamectin, acetamiprid, acrinathrin, amitraz, avermectin, azadirachtin, bensultap, bifenthrin, buprofezin, carbaryl, carbofuran, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiocarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of nuclear polyhedrosis viruses.

Fungicides with which compounds of Formula 1 can be formulated to provide mixtures useful in seed treatment include amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Compositions comprising compounds of Formula 1 useful for seed treatment can further comprise bacteria such as *Bacillus pumilus* (e.g., strain GB34) and *Bacillus firmus* (e.g., isolate 1582), *rhizobia* inoculants/extenders, isoflavonoids and lipo-chitooligosaccharides.

The treated seed typically comprises a compound of the present disclosure in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this disclosure can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1, an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this disclosure can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present disclosure. Combinations with spray oils, spray oil concentrations, spreader stickers, adjuvants, other solvents, and piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of a compound or a composition of the present disclosure and a carrier. One embodiment of such a spray composition comprises a biologically effective amount of a compound or a composition of the present disclosure and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

One embodiment of the present disclosure relates to a method for controlling invertebrate pests, comprising diluting the pesticidal composition of the present disclosure (a compound of Formula 1 formulated with surfactants, solid diluents and liquid diluents or a formulated mixture of a compound of Formula 1 and at least one other pesticide) with water, and optionally adding an adjuvant to form a diluted composition, and contacting the invertebrate pest or its environment with an effective amount of said diluted composition.

Although a spray composition formed by diluting with water a sufficient concentration of the present pesticidal composition can provide sufficient efficacy for controlling invertebrate pests, separately formulated adjuvant products can also be added to spray tank mixtures. These additional adjuvants are commonly known as "spray adjuvants" or"tank-mix adjuvants", and include any substance mixed in a spray tank to improve the performance of a pesticide or alter the physical properties of the spray mixture. Adjuvants can be surfactants, emulsifying agents, petroleum-based crop oils, crop-derived seed oils, acidifiers, buffers, thickeners or defoaming agents. Adjuvants are used to enhancing efficacy (e.g., biological availability, adhesion, penetration, uniformity of coverage and durability of protection), or minimizing or eliminating spray application problems associated with incompatibility, foaming, drift, evaporation, volatilization and degradation. To obtain optimal performance, adjuvants are selected with regard to the properties of the active ingredient, formulation and target (e.g., crops, insect pests).

Among the spray adjuvants, oils including crop oils, crop oil concentrates, vegetable oil concentrates and methylated seed oil concentrates are most commonly used to improve the efficacy of pesticides, possibly by means of promoting more even and uniform spray deposits. In situations where phytotoxicity potentially caused by oils or other water-immiscible liquids are of concern, spray compositions prepared from the composition of the present disclosure will generally not contain oil-based spray adjuvants. However, in situations where phytotoxicity caused by oil-based spray adjuvants is commercially insignificant, spray compositions prepared from the composition of the present composition can also contain oil-based spray adjuvants, which can potentially further increase control of invertebrate pests, as well as rainfastness.

Products identified as "crop oil" typically contain 95 to 98% paraffin or naphtha-based petroleum oil and 1 to 2% of one or more surfactants functioning as emulsifiers. Products identified as "crop oil concentrates" typically consist of 80 to 85% of emulsifiable petroleum-based oil and 15 to 20% of nonionic surfactants. Products correctly identified as "vegetable oil concentrates" typically consist of 80 to 85% of vegetable oil (i.e. seed or fruit oil, most commonly from cotton, linseed, soybean or sunflower) and 15 to 20% of nonionic surfactants. Adjuvant performance can be improved by replacing the vegetable oil with methyl esters of fatty acids that are typically derived from vegetable oils. Examples of methylated seed oil concentrates include MSO® Concentrate (UAP-Loveland Products, Inc.) and Premium MSO Methylated Spray Oil (Helena Chemical Company).

The amount of adjuvants added to spray mixtures generally does not exceed about 2.5% by volume, and more typically the amount is from about 0.1 to about 1% by volume. The application rates of adjuvants added to spray mixtures are typically between about 1 to 5 L per hectare. Representative examples of spray adjuvants include: Adigor® (Syngenta) 47% methylated rapeseed oil in liquid hydrocarbons, Silwet™ (Helena Chemical Company) polyalkyleneoxide modified heptamethyltrisiloxane and Assist® (BASF) 17% surfactant blend in 83% paraffin based mineral oil.

Nonagronomic applications include protecting an animal, particularly a vertebrate, more particularly a homeothermic vertebrate (e.g., mammal or bird) and most particularly a mammal, from an invertebrate parasitic pest by administering a parasiticidally effective (i.e. biologically effective) amount of a compound of the disclosure, typically in the form of a composition formulated for veterinary use, to the animal to be protected. Therefore of note is a method for protecting an animal comprising administering to the animal a parasiticidally effective amount of a compound of the disclosure. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

Examples of invertebrate parasitic pests controlled by administering a parasiticidally effective amount of a compound of the disclosure to an animal to be protected include ectoparasites (arthropods, acarines, etc) and endoparasites (helminths, e.g., nematodes, trematodes, cestodes, acanthocephalans, etc.). In particular, the compounds of this disclosure are effective against ectoparasites including: flies such as *Haematobia* (*Lyperosia*) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis* and *Gastrophilus naslis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea).

Nonagronomic applications in the veterinary sector are by conventional means such as by enteral administration in the form of, for example, tablets, capsules, drinks, drenching preparations, granulates, pastes, boli, feed-through procedures, or suppositories; or by parenteral administration, such as by injection (including intramuscular, subcutaneous, intravenous, intraperitoneal) or implants; by nasal administration; by topical administration, for example, in the form of immersion or dipping, spraying, washing, coating with powder, or application to a small area of the animal, and through articles such as neck collars, ear tags, tail bands, limb bands or halters which comprise compounds or compositions of the present disclosure.

Typically a parasiticidal composition according to the present disclosure comprises a mixture of a compound of Formula 1, an N-oxide or a salt thereof, with one or more pharmaceutically or veterinarily acceptable carriers comprising excipients and auxiliaries selected with regard to the intended route of administration (e.g., oral, topical or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a parasitically effective amount of a compound of the disclosure and at least one carrier.

For parenteral administration including intravenous, intramuscular and subcutaneous injection, a compound of the present disclosure can be formulated in suspension, solution or emulsion in oily or aqueous vehicles, and may contain adjuncts such as suspending, stabilizing and/or dispersing agents. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation.

For oral administration in the form of solutions (the most readily available form for absorption), emulsions, suspensions, pastes, gels, capsules, tablets, boluses powders, granules, rumen-retention and feed/water/lick blocks, a compound of the present disclosure can be formulated with binders/fillers known in the art to be suitable for oral administration compositions, such as sugars (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

Compounds of the present disclosure have been discovered to have favorable pharmacokinetic and pharmacodynamic properties providing systemic availability from oral administration and ingestion. Therefore after ingestion by the animal to be protected, parasiticidally effective concentrations of compounds of the disclosure in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the disclosure, one or more carriers selected from binders and fillers suitable for oral administration and feed concentrate carriers).

Formulations for topical administration are typically in the form of a powder, cream, suspension, spray, emulsion, foam, paste, aerosol, ointment, salve or gel. More typically a topical formulation is a water-soluble solution, which can be in the form of a concentrate that is diluted before use. Parasiticidal compositions suitable for topical administration typically comprise a compound of the present disclosure and one or more topically suitable carriers. In applications of a parasiticidal composition topically to the exterior of an animal as a line or spot (i.e. "spot-on" treatment), the active ingredient migrates over the surface of the animal to cover most or all of its external surface area. As a result, the treated animal is particularly protected from invertebrate pests that feed off the epidermis of the animal such as ticks, fleas and lice. Therefore formulations for topical localized administration often comprise at least one organic solvent to facilitate transport of the active ingredient over the skin and/or penetration into the epidermis of the animal. Solvents commonly used as carriers in such formulations include propylene glycol, paraffins, aromatics, esters such as isopropyl myristate, glycol ethers, and alcohols such as ethanol and n-propanol.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

In general for veterinary use, a compound of Formula 1, an N-oxide or a salt thereof, is administered in a parasiticidally effective amount to an animal to be protected from invertebrate parasite pests. A parasiticidally effective amount is the amount of active ingredient needed to achieve an observable effect diminishing the occurrence or activity of the target invertebrate parasite pest. One skilled in the art will appreciate that the parasitically effective dose can vary for the various compounds and compositions of the present disclosure, the desired parasitical effect and duration, the target invertebrate pest species, the animal to be protected, the mode of application and the like, and the amount needed to achieve a particular result can be determined through simple experimentation.

For oral administration to homeothermic animals, the daily dosage of a compound of the present disclosure typically ranges from about 0.01 mg/kg to about 100 mg/kg, more typically from about 0.5 mg/kg to about 100 mg/kg, of animal body weight. For topical (e.g., dermal) administration, dips and sprays typically contain from about 0.5 ppm to about 5000 ppm, more typically from about 1 ppm to about 3000 ppm, of a compound of the present disclosure.

Specific compounds of Formula 1 prepared by the methods and variations as described in preceding Schemes 1-11 and Synthesis Examples 1-2, are shown in the Index Tables A and B below. See Index Table C for $^1H$ NMR data. For mass spectral (MS) data, the numerical value reported is the molecular weight of the highest isotopic abundance parent ion (M+1) formed by addition of $H^+$ (molecular weight of 1) to the molecule, observed by mass spectrometry using atmospheric pressure chemical ionization ($AP^+$). The following abbreviations are used in the Index Tables which follow: Cmpd means Compound, t is tertiary, c is cyclo, Me is methyl, Et is ethyl, Pr is propyl, i-Pr is isopropyl, Bu is butyl, c-Pr is cyclopropyl, c-Pn is cyclopentyl, c-Hx is cyclohexyl, t-Bu is tertiary-butyl, Ph is phenyl, OMe is methoxy, SMe is methylthio, and $SO_2Me$ means methylsulfonyl. A wavy line in a structure fragment denotes the attachment point of the fragment to the remainder of the molecule. The abbreviation "Ex." stands for "Example" and is followed by a number indicating in which Synthesis Example the compound is prepared.

INDEX TABLE A

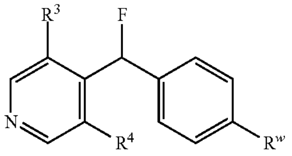

| Cmpd. No. | $R^3$ | $R^4$ | $R^w$ | MS data |
|---|---|---|---|---|
| 1 | F | pyrazol-1-yl | —$SCF_3$ | 372 |
| 2 | F | 1H-1,2,4-triazol-1-yl | —$SCF_3$ | 373 |
| 3 | F | 2H-1,2,3-triazol-2-yl | —$SCF_3$ | 373 |
| 4 | F | 3-(trifluoromethyl)-1H-pyrazol-1-yl | —$SCF_3$ | 440 |
| 5 | F | 3-methyl-1H-pyrazol-1-yl | —$SCF_3$ | 386 |
| 6 | F | 4-methyl-1H-pyrazol-1-yl | —$SCF_3$ | 386 |
| 7 | F | 1H-1,2,4-triazol-1-yl | —$SCF_3$ | 357 |
| 8 | F | 2H-1,2,3-triazol-2-yl | —$OCF_3$ | 357 |
| 9 | H | 2H-1,2,3-triazol-2-yl | —$OCF_3$ | 339 |
| 10 | H | 1H-1,2,3-triazol-1-yl | —$OCF_3$ | 339 |
| 11 | H | pyrazol-1-yl | —$OCF_3$ | 338 |
| 12 | H | 1H-1,2,4-triazol-1-yl | —$OCF_3$ | 339 |
| 13 | H | 2H-1,2,3-triazol-2-yl | —$OCF_2CHF_2$ | 389 |
| 14 | Cl | 2H-1,2,3-triazol-2-yl | —$OCF_3$ | 373 |
| 15 | Cl | 1H-1,2,4-triazol-1-yl | —$OCF_3$ | 373 |
| 17 | Br | 2H-1,2,3-triazol-2-yl | —$OCF_3$ | 417 |
| 18 | F | 1H-1,2,4-triazol-1-yl | —$CF_3$ | 341 |
| 19 | F | 2H-1,2,3-triazol-2-yl | —$OCF_3$ | 369 |
| 20 | F | 2H-1,2,3-triazol-2-yl | —$CF_3$ | 341 |
| 21 | F | pyrazol-1-yl | —$CF_3$ | 340 |
| 22 | F | furan-2-yl | —$OCF_3$ | 356 |
| 23 | F | furan-3-yl | —$OCF_3$ | 356 |
| 24 | Cl | 2$\lambda^2$-tetrazol-5-yl | —$OCF_3$ | 374 |
| 25 | F | 1-methyl-1H-imidazol-2-yl | —$OCF_3$ | 370 |
| 26 | F | 1H-pyrrol-2-yl | —$OCF_3$ | 355 |
| 27 | Br | 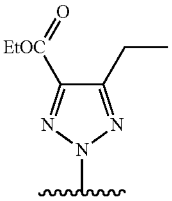 | —$OCF_3$ | 517 |
| 28 | Br | 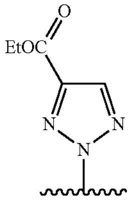 | —$OCF_3$ | 489 |
| 29 | Br | 4,5-dibromo-2H-1,2,3-triazol-2-yl | —$OCF_3$ | * |
| 30 | F | 1,3,4-oxadiazol-2-yl | —$OCF_3$ | 358 |
| 31 | F | 5-methyl-1,3,4-oxadiazol-2-yl | —$OCF_3$ | 372 |
| 32 | F | oxazol-2-yl | —$OCF_3$ | 357 |
| 33 | F | thiazol-2-yl | —$OCF_3$ | 373 |
| 34 | F | oxazol-5-yl | —$OCF_3$ | 357 |
| 35 | —OMe | oxazol-5-yl | —$OCF_3$ | 369 |
| 36 | F | thiazol-2-yl | —$OCF_3$ | * |
| 38 | Me | 2H-1,2,3-triazol-2-yl | —$OCF_3$ | 353 |
| 39 | F | 3-methyl-1,2,4-oxadiazol-5-yl | —$OCF_3$ | * |
| 40 | F | 1H-1,2,4-triazol-3-yl | —$OCF_3$ | 357 |
| 41 | F | isoxazol-5-yl | —$OCF_3$ | 357 |
| 42 | F | 1H-pyrazol-5-yl | —$OCF_3$ | 357 |
| 43 | F | 2H-1,2,3-triazol-2-yl | —C(OMe)($CF_3$)2 | 453 |
| 44 | F | 1-ethyl-1H-pyrazol-4-yl | —$OCF_3$ | 384 |
| 45 | F | thiophen-2-yl | —$OCF_3$ | 372 |

-continued

INDEX TABLE A

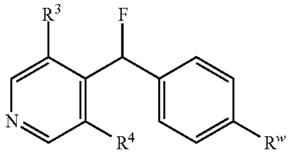

| Cmpd. No. | $R^3$ | $R^4$ | $R^w$ | MS data |
|---|---|---|---|---|
| 46 | F | thiophen-3-yl | —$OCF_3$ | 372 |
| 47 | Me | 1H-1,2,3-triazol-1-yl | —$OCF_3$ | 353 |
| 48 | CN | 2H-1,2,3-triazol-2-yl | —$OCF_3$ | * |
| 49 | F | thiazol-4-yl | —$OCF_3$ | 373 |
| 50 | Cl | thiazol-2-yl | —$OCF_3$ | 389 |
| 51 | Cl | oxazol-2-yl | —$OCF_3$ | 373 |
| 53 | c-propyl | 2H-1,2,3-triazol-2-yl | —$OCF_3$ | 379 |
| 54 | F | 2H-1,2,3-triazol-2-yl | —$SO_2CF_3$ | 405 |
| 55 | F | 1-ethyl-1H-pyrazol-5-yl | —$OCF_3$ | 384 |
| 56 | F | 1-isopropyl-1H-pyrazol-4-yl | —$OCF_3$ | 398 |
| 57 | F | 1-ethyl-1H-pyrazol-3-yl | —$OCF_3$ | 384 |
| 58 | F | 1-(2,2,2-trifluoroethyl)-1H-pyrazol-4-yl | —$OCF_3$ | 438 |
| 59 | F | 1-methyl-1H-pyrazol-3-yl | —$OCF_3$ | 370 |
| 60 | Cl | oxazol-5-yl | —$OCF_3$ | 373 |
| 61 | F | 4H-1,2,4-triazol-4-yl | —$SCF_3$ | 372 |
| 62 | F | 1-i-propyl-1H-pyrazol-3-yl | —$OCF_3$ | 398 |
| 63 | F | 1-(2,2,2-trifluoroethyl)-1H-pyrazol-3-yl | —$OCF_3$ | 438 |
| 64 | Br | 2H-1,2,3-triazol-2-yl | —$SO_2CF_3$ | 465 |
| 67 | F | 2H-1,2,3-triazol-2-yl | —$SOCF_3$ | 389 |
| 68 | H | 1H-1,2,3-triazol-1-yl | —$SCF_3$ | 355 |
| 69 | H | 2H-1,2,3-triazol-2-yl | —$SCF_3$ | 355 |
| 73 | F | pyrazol-1-yl | —$SOCF_3$ | 388 |
| 77 | F | thiazol-2-yl | —$SCF_3$ | 389 |
| 78 | F | oxazol-2-yl | —$SCF_3$ | 373 |
| 85 | Br | pyrazol-1-yl | —$SCF_3$ | 432 |
| 86 | Br | 2H-1,2,3-triazol-2-yl | —$SCF_3$ | 433 |
| 87 | Br | 1H-1,2,3-triazol-1-yl | —$SCF_3$ | 433 |
| 88 | Cl | pyrazol-1-yl | —OCF3 | 372 |
| 89 | Cl | 2H-1,2,3-triazol-2-yl | —SCF3 | 389 |
| 90 | Cl | 2H-1,2,3-triazol-2-yl | —SOCF3 | 405 |
| 91 | Cl | 2H-1,2,3-triazol-2-yl | —SO2CF3 | 421 |
| 92 | F | 2H-1,2,3-triazol-2-yl | Br | 351 |
| 93 | F | 3-methyl-1,2,4-oxadiazol-5-yl | SCF3 | 388 |
| 94 | F | 3-methyl-1,2,4-oxadiazol-5-yl | SOCF3 | 404 |
| 95 | I | 2H-1,2,3-triazol-2-yl | SCF3 | 481 |
| 96 | F | 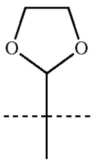 | SCF3 | 378 |
| 97 | I | 2H-1,2,3-triazol-2-yl | SOCF3 | 497 |
| 98 | F | 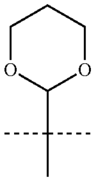 | SCF3 | 392 |
| 99 | I | 2H-1,2,3-triazol-2-yl | CF2H | 431 |
| 100 | F | oxazol-5-yl | SCF3 | 373 |
| 101 | F | oxazol-5-yl | SOCF3 | 389 |
| 102 | Cl | pyrazol-1-yl | SCF3 | 388 |

-continued

INDEX TABLE A

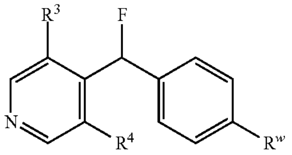

| Cmpd. No. | $R^3$ | $R^4$ | $R^w$ | MS data |
|---|---|---|---|---|
| 103 | Cl | 3-methyl-1,2,4-oxadiazol-5-yl | SCF3 | 404 |
| 104 | Cl | 3-methyl-1,2,4-oxadiazol-5-yl | SOCF3 | 420 |
| 105 | Cl | oxazol-5-yl | SCF3 | 389 |
| 106 | Cl | 1,2,4-oxadiazol-5-yl | SCF3 | 390 |
| 107 | Cl | oxazol-5-yl | SOCF3 | 405 |
| 108 | Br | 2H-1,2,3-triazol-2-yl | t-Bu | 389 |
| 109 | Cl | 2H-1,2,3-triazol-2-yl | Br | 367 |
| 110 | Cl | 2H-1,2,3-triazol-2-yl | t-Bu | 345 |
| 111 | F | Thiophene-2-yl | SCF3 | 388 |
| 112 | F | Thiophene-2-yl | SCF3 | 388 |
| 113 | F | 2-methyl-thiophene-3-yl | SCF3 | 402 |
| 114 | F | 3-methyl-thiophene-4-yl | SCF3 | 402 |
| 115 | F | 4-methyl-2H-1,2,3-triazol-2-yl | SCF3 | 387 |
| 116 | F | 4-methyl-1H-1,2,3-triazol-1-yl | SCF3 | 387 |

INDEX TABLE B

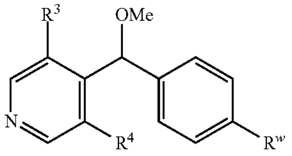

| Cmpd. No. | $R^3$ | $R^4$ | $R^w$ | MS data |
|---|---|---|---|---|
| 16 | Cl | 2H-1,2,3-triazol-2-yl | $—OCF_3$ | 385 |
| 37 | F | pyrazol-1-yl | $—OCF_3$ | 368 |
| 52 | Cl | pyrazol-1-yl | $—OCF_3$ | 384 |
| 65 | Br | 2H-1,2,3-triazol-2-yl | $—OCF_3$ | 429 |
| 66 | Br | pyrazol-1-yl | $—OCF_3$ | 428 |
| 70 | F | pyrazol-1-yl | $—SCF_3$ | 384 |
| 71 | F | 1H-1,2,4-triazol-1-yl | $—SCF_3$ | 385 |
| 72 | F | pyrazol-1-yl | $—SOCF_3$ | 400 |
| 74 | F | 1H-1,2,4-triazol-1-yl | $—SOCF_3$ | 401 |
| 75 | F | thiazol-2-yl | $—SCF_3$ | 401 |
| 76 | F | oxazol-2-yl | $—SCF_3$ | 385 |
| 79 | F | 5-methyl-1,2,4-oxadiazol-3-yl | $—SCF_3$ | 400 |
| 80 | F | 2,5-dihydro-5-oxo-1,2,4-oxadiazol-3-yl | $—SCF_3$ | 402 |
| 81 | F | 5-trifluoromethyl-1,2,4-oxadiazol-3-yl | $—SCF_3$ | 454 |
| 82 | F | 3-methyl-5-isoxazolyl | $—SCF_3$ | 399 |
| 83 | F | 1,2,4-oxadiazol-3-yl | $—SCF_3$ | 386 |
| 84 | F | 2,5-dihydro-5-thioxo-1,2,4-oxadiazol-3-yl | $—SCF_3$ | 418 |
| 117 | F | 2H-1,2,3-triazol-2-yl | Br | 363 |
| 118 | F | 2H-1,2,3-triazol-2-yl | SCF2H | 367 |
| 119 | I | pyrazol-1-yl | SCF3 | 492 |
| 120 | I | 2H-1,2,3-triazol-2-yl | SCF3 | 493 |
| 121 | F | 3-nitrile-pyrazol-1-yl | SCF3 | 409 |

-continued

INDEX TABLE B

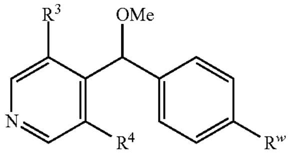

| Cmpd. No. | $R^3$ | $R^4$ | $R^w$ | MS data |
|---|---|---|---|---|
| 122 | F | 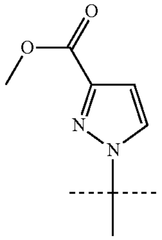 | SCF3 | 442 |
| 123 | F | 2H-1,2,3-triazol-2-yl | SCF3 | 385 |
| 124 | F | 2H-1,2,3-triazol-2-yl | OCF3 | 369/S-enantiomer** |
| 125 | F | 2H-1,2,3-triazol-2-yl | OCF3 | 369/R-enantiomer |
| 126 | Cl | 1H-1,2,3-triazol-1-yl | OCF3 | 385 |
| 127 | Cl | 2H-1,2,3-triazol-2-yl | SCF3 | 401 |
| 128 | Cl | 1H-1,2,3-triazol-1-yl | SCF3 | 401 |
| 129 | I | 2H-1,2,3-triazol-2-yl | OCF3 | 477 |
| 130 | Cl | 2H-1,2,3-triazol-2-yl | SCF3 | 401/R-enantiomer |
| 131 | Cl | 2H-1,2,3-triazol-2-yl | SCF3 | 401/S-enantiomer |
| 132 | F | 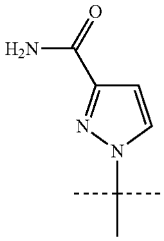 | SCF3 | |
| 133 | Br | 2H-1,2,3-triazol-2-yl | SCF3 | 445 |
| 134 | Br | 1H-1,2,3-triazol-1-yl | SCF3 | 445 |
| 135 | F | 3-methyl-1,2,4-oxadiazol-5-yl | SCF3 | 400 |
| 136 | F | 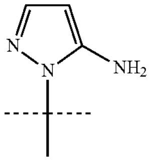 | SCF3 | 399 |
| 137 | F | 3-methyl-1,2,4-oxadiazol-5-yl | OCF3 | 384 |
| 138 | F | 1,2,4-oxadiazol-5-yl | OCF3 | 370 |
| 139 | F | 1,2,4-oxadiazol-5-yl | t-Bu | 342 |
| 140 | F | 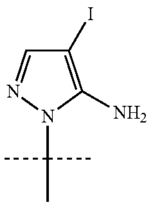 | SCF3 | 525 |
| 141 | F | 2H-1,2,3-triazol-2-yl | OCH3 | 315 |
| 142 | Cl | 3-methyl-1,2,4- | OCF3 | 400 |

-continued
INDEX TABLE B
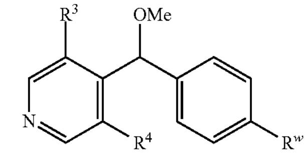
| Cmpd. No. | $R^3$ | $R^4$ | $R^w$ | MS data |
| --- | --- | --- | --- | --- |
| | | oxadiazol-5-yl | | |
| 143 | F | 4-methyl-2H-1,2,3-triazol-2-yl | SCF3 | 399 |
| 144 | Cl | 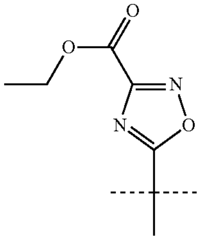 | OCF3 | 458 |
-continued
INDEX TABLE B
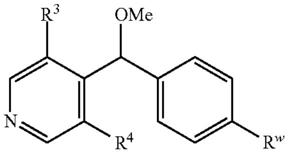
| Cmpd. No. | $R^3$ | $R^4$ | $R^w$ | MS data |
| --- | --- | --- | --- | --- |
| 145 | H | 2H-1,2,3-triazol-2-yl | OCF3 | 351 |
| 146 | Cl | 3-methyl-1,2,4-oxadiazol-5-yl | SCF3 | 416 |
**$[\alpha]_{25}$ = +153.54° [C = 0.30%, MeOH]
INDEX TABLE C
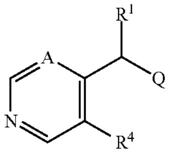
| Cmpd. No. | A | R4 | R1 | Q | MS data |
| --- | --- | --- | --- | --- | --- |
| 147 | C—Br | 2H-1,2,3-triazol-2-yl | F | 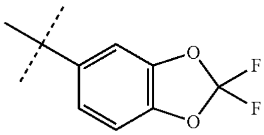 | 414 |
| 148 | C—Br | 1H-1,2,3-triazol-1-yl | F | 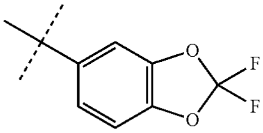 | 414 |
| 149 | C—Cl | 1H-1,2,3-triazol-1-yl | F | 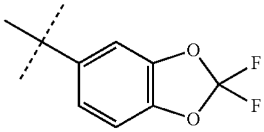 | 369 |
| 150 | C—Cl | 2H-1,2,3-triazol-2-yl | F | 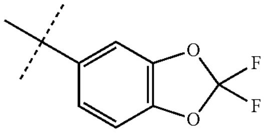 | 369 |
| 151 | C—F | pyrazol-1-yl | F | 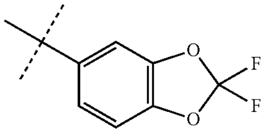 | 352 |

-continued
INDEX TABLE C
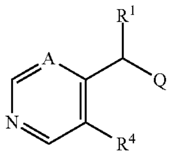
| Cmpd. No. | A | R4 | R1 | Q | MS data |
| --- | --- | --- | --- | --- | --- |
| 152 | C—F | 2H-1,2,3-triazol-2-yl | F | 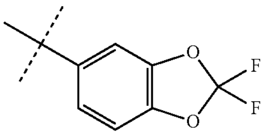 | 353 |
| 153 | C—Cl | pyrazol-1-yl | F | 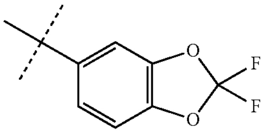 | 367 |
| 154 | C—F | pyrazol-1-yl | OEt | p-C6H4OCF3 | * |
| 155 | C—F | pyrazol-1-yl | OMe | 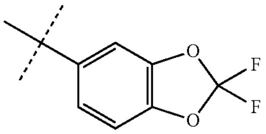 | * |
| 156 | C—F | pyrazol-1-yl | F | 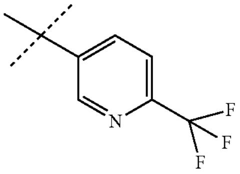 | 341 |
| 157 | C—F | pyrazol-1-yl | OMe | 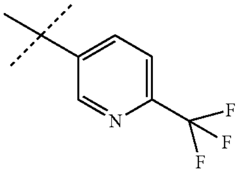 | 353 |
| 158 | C—F | 2H-1,2,3-triazol-2-yl | OMe | 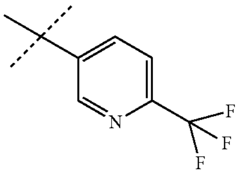 | 354 |
| 159 | C—F | 2H-1,2,3-triazol-2-yl | OMe | 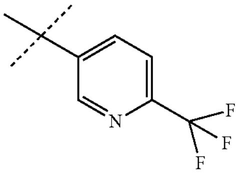 | 342 |

-continued
INDEX TABLE C
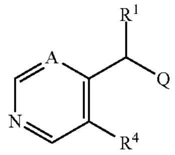
| Cmpd. No. | A | R4 | R1 | Q | MS data |
| --- | --- | --- | --- | --- | --- |
| 160 | C—F | pyrazol-1-yl | OMe | 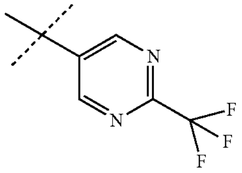 | 354 |
| 161 | C—F | 2H-1,2,3-triazol-2-yl | OMe | 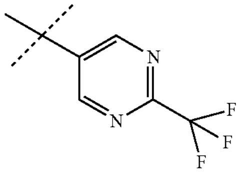 | 355 |
| 162 | C—F | pyrazol-1-yl | F | 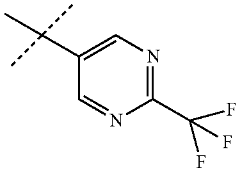 | 342 |
| 163 | C—F | 2H-1,2,3-triazol-2-yl | F | 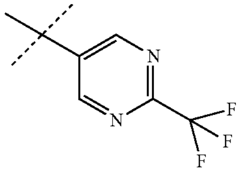 | 343 |
| 164 | C—F | pyrazol-1-yl | OMe | 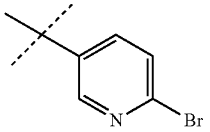 | 363 |
| 165 | C—F | pyrazol-1-yl | F | 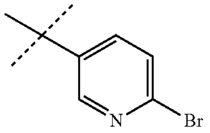 | 351 |
| 166 | C—F | 2H-1,2,3-triazol-2-yl | F | 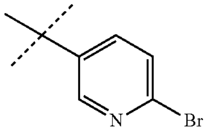 | 352 |
| 167 | C—F | 2H-1,2,3-triazol-2-yl | OMe | 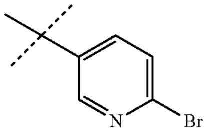 | 364 |

-continued
INDEX TABLE C
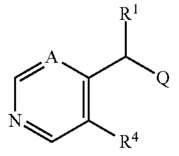
| Cmpd. No. | A | R4 | R1 | Q | MS data |
|---|---|---|---|---|---|
| 168 | C—Cl | 2H-1,2,3-triazol-2-yl | F | 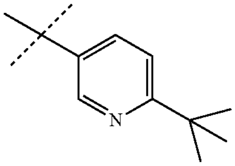 | 346 |
| 169 | C—Cl | 2H-1,2,3-triazol-2-yl | F | 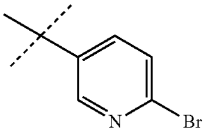 | 368 |
| 170 | C—Cl | 2H-1,2,3-triazol-2-yl | F | 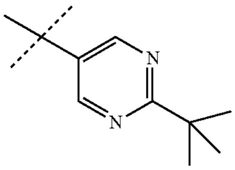 | 347 |
| 171 | C—F | pyrazol-1-yl | F | 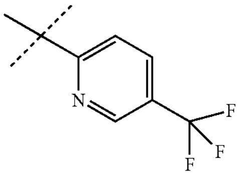 | 341 |
| 172 | C—F | 2H-1,2,3-triazol-2-yl | F | 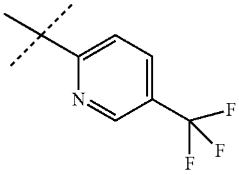 | 342 |
| 173 | C—F | pyrazol-1-yl | OMe | 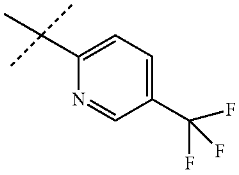 | 353 |
| 174 | C—F | 2H-1,2,3-triazol-2-yl | OMe | 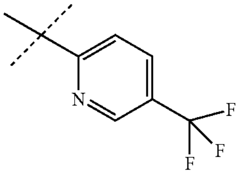 | 354 |
| 175 | N | 2H-1,2,3-triazol-2-yl | OMe | p-C6H4OCF3 | 352 |
| 176 | N | pyrazol-1-yl | OMe | p-C6H4OCF3 | 353 |
| 177 | N | pyrazol-1-yl | OMe | p-C6H4CF3 | 335 |
*See Index Table D for $^{1}$H NMR data.

INDEX TABLE D

| Cmpd. No. | $^1H$ NMR Data ($CDCl_3$ solution unless indicated otherwise)[a] |
|---|---|
| 29 | δ 8.62 (s, 1H), 8.45 (s, 1H), 7.49 (d, 2H), 7.25 (d, 2H), 6.95 (d, 1H). |
| 36 | δ 8.80 (s, br. 1H), 8.55 (s, br. 1H), 8.01 (d, 1H), 7.63 (d, 2H), 7.56 (d, 1H), 7.55 (d, 1H), 7.22 (d, 1H). |
| 39 | δ 9.13 (s, 1H), 8.68 (s, 1H), 7.71 (d, 1H), 7.56 (d, 1H), 7.23 (d, 1H), 2.52 (s, 3H). |
| 48 | δ 9.29 (s, 1H), 8.99 (s, 1H), 7.96 (s, 2H), 7.44 (d, 2H), 7.40 (d, 1H), 7.23 (d, 1H). |
| 154 | δ 8.50 (s, 1H), 8.47 (s, 1H), 7.78 (s, 1H), 7.68 (s, 1H), 7.44 (d, 2H), 7.14 (d, 2H), 6.51 (s, 1H), 5.69 (s, 1H), 3.47 (q, 2H), 1.19 (t, 3H). |
| 155 | δ ppm 3.32 (s, 3 H), 5.55 (s, 1 H), 6.55 (s, 1 H), 6.97 (d, J = 8.35 Hz, 1 H), 7.10 (d, J = 8.05 Hz, 1H), 7.25-7.28 (m, 1 H), 7.70 (d, J = 2.57 Hz, 1 H), 7.82 (s, 1 H), 8.47 (s, 1 H), 8.51 (s, 1 H). |

[a] $^1H$ NMR data are in ppm downfield from tetramethylsilane. Couplings are designated by (s)-singlet, (d)-doublet, (t)-triplet, (m)-multiplet, (dd)-doublet of doublets, (dt)-doublet of triplets, (br s)-broad singlet, (br t)-broad triplet.

The following Tests demonstrate the control efficacy of compounds of this disclosure on specific pests. "Control efficacy" represents inhibition of invertebrate pest development (including mortality) that causes significantly reduced feeding. The pest control protection afforded by the compounds is not limited, however, to these species. See Index Tables A and B for compound descriptions.

Biological Examples

Formulation and Spray Methodology for Tests A-H

Test compounds were formulated using a solution containing 10% acetone, 9000 water and 300 ppm Activator 909 non-ionic surfactant (Loveland Products, Loveland, Colorado, USA). The formulated compounds were applied in 1 mL of liquid through an atomizer nozzle positioned 1.27 cm (0.5 inches) above the top of each test unit. Test compounds were sprayed at the rates indicated, and each test was replicated three times.

Test A

For evaluating control of diamondback moth (*Plutella xylostella* (L.)) the test unit consisted of a small open container with a 12-14-day-old mustard plant inside. This was pre-infested with ~50 neonate larvae that were dispensed into the test unit via corn cob grits using an inoculator. The larvae moved onto the test plant after being dispensed into the test unit.

Test compounds were formulated and sprayed at 250 ppm. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed based on foliage consumed, and larvae were assessed for mortality.

Of the compounds of Formula 1 tested at 250 ppm, the following provided very good to excellent levels of control efficacy (40% or less feeding damage and/or 100% mortality): 1, 3, 18, 19, 20, 21, 22, 23, 29, 30, 32, 33, 34, 36, 39, 45, 48, 50, 51, 53, 55, 59, 60, 78, 89, 92, 100, 103, 104, 105, 118, 120, 123, 125, 130, 133, 147, 155, 162, 166, 171, 172, 175.

Test B

For evaluating control of corn planthopper (*Peregrinus maidis* (Ashmead)) through contact and/or systemic means, the test unit consisted of a small open container with a 3-4-day-old corn (maize) plant inside. White sand was added to the top of the soil prior to application of the test compound.

Test compounds were formulated and sprayed at 250 and/or 50 ppm and/or 10 ppm. After spraying of the formulated test compound, the test units were allowed to dry for 1 h before they were post-infested with ~15-20 nymphs (18-to-21-day-old). A black, screened cap was placed on the top of each test unit, and the test units were held for 6 days in a growth chamber at 22-24° C. and 50-70% relative humidity. Each test unit was then visually assessed for insect mortality.

Of the compounds of Formula 1 tested at 250 ppm, the following resulted in at least 80% mortality: 1, 2, 3, 4, 5, 6, 7, 8, 9, 10, 11, 12, 13, 14, 15, 16, 17, 18, 20, 21, 22, 23, 25, 26, 30, 31, 32, 33, 34, 36, 37, 38, 39, 49, 67, 69, 70, 75, 76, 77, 78, 79, 81, 82, 83, 85, 86, 88, 89, 90, 92, 93, 94, 95, 96, 98, 103, 104, 105, 106, 108, 109, 110, 111, 112, 113, 114, 120, 123, 125, 127, 130, 138, 139, 147, 156, 157, 158, 159, 161, 163, 166, 168, 169, 170, 172, 173, 174, 175.

Of the compounds of Formula 1 tested at 50 ppm, the following resulted in at least 80% mortality: 1, 2, 3, 5, 6, 7, 8, 9, 10, 11, 12, 13, 14, 15, 16, 17, 18, 19, 20, 21, 22, 23, 25, 26, 29, 30, 31, 32, 33, 34, 36, 37, 38, 39, 40, 41, 43, 45, 46, 48, 49, 50, 51, 55, 56, 57, 62, 63, 64, 65, 67, 69, 70, 76, 77, 78, 79, 83, 85, 86, 88, 89, 90, 92, 93, 94, 95, 96, 98, 103, 104, 105, 106, 108, 109, 110, 111, 112, 113, 114, 120, 123, 125, 127, 130, 138, 139, 147, 156, 157, 158, 159, 161, 163, 166, 168, 169, 170, 172, 173, 174, 175.

Of the compounds of Formula 1 tested at 10 ppm, the following resulted in at least 80% mortality: 22, 30, 32, 33, 38, 41, 43, 45, 46, 48, 49, 50, 51, 62, 69, 70, 78, 89, 92, 93, 94, 95, 96, 98, 103, 106, 109, 110, 111, 112, 113, 114, 123, 125, 127, 130, 147, 156, 159, 163, 169, 172, 173, 174.

Test C

For evaluating control of potato leafhopper (*Empoasca fabae* (Harris)) through contact and/or systemic means, the test unit consisted of a small open container with a 5-6-day-old Soleil bean plant (primary leaves emerged) inside. White sand was added to the top of the soil, and one of the primary leaves was excised prior to application of the test compound.

Test compounds were formulated and sprayed at 250 ppm. After spraying of the formulated test compound, the test units were allowed to dry for 1 hour before they were post-infested with 5 potato leafhoppers (18-to-21-day-old adults). A black, screened cap was placed on the top of the test unit, and the test units were held for 6 days in a growth chamber at 20° C. and 70% relative humidity. Each test unit was then visually assessed for insect mortality.

Of the compounds of Formula 1 tested at 250 ppm, the following resulted in at least 80% mortality: 4, 8, 9, 11, 14, 21, 32, 33, 36, 37, 69.

Test D

For evaluating control of green peach aphid (*Myzus persicae* (Sulzer)) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The aphids moved onto the test plant as the leaf piece desiccated. After pre-infestation, the soil of the test unit was covered with a layer of sand.

Test compounds were formulated and sprayed at 250 and/or 50 ppm. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality.

Of the compounds of Formula 1 tested at 250 ppm, the following resulted in at least 80% mortality: 1, 2, 3, 5, 7, 8, 11, 12, 13, 14, 15, 16, 17, 18, 19, 20, 21, 22, 23, 25, 29, 30, 34, 36, 37, 38, 39, 48, 54, 67, 68, 69, 70, 71, 72, 74, 77, 78, 79, 81, 83, 86, 87, 1, 2, 3, 5, 7, 8, 11, 12, 13, 14, 15, 16, 17, 18, 19, 20, 21, 22, 23, 25, 29, 30, 34, 36, 37, 38, 39, 48, 54, 67, 68, 69, 70, 71, 72, 74, 77, 78, 79, 81, 83, 86, 87, 88, 89, 90, 91, 93, 94, 95, 96, 97, 103, 104, 118, 123, 125, 127, 130, 147, 159, 163.

Of the compounds of Formula 1 tested at 50 ppm, the following resulted in at least 80% mortality: 2, 3, 7, 8, 13, 14, 15, 16, 17, 18, 19, 20, 21, 29, 34, 39, 48, 54, 67, 69, 71, 74, 78, 86, 89, 90, 91, 93, 94, 95, 103, 104, 118, 123, 125, 127, 130, 147, 159.

Test E

For evaluating control of cotton melon aphid (*Aphis gossypii* (Glover)) through contact and/or systemic means, the test unit consisted of a small open container with a 5-day-old okra plant inside. This was pre-infested with 30-40 insects on a piece of leaf according to the cut-leaf method, and the soil of the test unit was covered with a layer of sand.

Test compounds were formulated and sprayed at 250 and/or 50 ppm. After spraying, the test units were maintained in a growth chamber for 6 days at 19° C. and 70% relative humidity. Each test unit was then visually assessed for insect mortality.

Of the compounds of Formula 1 tested at 250 ppm, the following resulted in at least 80% mortality: 1, 2, 3, 7, 8, 9, 11, 12, 14, 16, 17, 19, 20, 21, 22, 29, 32, 33, 34, 36, 37, 38, 39, 41, 45, 49, 50, 51, 52, 54, 56, 57, 59, 60, 62, 64, 67, 68, 69, 70, 71, 72, 73, 74, 75, 76, 77, 78, 79, 83, 84, 85, 86, 88, 89, 90, 91, 92, 93, 94, 95, 96, 97, 100, 102, 103, 104, 105, 106, 109, 111, 112, 113, 118, 123, 125, 127, 130, 133, 147, 148, 154, 156, 157, 158, 159, 160, 161, 163, 166, 169, 171, 172, 174, 175, 176.

Of the compounds of Formula 1 tested at 50 ppm, the following resulted in at least 80% mortality: 1, 3, 8, 9, 11, 12, 14, 16, 17, 19, 20, 21, 22, 29, 32, 33, 34, 36, 37, 38, 39, 45, 50, 51, 54, 67, 68, 69, 70, 71, 73, 74, 76, 78, 83, 85, 86, 88, 89, 90, 91, 92, 93, 94, 95, 96, 97, 100, 102, 103, 104, 105, 106, 109, 111, 112, 113, 118, 123, 125, 127, 130, 133, 147, 148, 154, 156, 157, 158, 159, 160, 161, 163, 166, 169, 171, 172, 174, 175, 176.

Test F

For evaluating control of the sweetpotato whitefly (*Bemisia tabaci* (Gennadius)) through contact and/or systemic means, the test unit consisted of a small open container with a 12-14-day-old cotton plant inside. Prior to the spray application, both cotyledons were removed from the plant, leaving one true leaf for the assay. Adult whiteflies were allowed to lay eggs on the plant and then were removed from the test unit. Cotton plants infested with at least 15 eggs were submitted to the test for spraying.

Test compounds were formulated and sprayed at 250 and/or 50 ppm. After spraying, the test units were allowed to dry for 1 hour. The cylinders were then removed, and the units were taken to a growth chamber and held for 13 days at 28° C. and 50-70% relative humidity. Each test unit was then visually assessed for insect mortality.

Of the compounds of Formula 1 tested at 250 ppm, the following resulted in at least 70% mortality: 1, 3, 12, 13, 14, 15, 17, 19, 29, 36, 37, 39, 67, 69, 71, 78, 88, 89, 90, 91, 92, 93, 94, 95, 108, 109, 117, 118, 120, 123, 125, 127, 133, 134, 147, 155, 156, 168, 172.

Of the compounds of Formula 1 tested at 50 ppm, the following resulted in at least 70% mortality: 1, 13, 14, 19, 69, 71, 78, 88, 89, 90, 91, 92, 93, 94, 95, 108, 109, 117, 118, 120, 123, 125, 127, 133, 134, 147, 155, 156, 168, 172.

Test G

For evaluating control of the Western Flower *Thrips* (*Frankliniellla occidentalis* (Pergande)) through contact and/or systemic means, the test unit consisted of a small open container with a 5-7-day-old Soleil bean plant inside.

Test compounds were formulated and sprayed at 250 ppm. After spraying, the test units were allowed to dry for 1 hour, and then about 60 thrips (adults and nymphs) were added to each unit. A black, screened cap was placed on top, and the test units were held for 6 days at 25° C. and 45-55% relative humidity. Each test unit was then visually assessed for plant damage and insect mortality.

Of the compounds of Formula 1 tested at 250 ppm, the following provided very good to excellent levels of control efficacy (30% or less plant damage and/or 100% mortality): 1, 19, 29, 32, 33, 36, 41, 50.

Additional Example

Control Efficacy and Vapor Pressure

The values of control efficacy and vapor pressure for compounds 8 and A are shown in Additional Table 1.

| Additional Table 1 | | | | | | | | |
|---|---|---|---|---|---|---|---|---|
| | Compound | | | | | | | |
| | 8 | | | | A | | | |
| | Structure | | | | | | | |
| | 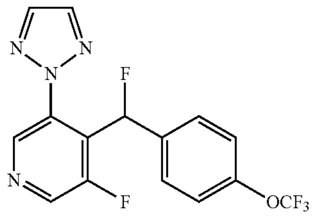 [SMILES: Fc1cncc(-n2nccn2)c1C(F)c1ccc(OC(F)(F)F)cc1] | | | | 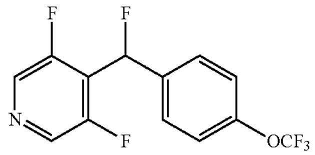 | | | |
| Control Efficacy | CMA | GPA | CPH | PLH | CMA | GPA | CPH | PLH |
| 250 ppm | 80 | 100 | 100 | 93 | 72 | L | 92 | L |
| 50 ppm | 96 | 100 | 100 | 0 | 67 | L | 100 | L |
| 10 ppm | 88 | 94 | 95 | | | | 53 | |
| 2 ppm | 79 | 100 | 89 | | | | 4 | |
| Vapor Pressure | | 6.04E−06 | | | | 1.45E−03 | | |

CMA represents cotton melon aphid; GPA represents green peach aphid; CPH represents corn planthopper; PLH represents potato leafhopper.

The testing protocols for the control efficacy of both compounds are as described in the Biological Examples section.

The procedures to obtain the vapor pressure values for both compounds are as follows: A solution of the test compound was prepared in acetonitrile at a concentration of 50 μg/mL and was then analyzed by gas chromatography/mass spectrometry (GC/MS). A linear correlation of retention times vs. known vapor pressure values of standard compounds is used to obtain an estimate of the vapor pressure of the test compounds by using interpolation. Detection and retention time of the subject compounds are confirmed by interpretation of the mass spectrum.

Surprisingly, the results show that compound 8 of this disclosure demonstrates significantly higher control efficacy than compound A on species of CMA, GPA and CPH down to 2 ppm and PLH at 250 ppm. The results also show that the vapor pressure of compound 8 is significantly lower than that of compound A, almost 1000 times lower. It is noted that the only structure difference between compounds 8 and A is that compound 8 of Formula 1 has $R^4$ as a 5-membered heterocyclic ring triazol-1-yl while compound A has $R^4$ as F which excludes compound A from the scope of this disclosure. While not being bound to this theory, it is contemplated that $R^4$ as a heterocyclic ring, making the compound less volatile, may at least partially account for the higher control efficacy.

What is claimed is:

1. A compound selected from Formula 1, an N-oxides or salt thereof,

1

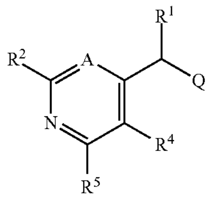

wherein $R^1$ is F;

A is N or $CR^3$;

$R^2$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^3$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

$R^4$ is selected from U-31 to U-35 and U-44 to U-48

U-31

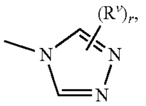

U-32

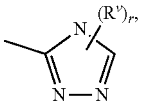

U-33

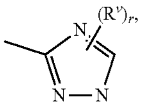

U-34

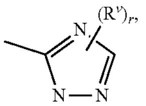

U-35

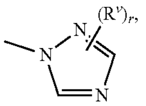

U-44

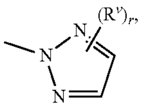

-continued

U-45

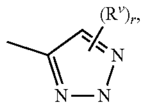

U-46

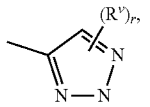

U-47

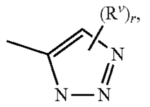

U-48

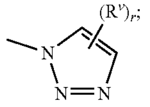

each $R^v$ is independently H, cyano, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_2$-$C_6$ cyanoalkyl, $C_1$-$C_6$ hydroxyalkyl, $C_4$-$C_{10}$ alkylcycloalkyl, $C_4$-$C_{10}$ cycloalkylalkyl, $C_3$-$C_6$ cycloalkenyl, $C_3$-$C_6$ halocycloalkenyl, $C_2$-$C_6$ alkoxyalkyl, $C_4$-$C_{10}$ cycloalkoxyalkyl, $C_3$-$C_{10}$ alkoxyalkoxyalkyl, $C_2$-$C_6$ alkylthioalkyl, $C_2$-$C_6$ alkylsulfinylalkyl, $C_3$-$C_6$ cycloalkoxy, $C_3$-$C_6$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkoxyalkoxy, $C_2$-$C_6$ alkylcarbonyloxy, $C_1$-$C_6$ alkylthio, $C_1$-$C_6$ haloalkylthio, $C_3$-$C_6$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_6$ cycloalkylsulfonyl, $C_1$-$C_6$ alkylamino, $C_2$-$C_6$ dialkylamino, $C_1$-$C_6$ haloalkylamino, $C_2$-$C_6$ halodialkylamino or $C_3$-$C_6$ cycloalkylamino;

r is 1, 2, 3, 4 or 5;

$R^5$ is H, halogen, CN, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy or $C_1$-$C_4$ haloalkoxy;

Q is a six membered aromatic ring containing ring members selected from carbon atoms and up to 2 nitrogen atoms, $R^w$ is independently H, cyano, halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_2$-$C_6$ cyanoalkyl, $C_1$-$C_6$ hydroxyalkyl, $C_4$-$C_{10}$ alkylcycloalkyl, $C_4$-$C_{10}$ cycloalkylalkyl, $C_3$-$C_6$ cycloalkenyl, $C_3$-$C_6$ halocycloalkenyl, $C_2$-$C_6$ alkoxyalkyl, $C_4$-$C_{10}$ cycloalkoxyalkyl, $C_3$-$C_{10}$ alkoxyalkoxyalkyl, $C_2$-$C_6$ alkylthioalkyl, $C_2$-$C_6$ alkylsulfinylalkyl, $C_1$-$C_6$ alkoxy, $C_1$-$C_6$ haloalkoxy, $C_3$-$C_6$ cycloalkoxy, $C_3$-$C_6$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkoxyalkoxy, $C_2$-$C_6$ alkylcarbonyloxy, $C_1$-$C_6$ alkylthio, $C_1$-$C_6$ haloalkylthio, $C_3$-$C_6$ cycloalkylthio, $C_1$-$C_6$ alkylsulfinyl, $C_1$-$C_6$ haloalkylsulfinyl, $C_3$-$C_6$ cycloalkylsulfinyl, $C_1$-$C_6$ alkylsulfonyl, $C_1$-$C_6$ haloalkylsulfonyl, $C_3$-$C_6$ cycloalkylsulfonyl, $C_1$-$C_6$ alkylamino, $C_2$-$C_6$ dialkylamino, $C_1$-$C_6$ haloalkylamino, $C_2$-$C_6$ halodialkylamino or $C_3$-$C_6$ cycloalkylamino; or two $R^w$ on adjacent carbon atoms together can form a —OCF2O—, —OCH2O—, —OCF2S—, —OCH2CH2)-, OCF2CF2O— cyclic ether ring;

s is 1, 2, 3, 4 or 5;

n is 0, 1 or 2.

2. The compound of claim 1 wherein:

A is $CR^3$.

3. The compound of claim 2 wherein:

$R^2$ is H, or halogen.

4. The compound of claim 3 wherein:

$R^2$ is H;

$R^3$ is H or halogen.

5. The compound of claim 1 wherein the compound is selected from the group consisting of:

3-Fluoro-4-[fluoro[4-(trifluoromethoxy)phenyl]methyl]-5-(2H-1,2,3-triazol-2-yl)pyridine;

3-Chloro-4-[fluoro[4-(trifluoromethoxy)phenyl]methyl]-5-(2H-1,2,3-triazol-2-yl)pyridine;

3-Fluoro-4-[fluoro[4-[(trifluoromethyl)thio]phenyl]methyl]-5-(2H-1,2,3-triazol-2-yl)pyridine;

3-Chloro-4-[fluoro[4-[(trifluoromethyl)thio]phenyl]methyl]-5-(2H-1,2,3-triazol-2-yl)pyridine;

3-Fluoro-4-[fluoro[4-(trifluoromethyl)phenyl]methyl]-5-(2H-1,2,3-triazol-2-yl)pyridine;

3-Fluoro-4-[fluoro[4-[(trifluoromethyl)sulfinyl]phenyl]methyl]-5-(2H-1,2,3-triazol-2-yl)pyridine;

3-Bromo-4-[fluoro[4-[(trifluoromethyl)thio]phenyl]methyl]-5-(2H-1,2,3-triazol-2-yl)pyridine.

6. The compound of claim 5 wherein the compound is selected from the group consisting of:

3-Fluoro-4-[fluoro[4-(trifluoromethoxy)phenyl]methyl]-5-(2H-1,2,3-triazol-2-yl)pyridine;

3-Chloro-4-[fluoro[4-(trifluoromethoxy)phenyl]methyl]-5-(2H-1,2,3-triazol-2-yl)pyridine;

3-Chloro-4-[fluoro[4-[(trifluoromethyl)thio]phenyl]methyl]-5-(2H-1,2,3-triazol-2-yl)pyridine;

3-Fluoro-4-[fluoro[4-[(trifluoromethyl)thio]phenyl]methyl]-5-(2H-1,2,3-triazol-2-yl)pyridine;

3-Bromo-4-[fluoro[4-[(trifluoromethyl)thio]phenyl]methyl]-5-(2H-1,2,3-triazol-2-yl)pyridine.

7. A composition comprising a compound of claim 1 and at least one additional component selected from the group consisting of surfactants, solid diluents and liquid diluents, said composition optionally further comprising at least one additional biologically active compound or agent.

8. The composition of claim 7 wherein the at least one additional biologically active compound or agent is selected from the group consisting of abamectin, acephate, acequinocyl, acetamiprid, acrinathrin, afidopyropen, amidoflumet, amitraz, avermectin, azadirachtin, azinphos-methyl, benfuracarb, bensultap, bifenthrin, bifenazate, bistrifluron, borate, bromantraniliprole, buprofezin, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyclaniliprole, cycloprothrin, cycloxaprid, cyflumetofen, cyfluthrin, beta-cyfluthrin, cyhalodiamide, cyhalothrin, gamma-cyhalothrin, lambda-cyhalothrin, cypermethrin, alpha-cypermethrin, zeta-cypermethrin, cyromazine, deltamethrin, diafenthiuron, diazinon, dichlorantraniliprole, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin, flonicamid, flubendiamide, flucythrinate, flufenerim, flufenoxuron, flufenoxystrobin, fluensulfone, fluopyram, flupyradifurone, fluvalinate, tau-fluvalinate, fonophos, formetanate, fosthiazate, halofenozide, heptafluthrin, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiocarb, methomyl, methoprene, methoxychlor, methoxyfenozide, metofluthrin, monocrotophos, monofluorothrin, nicotine, N-[1,1-dimethyl-2-(methylthio)ethyl]-7-fluoro-2-(3-pyridinyl)-2H-indazole-4-carboxamide, N-[1,1-dimethyl-2-(methylsulfinyl)ethyl]-7-fluoro-2-(3-pyridinyl)-2H-indazole-4-carboxamide, N-[1,1-dimethyl-2-(methylsulfonyl)ethyl]-7-fluoro-2-(3-pyridinyl)-2H-indazole-4-carboxamide, N-(1-netliylcyclopropyl)-2-(3-pyridinyl)-2H-indazole-4-carboxanide, N-[1-(difluoromethyl)cyclopropyl]-2-(3-pyridinyl)-2H-indazole-4-carboxamide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide, pymetrozine, pyrafluprole, pyrethrin, pyridaben, pyridalyl, pyrifluquinazon, pyriminostrobin, pyriprole, pyriproxyfen, rotenone, ryanodine, silafluofen, spinetoram, spinosad, spirodiclofen, spiromesifen, spirotetramat, sulprofos, sulfoxaflor, tebufenozide, tebufenpyrad, teflubenzuron, tefluthrin, tetrachlorantraniliprole, tetrachlorvinphos, tetramethrin, tetramethylfluthrin, thiacloprid, thiamethoxam, thiodicarb, thiosultap-sodium, tioxazafen, tolfenpyrad, tralomethrin, triazamate, trichlorfon, triflumezopyrim, triflumuron, *Bacillus thuringiensis* delta-endotoxins, entomopathogenic bacteria, entomopathogenic viruses and entomopathogenic fungi.

9. A composition for protecting an animal from an invertebrate parasitic pest comprising a parasiticidally effective amount of a compound of claim 1 and at least one carrier.

10. A method for controlling an invertebrate pest comprising contacting the invertebrate pest or its environment with a biologically effective amount of a compound of claim 1.

11. The method of claim 10 wherein invertebrate pest comprises stink bugs from the family Pentatomidae.

12. A treated seed comprising a compound of claim 1 in an amount of from about 0.0001 to 1% by weight of the seed before treatment.

* * * * *